United States Patent
Huganir et al.

(10) Patent No.: US 11,618,900 B2
(45) Date of Patent: Apr. 4, 2023

(54) MODULATING SYNGAP

(71) Applicant: The Johns Hopkins University, Baltimore, MD (US)

(72) Inventors: Richard Huganir, Baltimore, MD (US); Ingie Hong, Baltimore, MD (US); Yoichi Araki, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 71 days.

(21) Appl. No.: 17/085,841

(22) Filed: Oct. 30, 2020

(65) Prior Publication Data

US 2021/0180062 A1    Jun. 17, 2021

Related U.S. Application Data

(60) Provisional application No. 62/968,663, filed on Jan. 31, 2020, provisional application No. 62/929,525, filed on Nov. 1, 2019.

(51) Int. Cl.
| | | |
|---|---|---|
| *C07H 21/04* | (2006.01) | |
| *C12N 15/113* | (2010.01) | |
| *C12Q 1/6883* | (2018.01) | |

(52) U.S. Cl.
CPC .......... *C12N 15/113* (2013.01); *C12Q 1/6883* (2013.01); *C12N 2310/11* (2013.01)

(58) Field of Classification Search
None
See application file for complete search history.

(56) References Cited

U.S. PATENT DOCUMENTS

| 6,723,838 B1 | 4/2004 | Kim et al. |
| 2013/0065238 A1 | 3/2013 | Michaud et al. |

FOREIGN PATENT DOCUMENTS

| WO | WO2017/106377 | 6/2017 |

OTHER PUBLICATIONS

Kozol, Robert A., et al. ("Two knockdown models of the autism genes SYNGAP1 and SHANK3 in zebrafish produce similar behavioral phenotypes associated with embryonic disruptions of brain morphogenesis." Human molecular genetics 24.14 (2015): 4006-4023).*
Araki, Yoichi, et al. ("SynGAP isoforms differentially regulate synaptic plasticity and dendritic development." Elife 9 2020).*
Aceti et al., "Haploinsufficiency damages a postnatal critical period of pyramidal cell structural maturation linked to cortical circuit assembly" Biol Psychiatry, 2015, 77:805-815.
Araki et al., "Rapid dispersion of SynGAP from synaptic spines triggers AMPA receptor insertion and spine enlargement during LTP," Neuron, 2015, 85:173-189.
Berryer et al., "Mutations in SYNGAP1 cause intellectual disability, autism, and a specific form of epilepsy by inducing haploinsufficiency," HumMutat., 2013, 34:385-394.
Carlisle et al., "SynGAP regulates steady-state and activity-dependent phosphorylation of cofilin," J Neurosci., 2008, 28:13673-13683.
Carvill et al., "Targeted resequencing in epileptic encephalopathies identifies de novo mutations in CHD2 and SYNGAP1," Nat Genet., 2013, 45:825-830.
Chen et al., "Regulation of cortical dendrite development by Rap1 signaling," Mol Cell Neurosci., 2005, 28:215-228.
Chen et al., "A synaptic Ras-GTPase activating protein (p135 SynGAP) inhibited by CaM kinase II," Neuron, 1998, 20:895-904.
Clement et al., "Pathogenic SYNGAP1 mutations impair cognitive development by disrupting maturation of dendritic spine synapses," Cell, 2012, 151:709-723.
Cook et al., "De novo autosomal dominant mutation in SYNGAP1," Autism Res., 2011, 4:155-156.
Dosemeci et al., "Regulation of phosphorylation at the postsynaptic density during different activity states of Ca2+/calmodulin-dependent protein kinase II," Biochem Biophys Res Commun., 2010, 391:78-84.
Fitzgerald et al., "Large-scale discovery of novel genetic causes of developmental disorders," Nature, 2014, 519:223-228.
Fu et al., "Differential roles of Rap1 and Rap2 small GTPases in neurite retraction and synapse elimination in hippocampal spiny neurons," J Neurochem, 2007, 100:118-131.
Grant et al., "Multiprotein complex signaling and the plasticity problem," Curr Opin Neurobiol., 2001, 11:363-368.
Guo et al., "Reduced expression of the NMDA receptor-interacting protein SynGAP causes behavioral abnormalities that model symptoms of Schizophrenia," Neuropsychopharmacology, 2009, 34:1659-1672.
Gusella, et al., "A polymorphic DNA marker genetically linked to Huntington's disease," Nature, 1983, 306: 234.
Hamdan et al., "Mutations in SYNGAP1 in autosomal nonsyndromic mental retardation," N Engl J Med., 2009, 360:599-605.
Hamdan et al., "De novo SYNGAP1 mutations in nonsyndromic intellectual disability and autism," Biol Psychiatry, 2011, 69:898-901.
Harvey et al., "The spread of Ras activity triggered by activation of a single dendritic spine," Science, 2008, 321:136-140.
Holder et al.,".SYNGAP1-Related Intellectual Disability," In GeneReviews, 2019, 13 pages.
Hyman et al., "Liquid-liquid phase separation in biology," Annu Rev Cell Dev Biol., 2014, 30:39-58.
Khosravi-Far et al., "Ras (CXXX) and Rab (CC/CXC) prenylation signal sequences are unique and functionally distinct," J Biol Chem., 1992, 267: 24363-24368.

(Continued)

*Primary Examiner* — Kimberly Chong
(74) *Attorney, Agent, or Firm* — Fish & Richardson P.C.

(57) ABSTRACT

Disclosed are methods and compositions for treating a neurodevelopmental disorder in a subject in need thereof. In some aspects, the method includes administering an effective amount of an agent, wherein administering the agent modulates expression of one or more isoforms of synaptic GTPase-activating protein (SynGAP).

9 Claims, 24 Drawing Sheets
Specification includes a Sequence Listing.

(56) References Cited

OTHER PUBLICATIONS

Kim et al., "SynGAP: a synaptic RasGAP that associates with the PSD-95/SAP90 protein family," Neuron, 1998, 20:683-691.
Kim et al., "The role of synaptic GTPase-activating protein in neuronal development and synaptic plasticity," J Neurosci., 2003, 23: 1119-1124.
Kohmura et al.,."Diversity revealed by a novel family of cadherins expressed in neurons at a synaptic complex," Neuron, 1998, 20:1137-1151.
Komiyama et al.,"SynGAP regulates ERK/MAPK signaling, synaptic plasticity, and learning in the complex with postsynaptic density 95 and NMDA receptor," J Neurosci., 2002, 22:9721-9732.
Kumar et al., "Regulation of dendritic morphogenesis by Ras-PI3K-Akt-mTOR and Ras-MAPK signaling pathways," J Neurosci., 2005, 25:11288-11299.
Lautz e al., "Synaptic activity induces input-specific rearrangements in a targeted synaptic protein interaction network," J Neurochem., 2018, 146: 540-559.
Lautz et al.,."Activity-dependent changes in synaptic protein complex composition are consistent in different detergents despite differential solubility," Sci Rep, 2019, 9:10890.
Li et al., "Characterization of a novel synGAP isoform, synGAP-beta," J Biol Chem., 2001, 276:21417-21424.
Liao et al., "Activation of silent synapses by rapid activity-dependent synaptic recruitment of AMPA receptors," J Neurosci., 2001, 21: 6008-6017.
Lin et al., "Regulation of AMPA receptor extrasynaptic insertion by 4.1N, phosphorylation and palmitoylation," Nat Neurosci., 2009, 12: 879-887.
Lu et al.,"Activation of synaptic NMDA receptors induces membrane insertion of new AMPA receptors and LTP in cultured hippocampal neurons," Neuron 2001, 29:243-254.
Magee et al.,"New insights into the interaction of Ras with the plasma membrane," Cell, 1999, 98:9-12.
McMahon et al., "SynGAP isoforms exert opposing effects on synaptic strength," Nat Commun., 2012, 3:900.
Michaelson et al., "SYNGAP1 heterozygosity disrupts sensory processing by reducing touch-related activity within somatosensory cortex circuits," Nat Neurosci., 2018, 21:1-13.
Moores et al., "Sequence dependence of protein isoprenylation," J Biol Chem., 1991, 266:14603-14610.
Nakayama et al., "Small GTPases Rac and Rho in the maintenance of dendritic spines and branches in hippocampal pyramidal neurons," J Neurosci., 2000, 20:5329-5338.
Parker et al., "De novo, heterozygous, loss-of-function mutations in SYNGAP1 cause a syndromic form of intellectual disability," Am J Med Genet Part A, 2015, 167: 2231-2237.
Pena et al., "The C2 domain of SynGAP is essential for stimulation of the Rap GTPase reaction," EMBO Rep., 2008, 9, 350-355.
Rauch et al., "Range of genetic mutations associated with severe non-syndromic sporadic intellectual disability: anexome sequencing study," Lancet, 2012, 380:1674-1682.
Reche et al., "Sequence variability analysis of human class I and class II MHC molecules: functional and structural correlates of amino acid polymorphisms," J Mol Biol., 2003, 331:623-641.
Rumbaugh et al., "SynGAP regulates synaptic strength and mitogen-activated protein kinases in cultured neurons," Proc Natl Acad Sci U S A, 2006, 103:4344-4351.
Saito et al., "Plexin-B1 is a GTPase activating protein for M-Ras, remodelling dendrite morphology," EMBO Rep., 2009, 10:614-621.
Satterstrom et al., Large-Scale Exome Sequencing Study Implicates Both Developmental and Functional Changes in the Neurobiology of Autism. Cell, 2020 180: 1-17.
Schafer et al., "Pathological priming causes developmental gene network heterochronicity in autistic subject-derived neurons," Nat Neurosci., 2019, 22, 243-255.
Sepulveda et al.,"Differential roles of NMDA Receptor Subtypes NR2A and NR2B in dendritic branch development and requirement of RasGRF1," J Neurophysiol., 2010, 103:1758-1770.
Shin, "Liquid phase condensation in cell physiology and disease," Science., 2017, 357.
Sholl, "Dendritic organization in the neurons of the visual and motor cortices of the cat," J. Anat., 1953, 387-406.
Simanshu et al., "RAS Proteins and Their Regulators in Human Disease," Cell, 2017, 170:17-33.
Sommer, The importance of immune gene variability (MHC) in evolutionary ecology and conservation, Front Zool., 2005, 2:16.
Tan et al., "Characterization of patients referred for non-specific intellectual disability testing: the importance of autosomal genes for diagnosis," Clin Genet., 2015, 519, 223-228.
Vissers et al., "A de novo paradigm for mental retardation," Nat Genet., 2010, 42:1109-1112.
Vlaskamp et al.,"SYNGAP1 encephalopathy: A distinctive generalized developmental and epileptic encephalopathy," 2019, Neurology 92:e96-e107.
Walkup et al., "A model for regulation by SynGAP-alpha1 of binding of synaptic proteins to PDZ-domain 'Slots' in the postsynaptic density," Elife, 2016, 5:e16183.
Wright et al., "CAAX modification and membrane targeting of Ras,". J Lipid Res., 2006, 47:883-891.
Writzl et al., "6p21.3 microdeletion involving the SYNGAP1 gene in a patient with intellectual disability, seizures, and severe speech impairment," Am J Med Genet Part A, 2013, 161:1682-1685.
Yang et al., "SynGAP moves out of the core of the postsynaptic density upon depolarization," Neuroscience, 2011, 192:132-139.
Yang et al.,"Camkii-mediated phosphorylation regulates distributions of Syngap-alpha1 and -alpha2 at the postsynaptic density," PLoS One 8, 2013, e71795.
Yokoi et al.,"3'UTR Length-Dependent Control of SynGAP Isoform alpha2 mRNA by FUS and ELAV-like Proteins Promotes Dendritic Spine Maturation and Cognitive Function," Cell Rep, 2017, 20:3071-3084.
Zeng et al., "Phase Transition in Postsynaptic Densities Underlies Formation of Synaptic Complexes and Synaptic Plasticity," Cell, 2016, 166:1163-1175 e1112.
Zeng et al., "Reconstituted Postsynaptic Density as a Molecular Platform for Understanding Synapse Formation and Plasticity," Cell, 2018, 174:1172-1187 e1116.
Zhu et al., "Ras and Rap control AMPA receptor trafficking during synaptic plasticity," Cell, 2002, 110:443-455.

\* cited by examiner

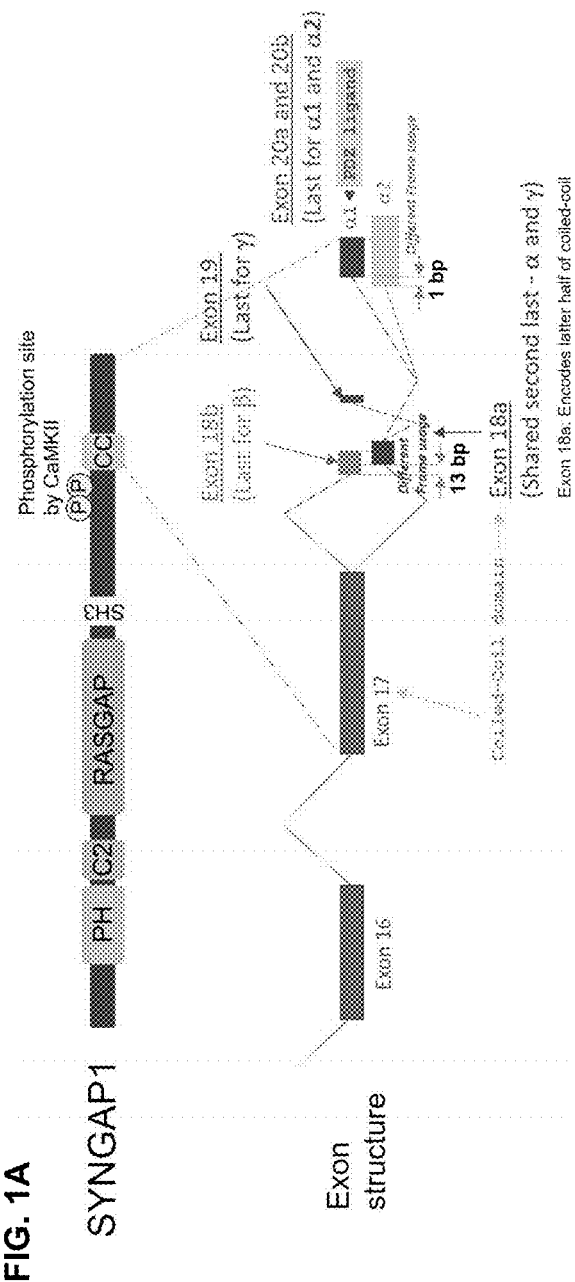

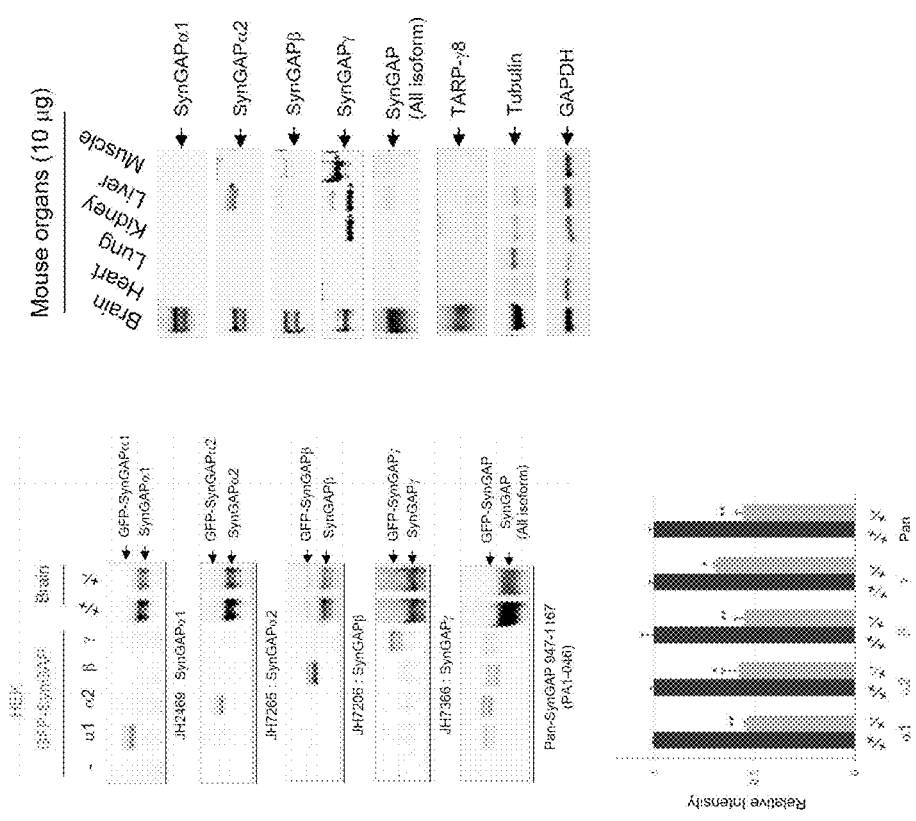

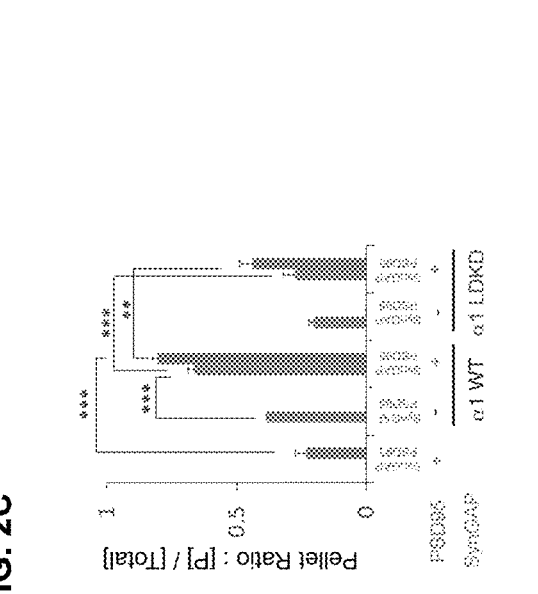
FIG. 2A
FIG. 2B
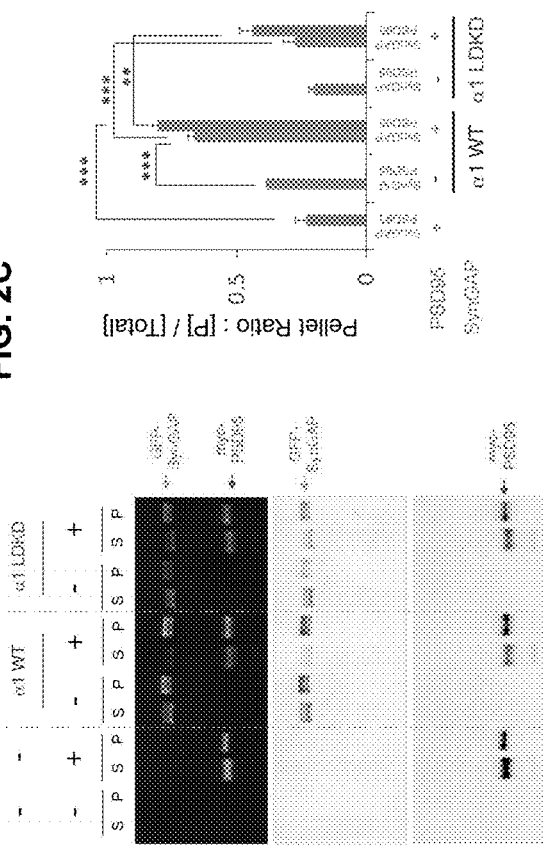
FIG. 2C
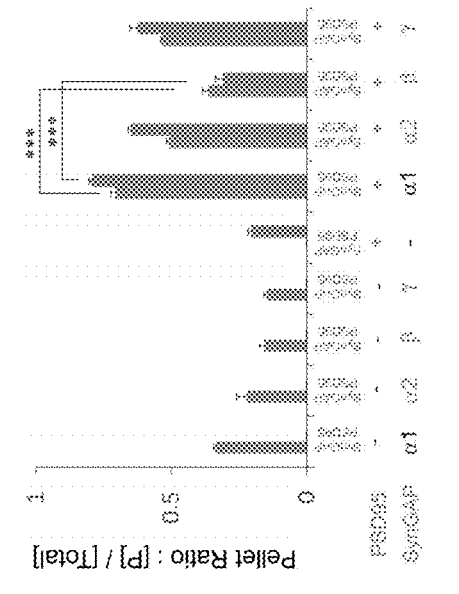
FIG. 2D
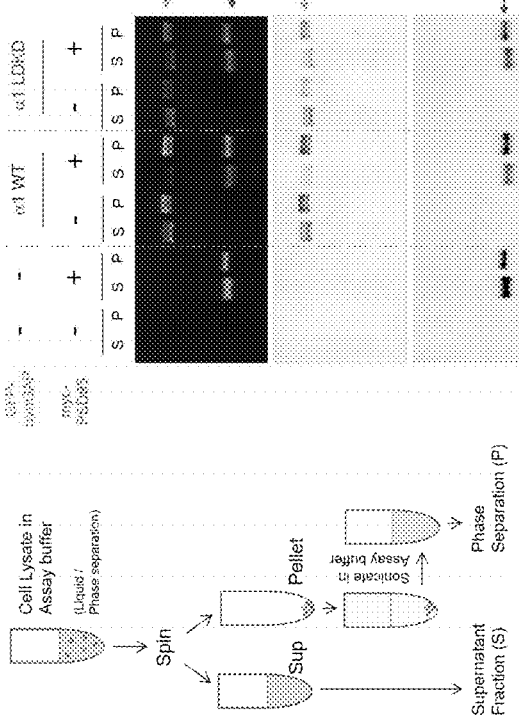
FIG. 2E
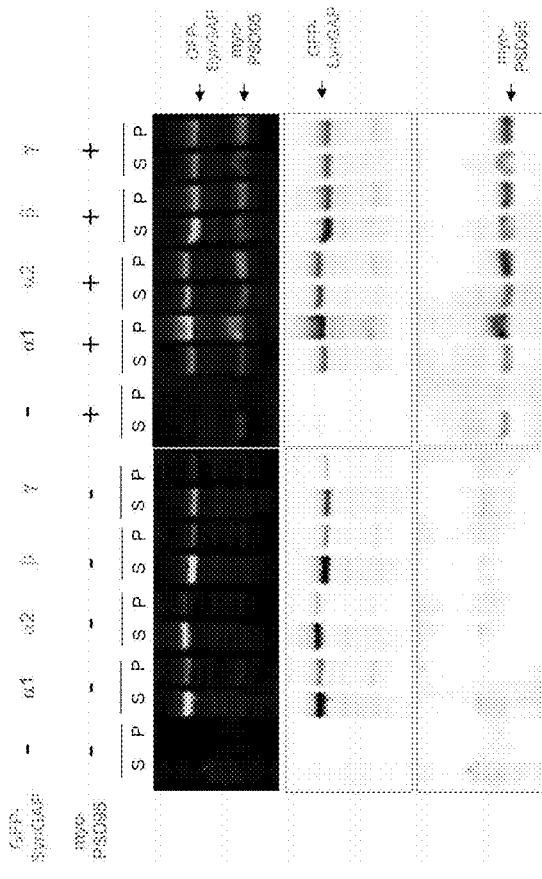

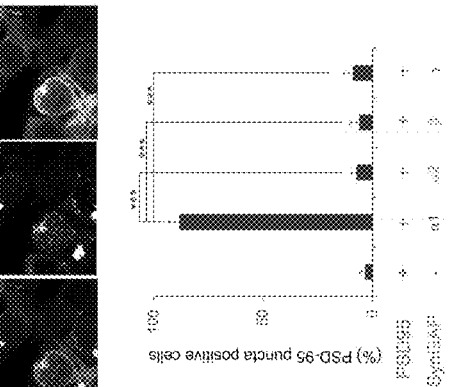
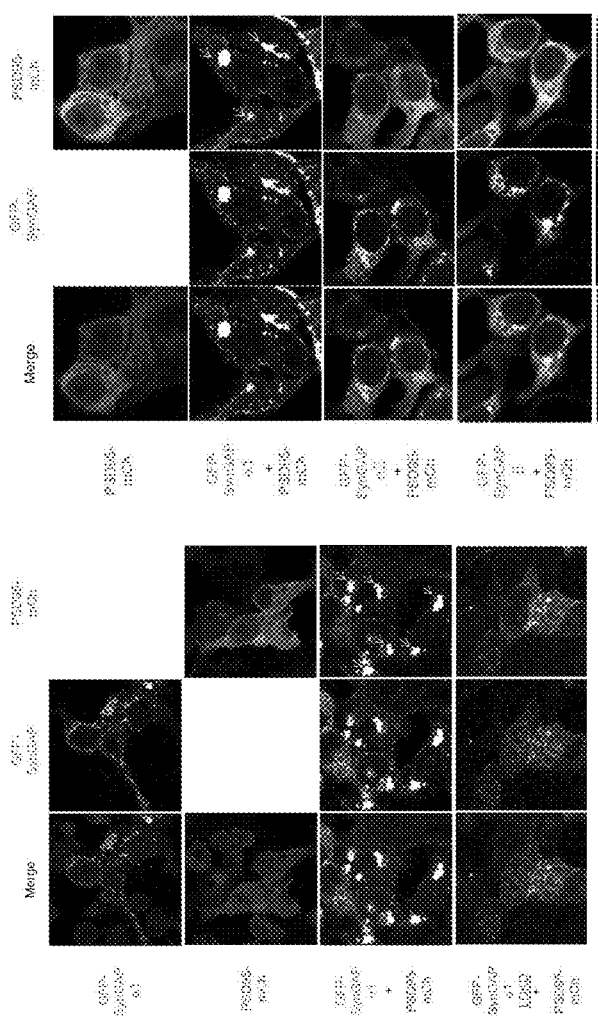
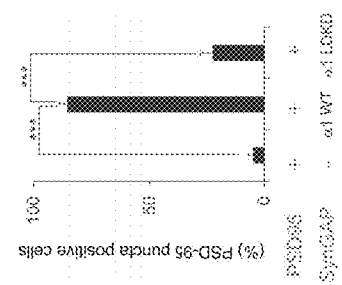
FIG. 2G
FIG. 2F

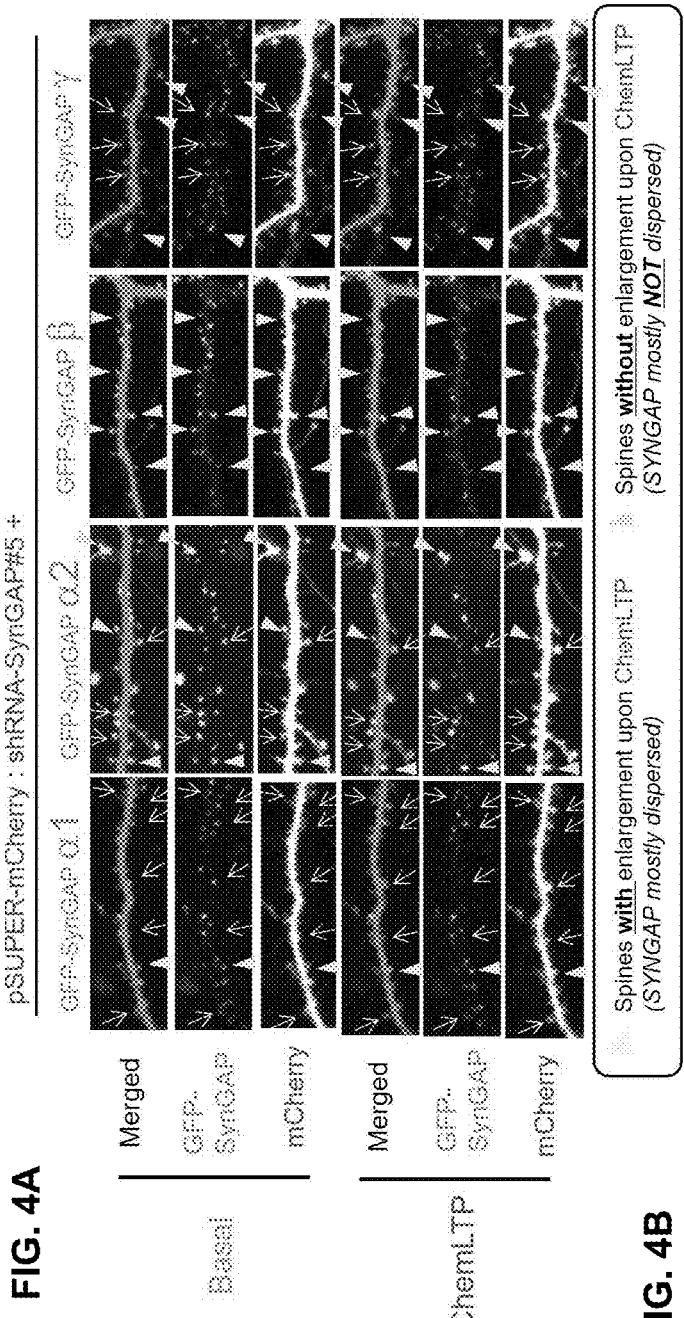
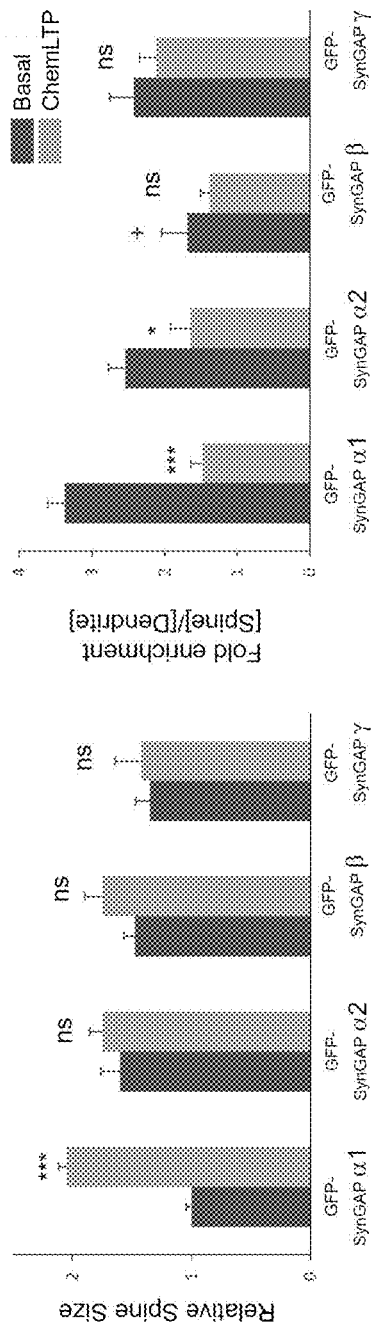
FIG. 4A
FIG. 4B

Structure of SYNGAP2

3 exons for database transcript (SYNGAP2-Short)

4 exons for novel SYNGAP2-Long transcript

Both annealing with Exon 16 and/or 17 of sense SYNGAP1

Sequence Screening in shRNA system → #4, 5 are effective

ASO #4, #5 (PS/PO chimera) Transfection Effectively Decreases SYNGAP2

(ASO#4) C*T*C* TTG AGA AGC CTT CCG *T*C*C SEQ ID NO: 14
(Scr#4) T*G*G* TCT CGC TCT GAC CTC *A*C*A SEQ ID NO: 18

(Scr#5) G*T*T* ATT GTT ACG TTC T *A*T*A SEQ ID NO: 461
(ASO#5) T*T*A* GTT TGA TTA CAT T *T*G*C SEQ ID NO: 15

* = Phosphorothioate(PS)

PS

SEQUENCE LISTING

<160> NUMBER OF SEQ ID NOS: 462

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctgcgtttc ccggtgatta a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtttcccggt gattaagtgt a                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aagctgcgtt tcccggtgat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acctgccaat gatgctcttg a                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggacggaagg cttctcaaga g                                              21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcaaatgtaa tcaaactaa                                                 19

```
<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gccagccatg gtatctcatt c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggatccctgc aaatgtaatc a                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgtgaggtca gagcgagacc a                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttaatcaccg ggaaacgcag c                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tacacttaat caccgggaaa c                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aatcaccggg aaacgcagct t                                              21
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcaagagcat cattggcagg t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctcttgagaa gccttccgtc c                                              21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttagtttgat tacatttgc                                                 19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gaatgagata ccatggctgg c                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgattacatt tgcagggatc c                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tggtctcgct ctgacctcac a                                              21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uuaaucaccg ggaaacgcag c                                              21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uacacuuaau caccgggaaa c                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aaucaccggg aaacgcagcu u                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ucaagagcau cauuggcagg u                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cucuugagaa gccuuccguc c                                              21

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uuaguuugau uacauuugc                                                 19

<210> SEQ ID NO 25

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 25
gaaugagaua ccauggcugg c                                              21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 26
ugauuacauu ugcagggauc c                                              21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 27
accagagcga gacuggagug u                                              21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
gtggaaatta caatgtcatt                                                20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
aattacaatg tcatttatct                                                20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
caatgtcatt tatcttctcc                                                20

<210> SEQ ID NO 31
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tcatttatct tctccgtgtc                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tatcttctcc gtgtcccatc                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tctccgtgtc ccatccccat                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtgtcccatc cccatccatc                                                   20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccatccccat ccatcccact                                                   20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cccatccatc ccactgtctt                                                   20

<210> SEQ ID NO 37
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 37
ccatcccact gtctttcgtg                                                        20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ccactgtctt tcgtgcactc                                                        20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gtctttcgtg cactcactac                                                        20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcgtgcactc actacaccag                                                        20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cactcactac accagccacc                                                        20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
actacaccag ccacctagcc                                                        20

<210> SEQ ID NO 43
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 43
ggctataggg gaggccactg                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
taggggaggc cactgctagg                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gaggccactg ctaggggact                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cactgctagg ggactggcat                                                    20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ctaggggact ggcatccagg                                                    20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aggggactgg catccaggcc                                                    20

<210> SEQ ID NO 49
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 49
ggcatccagg cccccttgaa                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccaggccccc ttgaagcgtc                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ccttgaagcg tctcaataag                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ttgaagcgtc tcaataagtc                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aatgacattg taatttccac                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agataaatga cattgtaatt                                               20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
ggagaagata aatgacattg                                                 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gacacggaga agataaatga                                                 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gatgggacac ggagaagata                                                 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
atggggatgg gacacggaga                                                 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gatggatggg gatgggacac                                                 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
agtgggatgg atggggatgg                                                 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 61
aagacagtgg gatggatggg                                                       20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cacgaaagac agtgggatgg                                                       20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gagtgcacga aagacagtgg                                                       20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gtagtgagtg cacgaaagac                                                       20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ctggtgtagt gagtgcacga                                                       20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ggtggctggt gtagtgagtg                                                       20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggctaggtgg ctggtgtagt                                            20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cagtggcctc ccctatagcc                                            20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cctagcagtg gcctccccta                                            20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
agtcccctag cagtggcctc                                            20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
atgccagtcc cctagcagtg                                            20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cctggatgcc agtcccctag                                            20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggcctggatg ccagtccoct                                               20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ttcaaggggg cctggatgcc                                               20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gacgcttcaa gggggcctgg                                               20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cttattgaga cgcttcaagg                                               20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gacttattga gacgcttcaa                                               20

<210> SEQ ID NO 78
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aaugacauug uaauuuccac                                               20

<210> SEQ ID NO 79
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79

```
agauaaauga cauuguaauu                                          20
```

<210> SEQ ID NO 80
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80

```
ggagaagaua aaugacauug                                          20
```

<210> SEQ ID NO 81
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81

```
gacacggaga agauaaauga                                          20
```

<210> SEQ ID NO 82
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82

```
gaugggacac ggagaagaua                                          20
```

<210> SEQ ID NO 83
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83

```
auggggaugg gacacggaga                                          20
```

<210> SEQ ID NO 84
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84

```
gauggauggg gaugggacac                                          20
```

<210> SEQ ID NO 85
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85

```
agugggaugg auggggaugg                                          20
```

<210> SEQ ID NO 86
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
aagacagugg gauggauggg                                                  20

<210> SEQ ID NO 87
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
cacgaaagac agugggaugg                                                  20

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
gagugcacga aagacagugg                                                  20

<210> SEQ ID NO 89
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
guagugagug cacgaaagac                                                  20

<210> SEQ ID NO 90
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
cugguguagu gagugcacga                                                  20

<210> SEQ ID NO 91
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
gguggcuggu guagugagug                                                  20

```
<210> SEQ ID NO 92
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ggcuaggugg cugguguagu                                                     20

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
caguggccuc cccuauagcc                                                     20

<210> SEQ ID NO 94
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ccuagcagug gccuccccua                                                     20

<210> SEQ ID NO 95
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
aguccccuag caguggccuc                                                     20

<210> SEQ ID NO 96
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
augccagucc ccuagcagug                                                     20

<210> SEQ ID NO 97
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ccuggaugcc aguccccuag                                                     20
```

```
<210> SEQ ID NO 98
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ggccuggaug ccaguccccu                                                    20

<210> SEQ ID NO 99
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uucaaggggg ccuggaugcc                                                    20

<210> SEQ ID NO 100
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gacgcuucaa gggggccugg                                                    20

<210> SEQ ID NO 101
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
cuuauugaga cgcuucaagg                                                    20

<210> SEQ ID NO 102
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gacuuauuga gacgcuucaa                                                    20

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ccactgcagc tcctcatcag gtaatt                                             26

<210> SEQ ID NO 104
```

<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
ctgcagctcc tcatcaggta att                                              23

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
cagctcctca tcaggtaatt                                                  20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
ctcctcatca ggtaattctc                                                  20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
catcaggtaa ttctcctggt                                                  20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
ggtaattctc ctggttccgc                                                  20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
ttctcctggt tccgctttgg                                                  20

<210> SEQ ID NO 110
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ctggttccgc tttggccacg                                              20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tccgctttgg ccacgggcgg                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tttggccacg ggcggaggac                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ccacgggcgg aggacacagg                                              20

<210> SEQ ID NO 114
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
aattacctga tgaggagctg cagtgg                                       26

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
aattacctga tgaggagctg cag                                          23

<210> SEQ ID NO 116
<211> LENGTH: 20
<212> TYPE: DNA
```

<213> ORGANISM: Artificial Sequence
<220> FEATURE:
<223> OTHER INFORMATION: Description of Artificial Sequence: Synthetic
    oligonucleotide

<400> SEQUENCE: 116
aattacctga tgaggagctg                                              20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 117
gagaattacc tgatgaggag                                              20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 118
accaggagaa ttacctgatg                                              20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 119
gcggaaccag gagaattacc                                              20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 120
ccaaagcgga accaggagaa                                              20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 121
cgtggccaaa gcggaaccag                                              20

<210> SEQ ID NO 122
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 122
ccgcccgtgg ccaaagcgga                                                     20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gtcctccgcc cgtggccaaa                                                     20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cctgtgtcct ccgcccgtgg                                                     20

<210> SEQ ID NO 125
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
aauuaccuga ugaggagcug cagugg                                              26

<210> SEQ ID NO 126
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
aauuaccuga ugaggagcug cag                                                 23

<210> SEQ ID NO 127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
aauuaccuga ugaggagcug                                                     20

<210> SEQ ID NO 128
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 128
gagaauuacc ugaugaggag                                              20

<210> SEQ ID NO 129
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
accaggagaa uuaccugaug                                              20

<210> SEQ ID NO 130
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
gcggaaccag gagaauuacc                                              20

<210> SEQ ID NO 131
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
ccaaagcgga accaggagaa                                              20

<210> SEQ ID NO 132
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
cguggccaaa gcggaaccag                                              20

<210> SEQ ID NO 133
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ccgcccgugg ccaaagcgga                                              20

<210> SEQ ID NO 134
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 134
guccuccgcc cguggccaaa                                                  20

<210> SEQ ID NO 135
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ccuguguccu ccgcccgugg                                                  20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
taaccccact gaagcccgtc                                                  20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
cgctcaggtg gaaattacaa                                                  20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ctcgacgctc aggtggaaat                                                  20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ggctgctcga cgctcaggtg                                                  20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gaagaggctg ctcgacgctc                                        20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cccaagaaga ggctgctcga                                        20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cagaacccaa gaagaggctg                                        20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gctgccagaa cccaagaaga                                        20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gagccgctgc cagaacccaa                                        20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tggctgagcc gctgccagaa                                        20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
cgccatggct gagccgctgc                                      20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
caccccgcca tggctgagcc                                      20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gggaccaccc cgccatggct                                      20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gcgccgggac caccccgcca                                      20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gagctgcgcc gggaccaccc                                      20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
aggaggagct gcgccgggac                                      20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ggtggaggag gagctgcgcc                                               20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
atgctggtgg aggaggagct                                               20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
actgaagccc gtcccttcag                                               20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
aaccccactg aagcccgtcc                                               20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cactaacccc actgaagccc                                               20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
cccgccacta accccactga                                               20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gcctgtgccc gccactaacc                                         20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tgagcctgtg cccgccacta                                         20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ggctctgagc ctgtgcccgc                                         20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gggcaggctc tgagcctgtg                                         20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tccatgggca ggctctgagc                                         20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gacgggcttc agtggggtta                                         20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ttgtaatttc cacctgagcg                                         20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
atttccacct gagcgtcgag                                               20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cacctgagcg tcgagcagcc                                               20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gagcgtcgag cagcctcttc                                               20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tcgagcagcc tcttcttggg                                               20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
cagcctcttc ttgggttctg                                               20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tcttcttggg ttctggcagc                                               20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ttgggttctg gcagcggctc                                           20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ttctggcagc ggctcagcca                                           20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gcagcggctc agccatggcg                                           20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ggctcagcca tggcggggtg                                           20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
agccatggcg gggtggtccc                                           20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tggcggggtg gtcccggcgc                                           20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gggtggtccc ggcgcagctc                                              20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gtcccggcgc agctcctcct                                              20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ggcgcagctc ctcctccacc                                              20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
agctcctcct ccaccagcat                                              20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ctgaagggac gggcttcagt                                              20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ggacgggctt cagtggggtt                                              20

<210> SEQ ID NO 183

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gggcttcagt ggggttagtg                                                    20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tcagtggggt tagtggcggg                                                    20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggttagtggc gggcacaggc                                                    20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tagtggcggg cacaggctca                                                    20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gcgggcacag gctcagagcc                                                    20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cacaggctca gagcctgccc                                                    20

<210> SEQ ID NO 189
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
gctcagagcc tgcccatgga                                          20

<210> SEQ ID NO 190
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
gacgggcuuc agugggguua                                          20

<210> SEQ ID NO 191
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
uuguaauuuc caccugagcg                                          20

<210> SEQ ID NO 192
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
auuuccaccu gagcgucgag                                          20

<210> SEQ ID NO 193
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
caccugagcg ucgagcagcc                                          20

<210> SEQ ID NO 194
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
gagcgucgag cagccucuuc                                          20

<210> SEQ ID NO 195
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 195
ucgagcagcc ucuucuuggg                                                20

<210> SEQ ID NO 196
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
cagccucuuc uuggguucug                                                20

<210> SEQ ID NO 197
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
ucuucuuggg uucuggcagc                                                20

<210> SEQ ID NO 198
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
uuggguucug gcagcggcuc                                                20

<210> SEQ ID NO 199
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uucuggcagc ggcucagcca                                                20

<210> SEQ ID NO 200
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gcagcggcuc agccauggcg                                                20

<210> SEQ ID NO 201
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 201
ggcucagcca uggcggggug                                                     20

<210> SEQ ID NO 202
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
agccauggcg ggugguccc                                                      20

<210> SEQ ID NO 203
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uggcggggug gucccggcgc                                                     20

<210> SEQ ID NO 204
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204 ggugguccc ggcgcagcuc                                                      20

<210> SEQ ID NO 205
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
gucccggcgc agcuccuccu                                                     20

<210> SEQ ID NO 206
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ggcgcagcuc cuccuccacc                                                     20

<210> SEQ ID NO 207
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 207
agcuccuccu ccaccagcau                                                   20

<210> SEQ ID NO 208
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
cugaagggac gggcuucagu                                                   20

<210> SEQ ID NO 209
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
ggacgggcuu cagugggguu                                                   20

<210> SEQ ID NO 210
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
gggcuucagu gggguuagug                                                   20

<210> SEQ ID NO 211
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211 ucagugggguuaguggcggg                                                    20

<210> SEQ ID NO 212
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
gguuaguggc gggcacaggc                                                   20

<210> SEQ ID NO 213
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 213
uaguggcggg cacaggcuca                                      20

<210> SEQ ID NO 214
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
gcgggcacag gcucagagcc                                      20

<210> SEQ ID NO 215
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
cacaggcuca gagccugccc                                      20

<210> SEQ ID NO 216
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
gcucagagcc ugcccaugga                                      20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
cttcttcaag cagcctccca                                      20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tccctggaag ctgagggtct                                      20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
cctggaagct gagggtctct    20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ctctccccct ccatttctct    20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
cccctccatt tctctctccc    20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ccatttctct ctccctaatc    20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tctctctccc taatctgtct    20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ctccctaatc tgtctgttcc    20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
taatctgtct gttccctctg                                               20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tgtctgttcc ctctgccatg                                               20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gttccctctg ccatggcccc                                               20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ctctgccatg gccccttct                                                20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ccatggcccc cttcttcaag                                               20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230 gccccttct tcaagcagcc                                                20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tcaagcagcc tcccatcttg                                              20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
cagcctccca tcttgctcct                                              20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tcccatcttg ctcctgcggt                                              20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tcttgctcct gcggtccctc                                              20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ctcctgcggt ccctccttcc                                              20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gcggtccctc cttccctgtc                                              20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ccctccttcc ctgtctctct                                          20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
cttccctgtc tctctcaccc                                          20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ctgtctctct cacccctgtt                                          20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tctctcaccc ctgtttccac                                          20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cacccctgtt tccacaccct                                          20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ctgtttccac accctcacct                                          20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tccacaccct cacctcctac                                          20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
accctcacct cctaccaccc                                               20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
cacctcctac cacccccctc                                               20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
cctaccaccc ccctcagcat                                               20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
cacccccctc agcatgttcc                                               20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ccctcagcat gttccctgga                                               20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
agcatgttcc ctggaagctg                                               20

```
<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gttccctgga agctgagggt                                              20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ctggaagctg agggtctctg                                              20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
agctgagggt ctctggggct                                              20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
agggtctctg gggctcagtc                                              20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ctctggggct cagtcccggt                                              20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
gggctcagtc ccggtctctc                                              20
```

```
<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
cagtcccggt ctctctcttt                                                     20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
ccggtctctc tctttctctc                                                     20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ctctctcttt ctctctctct                                                     20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tctttctctc tctctctctc                                                     20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ctctctctct ctctctgtct                                                     20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tctctctctc tgtctccccg                                                     20

<210> SEQ ID NO 262
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
ctctctgtct ccccgaccct                                                 20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tgtctccccg acccttcccc                                                 20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ccccgaccct tcccccagc                                                  20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
acccttcccc ccagcgtgtt                                                 20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266 tcccccagc gtgttcccga                                                  20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ccagcgtgtt cccgagggag                                                 20

<210> SEQ ID NO 268
<211> LENGTH: 20
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gtgttcccga gggagctgaa                                              20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
cccgagggag ctgaaggagg                                              20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gggagctgaa ggaggtgttt                                              20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ctgaaggagg tgtttgcttc                                              20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ggaggtgttt gcttcgtggc                                              20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
tgtttgcttc gtggcggctg                                              20

<210> SEQ ID NO 274
<211> LENGTH: 20
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 274
gcttcgtggc ggctgcgctg                                              20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gtggcggctg cgctgcgcag                                              20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
ggctgcgctg cgcagagcga                                              20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
cgctgcgcag agcgaggccg                                              20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
cgcagagcga ggccgggagg                                              20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
agcgaggccg ggaggacatc                                              20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 280
ggccgggagg acatcgcaga                                                     20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 281
ggaggacatc gcagacaggc                                                     20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 282
acatcgcaga caggcttatc                                                     20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 283
gcagacaggc ttatcagcgc                                                     20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 284
caggcttatc agcgcctcac                                                     20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 285
ttatcagcgc ctcactcttc                                                     20

<210> SEQ ID NO 286
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 286
agcgcctcac tcttcctgcg                                                  20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ctcactcttc ctgcgcttcc                                                  20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tcttcctgcg cttcctctgc                                                  20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ctgcgcttcc tctgcccagc                                                  20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
cttcctctgc ccagcgatta                                                  20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
tctgcccagc gattatgtcg                                                  20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 292
ccagcgatta tgtcgcccag                                               20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
gattatgtcg cccagtctct                                               20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
tgtcgcccag tctctttggg                                               20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tgggaggctg cttgaagaag                                               20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
agaccctcag cttccaggga                                               20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
agagaccctc agcttccagg                                               20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 298
agagaaatgg aggggggagag                                          20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
gggagagaga aatggagggg                                           20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gattagggag agagaaatgg                                           20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
agacagatta gggagagaga                                           20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
ggaacagaca gattagggag                                           20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
cagagggaac agacagatta                                           20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 304
catggcagag ggaacagaca                                                    20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
ggggccatgg cagagggaac                                                    20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306 agaaggggc catggcagag                                                     20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
cttgaagaag ggggccatgg                                                    20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ggctgcttga agaaggggc                                                     20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
caagatggga ggctgcttga                                                    20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
```
aggagcaaga tgggaggctg                                              20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
accgcaggag caagatggga                                              20

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gagggaccgc aggagcaaga                                              20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ggaaggaggg accgcaggag                                              20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gacagggaag gagggaccgc                                              20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
agagagacag ggaaggaggg                                              20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
gggtgagaga gacagggaag                                          20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
aacaggggtg agagagacag                                          20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gtggaaacag gggtgagaga                                          20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
agggtgtgga aacaggggtg                                          20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
aggtgagggt gtggaaacag                                          20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
gtaggaggtg agggtgtgga                                          20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gggtggtagg aggtgagggt                                          20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323 gagggggtg gtaggaggtg                                                    20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
atgctgaggg gggtggtagg                                                   20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ggaacatgct gagggggtg                                                    20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
tccagggaac atgctgaggg                                                   20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
cagcttccag ggaacatgct                                                   20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
accctcagct tccagggaac                                                   20

```
<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
cagagaccct cagcttccag                                                  20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
agccccagag accctcagct                                                  20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gactgagccc cagagaccct                                                  20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
accgggactg agccccagag                                                  20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gagagaccgg gactgagccc                                                  20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
aaagagagag accgggactg                                                  20
```

```
<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gagagaaaga gagagaccgg                                               20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
agagagagag aaagagagag                                               20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
gagagagaga gagagaaaga                                               20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
agacagagag agagagagag                                               20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
cggggagaca gagagagaga                                               20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
agggtcgggg agacagagag                                               20

<210> SEQ ID NO 341
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
ggggaagggt cggggagaca                                                 20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gctgggggga agggtcgggg                                                 20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
aacacgctgg ggggaagggt                                                 20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
tcgggaacac gctgggggga                                                 20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
ctccctcggg aacacgctgg                                                 20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
ttcagctccc tcgggaacac                                                 20

<210> SEQ ID NO 347
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
cctccttcag ctccctcggg                                               20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
aaacacctcc ttcagctccc                                               20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gaagcaaaca cctccttcag                                               20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
gccacgaagc aaacacctcc                                               20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
cagccgccac gaagcaaaca                                               20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
cagcgcagcc gccacgaagc                                               20

<210> SEQ ID NO 353
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 353
ctgcgcagcg cagccgccac                                                 20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
tcgctctgcg cagcgcagcc                                                 20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
cggcctcgct ctgcgcagcg                                                 20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
cctcccggcc tcgctctgcg                                                 20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
gatgtcctcc cggcctcgct                                                 20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
tctgcgatgt cctcccggcc                                                 20

<210> SEQ ID NO 359
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 359
gcctgtctgc gatgtcctcc                                                    20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
gataagcctg tctgcgatgt                                                    20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
gcgctgataa gcctgtctgc                                                    20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gtgaggcgct gataagcctg                                                    20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
gaagagtgag gcgctgataa                                                    20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
cgcaggaaga gtgaggcgct                                                    20

<210> SEQ ID NO 365
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 365
ggaagcgcag gaagagtgag                                              20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
gcagaggaag cgcaggaaga                                              20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
gctgggcaga ggaagcgcag                                              20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
taatcgctgg gcagaggaag                                              20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
cgacataatc gctgggcaga                                              20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
ctgggcgaca taatcgctgg                                              20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 371
agagactggg cgacataatc                                               20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
cccaaagaga ctgggcgaca                                               20

<210> SEQ ID NO 373
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
ugggaggcug cuugaagaag                                               20

<210> SEQ ID NO 374
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
agacccucag cuuccaggga                                               20

<210> SEQ ID NO 375
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
agagacccuc agcuuccagg                                               20

<210> SEQ ID NO 376
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
agagaaaugg aggggagag                                                20

<210> SEQ ID NO 377
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
gggagagaga aauggagggg					20

<210> SEQ ID NO 378
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
gauuagggag agagaaaugg					20

<210> SEQ ID NO 379
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
agacagauua gggagagaga					20

<210> SEQ ID NO 380
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
ggaacagaca gauuagggag					20

<210> SEQ ID NO 381
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
cagagggaac agacagauua					20

<210> SEQ ID NO 382
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
cauggcagag ggaacagaca					20

<210> SEQ ID NO 383
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 383
ggggccaugg cagagggaac                                                    20

<210> SEQ ID NO 384
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384 agaaggggggc cauggcagag                                                   20

<210> SEQ ID NO 385
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
cuugaagaag ggggccaugg                                                    20

<210> SEQ ID NO 386
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
ggcugcuuga agaaggggggc                                                   20

<210> SEQ ID NO 387
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
caagauggga ggcugcuuga                                                    20

<210> SEQ ID NO 388
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
aggagcaaga ugggaggcug                                                    20

<210> SEQ ID NO 389
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
```
accgcaggag caagaugggga 20

<210> SEQ ID NO 390
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
gagggaccgc aggagcaaga 20

<210> SEQ ID NO 391
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
ggaaggaggg accgcaggag 20

<210> SEQ ID NO 392
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
gacagggaag gagggaccgc 20

<210> SEQ ID NO 393
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
agagagacag ggaaggaggg 20

<210> SEQ ID NO 394
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
gggugagaga gacagggaag 20

<210> SEQ ID NO 395
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
aacaggggug agagagacag					20

<210> SEQ ID NO 396
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
guggaaacag gggugagaga					20

<210> SEQ ID NO 397
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
agggugugga aacaggggug					20

<210> SEQ ID NO 398
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
aggugagggu guggaaacag					20

<210> SEQ ID NO 399
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
guaggaggug aggugugga					20

<210> SEQ ID NO 400
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
gggugguagg aggugagggu					20

<210> SEQ ID NO 401
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401 gagggggug guaggaggug					20

<210> SEQ ID NO 402
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
augcugaggg gggugguagg                                               20

<210> SEQ ID NO 403
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
ggaacaugcu gagggggggug                                              20

<210> SEQ ID NO 404
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
uccagggaac augcugaggg                                               20

<210> SEQ ID NO 405
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
cagcuuccag ggaacaugcu                                               20

<210> SEQ ID NO 406
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
acccucagcu uccagggaac                                               20

<210> SEQ ID NO 407
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
cagagacccu cagcuuccag                                               20

<210> SEQ ID NO 408
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
agccccagag acccucagcu                                              20

<210> SEQ ID NO 409
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
gacugagccc cagagacccu                                              20

<210> SEQ ID NO 410
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
accgggacug agccccagag                                              20

<210> SEQ ID NO 411
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
gagagaccgg gacugagccc                                              20

<210> SEQ ID NO 412
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
aaagagagag accgggacug                                              20

<210> SEQ ID NO 413
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
gagagaaaga gagagaccgg                                              20

```
<210> SEQ ID NO 414
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
agagagagag aaagagagag                                                 20

<210> SEQ ID NO 415
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
gagagagaga gagagaaaga                                                 20

<210> SEQ ID NO 416
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
agacagagag agagagagag                                                 20

<210> SEQ ID NO 417
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
cggggagaca gagagagaga                                                 20

<210> SEQ ID NO 418
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
agggucgggg agacagagag                                                 20

<210> SEQ ID NO 419
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
ggggaagggu cggggagaca                                                 20

<210> SEQ ID NO 420
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
gcugggggga agggucgggg                                              20

<210> SEQ ID NO 421
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
aacacgcugg ggggaagggu                                              20

<210> SEQ ID NO 422
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
ucgggaacac gcugggggga                                              20

<210> SEQ ID NO 423
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
cucccucggg aacacgcugg                                              20

<210> SEQ ID NO 424
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
uucagcuccc ucgggaacac                                              20

<210> SEQ ID NO 425
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
ccuccuucag cucccucggg                                              20

<210> SEQ ID NO 426
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
aaacaccucc uucagcuccc                                              20

<210> SEQ ID NO 427
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
gaagcaaaca ccuccuucag                                              20

<210> SEQ ID NO 428
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
gccacgaagc aaacaccucc                                              20

<210> SEQ ID NO 429
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
cagccgccac gaagcaaaca                                              20

<210> SEQ ID NO 430
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
cagcgcagcc gccacgaagc                                              20

<210> SEQ ID NO 431
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
cugcgcagcg cagccgccac                                              20

<210> SEQ ID NO 432
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 432
ucgcucugcg cagcgcagcc                                              20

<210> SEQ ID NO 433
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
cggccucgcu cugcgcagcg                                              20

<210> SEQ ID NO 434
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
ccucccggcc ucgcucugcg                                              20

<210> SEQ ID NO 435
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
gauguccucc cggccucgcu                                              20

<210> SEQ ID NO 436
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
ucugcgaugu ccucccggcc                                              20

<210> SEQ ID NO 437
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
gccugucugc gauguccucc                                              20

<210> SEQ ID NO 438
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 438
gauaagccug ucugcgaugu                                              20

<210> SEQ ID NO 439
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
gcgcugauaa gccugucugc                                              20

<210> SEQ ID NO 440
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
gugaggcgcu gauaagccug                                              20

<210> SEQ ID NO 441
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
gaagagugag gcgcugauaa                                              20

<210> SEQ ID NO 442
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
cgcaggaaga gugaggcgcu                                              20

<210> SEQ ID NO 443
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
ggaagcgcag gaagagugag                                              20

<210> SEQ ID NO 444
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 444
gcagaggaag cgcaggaaga                                                    20

<210> SEQ ID NO 445
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
gcugggcaga ggaagcgcag                                                    20

<210> SEQ ID NO 446
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
uaaucgcugg gcagaggaag                                                    20

<210> SEQ ID NO 447
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
cgacauaauc gcugggcaga                                                    20

<210> SEQ ID NO 448
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
cugggcgaca uaaucgcugg                                                    20

<210> SEQ ID NO 449
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
agagacuggg cgacauaauc                                                    20

<210> SEQ ID NO 450
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 450
cccaaagaga cugggcgaca                                                   20

<210> SEQ ID NO 451
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
ccagcattat gaaag                                                        15

<210> SEQ ID NO 452
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
tcactttcat aatgctgg                                                     18

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453
gcgactatac gcgcaauaug                                                   20

<210> SEQ ID NO 454
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454 ucacuucau aaugcugg                                                      18

<210> SEQ ID NO 455
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
gcgacuauac gcgcaauaug                                                   20

<210> SEQ ID NO 456
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Arg Leu Met Leu Val Glu Glu Glu Leu Arg Arg Asp His Pro Ala Met
1               5                   10                  15

Ala Glu Pro Leu Pro Glu Pro Lys Lys Arg Leu Leu Asp Ala Gln
            20                  25                  30

<210> SEQ ID NO 457
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Ser Pro Ser Leu Gln Ala Asp Ala Gly Gly Gly Gly Ala Ala Pro Gly
1               5                   10                  15

Pro Pro Arg His Gly
            20

<210> SEQ ID NO 458
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Leu Leu Ile Arg
1

<210> SEQ ID NO 459
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Arg Gly Ser Phe Pro Pro Trp Val Gln Gln Thr Arg Val
1               5                   10

<210> SEQ ID NO 460
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Glu Arg Gln Leu Pro Pro Leu Gly Pro Thr Asn Pro Arg Val Thr Leu
1               5                   10                  15

Ala Pro Pro Trp Asn Gly Leu Ala Pro Ala Pro Pro Pro Pro
            20                  25                  30

Arg Leu Gln Ile Thr Glu Asn Gly Glu Phe Arg Asn Thr Ala Asp His
                35                  40                  45

<210> SEQ ID NO 461

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
gttattgtta cgttctata                                            19

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
actgacttga ccggatattg t                                         21
```

MODULATING SYNGAP

CROSS-REFERENCE TO RELATED APPLICATIONS

This application claims priority to U.S. Provisional Application Ser. No. 62/968,663, filed on Jan. 31, 2020, and U.S. Provisional Application Ser. No. 62/929,525, filed on Nov. 1, 2019, the entire contents of which are hereby incorporated by reference.

FEDERALLY SPONSORED RESEARCH OR DEVELOPMENT

This invention was made with government support under Grant No. MH112151, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 26, 2021, is named 44807-0344001_SL.txt and is 110,244 bytes in size.

TECHNICAL FIELD

The present disclosure relates to SYNGAP-associated neurological disorders and methods of treating SYNGAP disorders.

BACKGROUND

SynGAP1 is a GTPase-activating protein (GAP) that is highly enriched in dendritic spines of excitatory neurons. SynGAP is classified into Ras- and Rap-GTPase activating proteins and facilitate hydrolysis of small G protein-bound GTP (Active) to GDP (Inactive), thus negatively regulates these small G proteins. SynGAP1 is encoded by the SYNGAP1 gene, and has 3 distinct transcriptional start sites and alternatively spliced to generate 4 distinct C-terminal isoforms designated as SYNGAP1 α1, SYNGAP1 α2, SYNGAP1 β, and SYNGAP1 γ, respectively. Recently many human genetic studies have suggested that mutations in the human SYNGAP1 gene are linked to intellectual disability (ID), autism spectrum disorders (ASD), and other neurodevelopmental disorders (NDD), with high rates of epilepsy as well as schizophrenia. The ID-associated SYNGAP1 mutations cause MRD5-categorized ID.

A myriad of evidence have suggested that mutations in the SYNGAP1 gene have been linked to intellectual disability (ID), autism spectrum disorders (ASD), and other neurodevelopmental disorders (NDD), with high rates of comorbid epilepsy, seizures, and acquired microcephaly (Berryer et al., 2013; Berryer et al., 2012; Carvill et al., 2013; Cook, 2011; Hamdan et al., 2011; Hamdan et al., 2009; Parker et al., 2015; Rauch et al., 2012; Tan et al., 2015; UK-DDD-study, 2015; Vissers et al., 2010; Writzl and Knegt, 2013). The ID associated SynGAP1 mutations cause MRD5-categorized ID (OMIM #612621). Almost all reported cases of ID/ASD are de novo mutations within exons or splice sites. MRD5 is characterized by moderate to severe intellectual disability with delayed psychomotor development apparent in the first years of life. SYNGAP1 is the 4th most highly prevalent NDD-associated gene, and mutations in SYNGAP1 account for ~0.7% of all NDD cases (UK-DDD-study, 2015). Some key pathophysiological symptoms of ID and ASD patients have been recapitulated in SYNGAP1 heterozygous (+/−) knockout mice (Clement et al., 2012). SYNGAP1 heterozygous mice exhibit epileptic circuit activity, altered synaptic transmission, and severe working memory deficits (Clement et al., 2012; Guo et al., 2009). Some of SYNGAP1 missense mutations in MRD5 also caused drastic SynGAP protein instability (Berryer et al., 2013). These data suggest that SYNGAP1 haploinsufficiency is likely pathogenic in ID/ASD-associated SYNGAP1 cases. Although SYNGAP1 haploinsufficiency likely affects all SynGAP1 isoforms equally, only the α1 isoform has been rigorously characterized in this context to date, and only few functional studies of non-α1 SynGAP1 isoforms are currently available in the context of neuronal functions and synaptic physiology (Li et al., 2001; McMahon et al., 2012). Further, therapeutic applications to regulate SynGAP expression are needed.

SUMMARY

The present disclosure features compositions and methods that regulate SynGAP (Synaptic GTPase Activating Protein); an excitatory synapse protein that has been found to bind synaptic proteins and modulate signal transduction. In one aspect, the disclosure provides methods of detecting and methods of treating subjects in need thereof with agents to regulate expression of a SynGAP1 and mRNA isoforms of SynGAP1 and/or SynGAP2 and mRNA isoforms of SynGAP2.

Disclosed herein is a method of treating a SynGAP-associated neurodevelopmental disorder in a subject in need thereof, the method comprising administering an effective amount of an agent, wherein administering the agent modulates expression of one or more isoforms SynGAP1 and/or SynGAP2.

Also disclosed herein is a method of treating a SynGAP-associated neurodevelopmental disorder in a subject comprising (a) diagnosing the subject as having the SynGAP-associated neurodevelopmental disorder when the amount of one or more isoforms of SynGAP1 and/or SynGAP2 is dysregulated compared the amount of one or more isoforms of SynGAP1 in a reference sample; and (b) administering to a subject identified or diagnosed as having the SynGAP-associated neurodevelopmental disorder a therapeutically effective amount of an agent, wherein administering the agent modulates expression of one or more isoforms of SynGAP.

Also disclosed herein is a method of treating a SynGAP-associated neurodevelopmental disorder in a subject comprising (a) obtaining a sample from a subject; (b) assaying expression of one or more isoforms of SynGAP1 in the sample; (c) diagnosing the subject as having the SynGAP-associated neurodevelopmental disorder when the amount of one or more isoforms of SynGAP1 is dysregulated compared the amount of one or more isoforms of SynGAP1 in a reference sample; (d) administering to a subject identified or diagnosed as having the neurodevelopmental disorder a therapeutically effective amount of an agent, wherein administering the agent modulates expression of one or more isoforms of SynGAP1.

Also disclosed herein is a method of modulating SynGAP1 in a subject comprising: (a) obtaining a sample from the subject; (b) assaying expression of one or more isoforms of SynGAP1 in the sample; (c) administering to the subject an effective amount of a composition that modulates expression of one or more isoforms of SynGAP1.

Also disclosed herein is a method of monitoring expression of SynGAP1 in a subject, the method comprising (a) obtaining a sample from the subject; (b) assaying the level of one or more isoforms of SynGAP1 in the sample at an initial time point and a subsequent time point; and (c) administering to the subject a prophylactic effective amount of a composition that modulates expression of one or more isoforms of SynGAP1.

In some aspects, the one or more isoforms of SynGAP comprise SynGAP1 α1, SynGAP1 α2, SynGAP1 β, SynGAP1 γ, or any combination thereof. In some aspects, the one or more isoforms of SynGAP1 comprises SynGAP1 α1. In some aspects, the one or more isoforms of SynGAP1 comprises SynGAP1 α2. In some aspects, the one or more isoforms of SynGAP1 comprises SynGAP1 β. In some aspects, the one or more isoforms of SynGAP1 comprises SynGAP1 γ. In some aspects, the SynGAP-associated neurodevelopmental disorder comprises an intellectual disability (ID), autism spectrum disorders (ASD), epilepsy, or schizophrenia.

In some aspects, the sample is a cell line, tissue, or blood. In some aspects, the sample is neurological tissue or neurological fluid. In some aspects, the sample is hippocampal cells. In some aspects, the reference sample is from a subject that does not exhibit a SynGAP-associated neurodevelopmental disorder.

In some aspects, the expression of the one or more isoforms of SynGAP1 is increased after administering of the agent. In some aspects, the expression of the one or more isoforms of SynGAP1 is decreased after administering of the agent.

In some aspects, the subject is a mammal. In some aspects, the subject is a human. In some aspects, the subject is a mouse. In some aspects, the sample in the subject has aberrant expression of Ras, Rap1, Rac1, or any combination thereof. In some aspects, the sample in the subject has increased expression of Ras, Rap1, Rac1, or any combination thereof. In some aspects, the sample in the subject has decreased expression of Ras, Rap1, Rac1, or any combination thereof. In some aspects, the agent comprises a nucleic acid, a protein, a small molecule, a biologic, or any combination thereof.

In some aspects, the nucleic acid is an antisense oligonucleotide (ASO). In some aspects, the ASO targets SynGAP2. In some aspects, administering the ASO increases expression of SynGAP1 protein. In some aspects, administering the ASO increases expression of one or more isoforms of SynGAP1. In some aspects, the ASO comprises one or more chemical modifications. In some aspects, the one or more chemical modifications is a modification by phosphorothioates. In some aspects, the one or more chemical modifications is a 2'-O-methyl oligonucleotide.

In some aspects, the ASO comprises SEQ ID NO:18 (also referred herein to as ASO-#4). In some aspects, the ASO comprises SEQ ID NO:15 (also referred herein to as ASO-#5). In some aspects, the ASO comprises SEQ ID NO:17 (also referred herein to as ASO-#7). In some aspects, the ASO consists of SEQ ID NO:18. In some aspects, the ASO consists of SEQ ID NO:15. In some aspects, the ASO consists of SEQ ID NO:17.

In some aspects, the administering is via intracerebral, intraventricular, intracerebroventricular, intrathecal, intracisternal, intraspinal, or peri-spinal routes. In some aspects, the administering comprises using an intracranial or intravertebral needle or catheter. In some aspects, the administering is via oral administration, intravenous (iv) administration, intramuscular (im) administration, subcutaneous (sc) administration, or trans-dermal administration.

In some aspects, disclosed herein is a pharmaceutically acceptable composition comprising an agent, wherein the agent is capable of increasing the expression of SynGAP1; and an excipient. In some aspects, the agent comprises a nucleic acid, a protein, a small molecule, a biologic, or any combination thereof. In some aspects, the agent is an antisense oligonucleotide (ASO). In some aspects, the ASO targets SynGAP2. In some aspects, administering the ASO increases expression of SynGAP1 protein. In some aspects, administering the ASO increases expression of one or more isoforms of SynGAP1. In some aspects, the ASO comprises one or more chemical modifications. In some aspects, the one or more chemical modifications is a modification by phosphorothioates. In some aspects, the one or more chemical modifications is a 2'-O-methyl oligonucleotide. In some aspects, the ASO comprises SEQ ID NO:18. In some aspects, the ASO comprises SEQ ID NO:15. In some aspects, the ASO comprises SEQ ID NO:17. In some aspects, the ASO consists of SEQ ID NO:18. In some aspects, the ASO consists of SEQ ID NO:15. In some aspects, the ASO consists of SEQ ID NO:17.

Also disclosed herein is a method of identifying an agent for treatment of a SynGAP-associated neurodevelopmental disorder comprising (a) providing a sample with reference level of SynGAP1; (b) treating the sample with an agent; (c) measuring a level of SynGAP1 in the sample; (d) identifying an agent as an agent for treatment of a SynGAP-associated neurodevelopmental disorder when the level of SynGAP1 in the sample is increased in the presence of the agent as compared to the reference level of SynGAP1.

In some aspects, the method of identifying an agent for treatment of a SynGAP-associated neurodevelopmental disorder further comprises measuring the level of one or more isoforms of SynGAP1. In some aspects, the method further comprises measuring the level of SynGAP1 protein. In some aspects, the one or more isoforms of SynGAP comprise SynGAP1 α1, SynGAP1 α2, SynGAP1 β, SynGAP1 γ, or any combination thereof. In some aspects, the one or more isoforms of SynGAP1 is SynGAP1 α1. In some aspects, the one or more isoforms of SynGAP1 is SynGAP1 α2. In some aspects, the one or more isoforms of SynGAP1 is SynGAP1 β. In some aspects, the one or more isoforms of SynGAP1 is SynGAP1 γ. In some aspects, the method further comprises measuring expression of Ras, Rap1, Rac1, or any combination thereof.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various aspects of the features of this disclosure are described herein. However, it should be understood that such aspects are provided merely by way of example, and numerous variations, changes, and substitutions can occur to those skilled in the art without departing from the scope of this disclosure. It should also be understood that various alternatives to the specific aspects described herein are also within the scope of this disclosure.

BRIEF DESCRIPTION OF DRAWINGS

FIG. 1A shows schematic diagrams of SynGAP1 splicing. Exon structures that generate C-terminal variants ($\alpha$1, $\alpha$2, $\beta$, $\gamma$) are shown. Note that different reading frame usage in exons 18 and 20 generates isoforms $\beta$ (exon 18b) and $\alpha$2 (Exon 20b), respectively.

FIG. 1B shows C-terminal sequences of SynGAP isoforms. SynGAP $\alpha$1 isoform contains a PDZ ligand (blue box). Yellow highlighted area indicates coiled-coil domain sequences (encoded in exon 17-18a), and is required for liquid-liquid phase separation (LLPS). Note that SynGAP $\beta$ harbors a truncated coiled-coil domain (Orange box). Black underline indicates antigen sequences for raising isoform-specific antibodies.

FIG. 1C shows specificity of isoform-specific SynGAP antibodies (JH2469, JH7265, JH7206, and JH7366). Lysate from HEK 293T cells expressing GFP-tagged SynGAP isoforms and brain tissue lysate from SynGAP1 +/+ or +/− mouse were probed with each antibody.

FIG. 1D shows distribution of SynGAP in various tissues. Asterisks indicate non-specific bands that are also detected in tissue from knockout mice.

FIG. 2A shows schematic diagram of LLPS sedimentation assay. Cell lysate in assay buffer was centrifuged and supernatant was collected as the soluble (S) fraction. Pellet was resuspended and sonicated in a volume of assay buffer equal to that of (S), and represents the pellet (P) fraction.

FIG. 2B shows an LLPS sedimentation assay of SynGAP $\alpha$1 WT and SynGAP $\alpha$1 L-D&K-D (LLPS mutant) with PSD-95. SynGAP $\alpha$1 WT and PSD-95, when expressed singly, are largely enriched in (S). When co-expressed, SynGAP $\alpha$1 WT and PSD-95 both show an increased (P) fraction. SynGAP $\alpha$1 L-D&K-D is less competent than SynGAP $\alpha$1 WT to enhance the PSD-95 (P) fraction.

FIG. 2C shows the ratio [P]/[Total] of SynGAP or PSD-95 in phase separation assay (B) (N=4, *P<0.001, P<0.01, One-way ANOVA followed by Tukey test).

FIG. 2D shows LLPS sedimentation assay using the various SynGAP isoforms. SynGAP $\alpha$1 was robustly drawn to (P) fraction with PSD-95, while SynGAP $\beta$ did not undergo LLPS with PSD-95.

FIG. 2E shows the ratio [P]/[Total] of SynGAP or PSD-95 in phase separation assay (D) (N=4, *P<0.001, P<0.01, One-way ANOVA followed by Tukey test).

FIG. 2F shows colocalization assay for SynGAP $\alpha$1 WT and SynGAP $\alpha$1 L-D&K-D with PSD-95 in living cells. SynGAP $\alpha$1 WT and PSD-95 exhibit relatively uniform cytoplasmic distribution when expressed singly. When co-expressed, SynGAP $\alpha$1 WT and PSD-95 colocalized in distinct cytoplasmic puncta (>1 μm) 18 h after transfection. SynGAP $\alpha$1 L-D&K-D was less competent to induce the formation of cytoplasmic puncta when co-expressed with PSD-95 (N=10 cells, *P<0.001, P<0.01, One-way ANOVA followed by Tukey test).

FIG. 2G shows colocalization assay for various SynGAP isoforms in living cells. SynGAP $\alpha$1 was reliably observed in puncta also containing PSD-95, while cytoplasmic puncta were largely absent under conditions of co-expression of non-$\alpha$1 SynGAP isoforms and PSD-95.

FIG. 4A provides panels showing changes in SynGAP localization in live cultured hippocampal neurons both basally and following chemLTP. Endogenous SynGAP was knocked down and rescued with shRNA-resistant GFP-tagged SynGAP isoform constructs. GFP-SynGAP $\alpha$1 (Green) was dynamically dispersed upon chemLTP (Left panels, Yellow arrows). mCherry was used as a morphology marker to monitor changes in spine size during LTP. Note that neither SynGAP β nor γ rescued SynGAP knockdown-dependent aberrant spine enlargement. SynGAP β did not display synaptic enrichment, and was not dispersed upon chemLTP. SynGAP α2 exhibits a weak dispersion phenotype. Only SynGAP α1 was rapidly dispersed upon chemLTP.

FIG. 4B provides graphs showing the effects of the various SynGAP isoforms on chemLTP-dependent changes in spine size (bottom left), and changes in fold synaptic enrichment of SynGAP relative to expression in the dendritic shaft (bottom right) (N=8, *P<0.001, P<0.01, One-way ANOVA followed by Tukey test).

DETAILED DESCRIPTION

A. Introduction

Figure 1E:
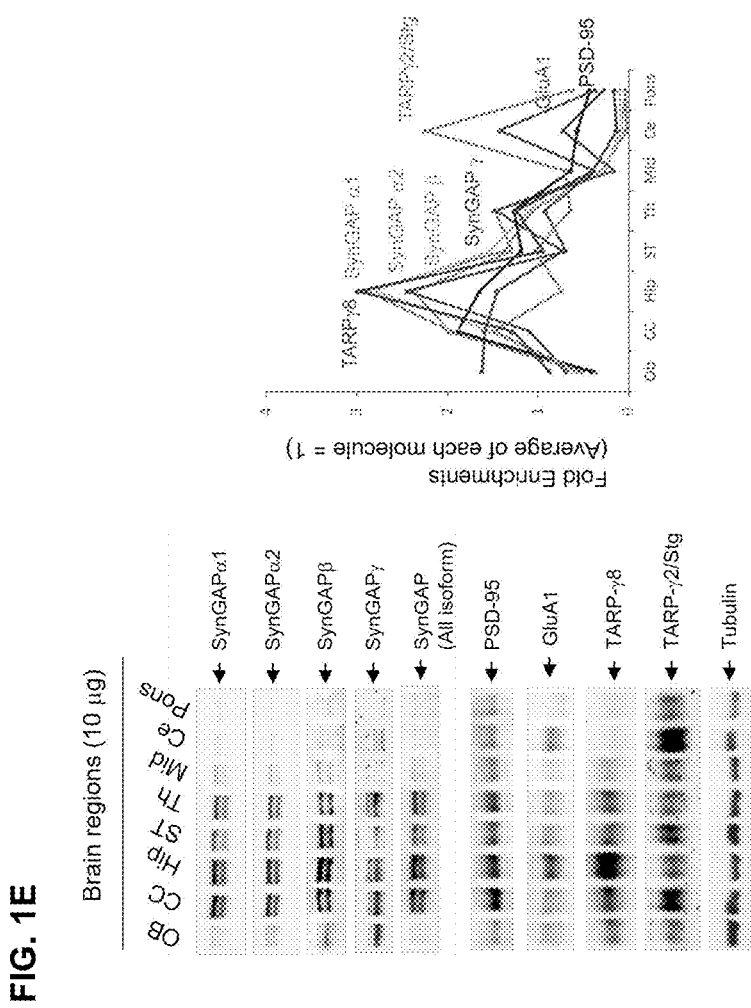
FIG. 1E shows distribution of SynGAP isoforms across brain regions. (OB: Olfactory bulb, CC: Cerebral cortex, Hip: Hippocampus, ST: Striatum, Th: Thalamus, Mid: Midbrain, Ce: Cerebellum).

In certain aspects, this disclosure describes compositions and methods for treatment of SynGAP-mutant diseases.

B. Definitions

Unless otherwise indicated, reference to "SynGAP" or derivatives thereof means a polynucleotide or amino acid sequence that is substantially homologous to at least one of the isoforms (e.g., α1, α2, β, γ) of SynGAP1 protein. SynGAP has been described previously in U.S. Pat. No. 6,723,838 B1, which is incorporated by reference in its entirety.

By the term "SynGAP activity" or like term is meant those functions attributed to SynGAP as discussed herein, e.g., PDZ domain and rasGTPase inhibition. It will be appreciated that related activities can impact SynGAP activity including synthesis of SynGAP (transcription and translation), SYNGAP processing (e.g., protein maturation including modification such as glycosylation), protein stability in SynGAP-expressing cells, and neuromodulation.

In some embodiments, the present disclosure provides methods to detect mammalian SynGAP in vitro or in vivo. Further provided are useful methods for modulating, including enhancing, expression or activity of SynGAP in particular cells such as those that include chemical synapses with SynGAP. By way of illustration, one can provide an antisense SynGAP molecule to neurons to selectively inhibit SYNGAP activity in those neurons. In addition, a suitable SynGAP antibody or antigen-binding fragment thereof can be provided to reduce or eliminate SynGAP function. Further, compounds identified by the methods of this disclosure can be administered in vitro or in vivo e.g., to enhance SynGAP function including increasing the number or quality of chemical synapses that include SynGAP.

In some embodiments, therapeutic methods of this disclosure include administration of a therapeutically effective amount of an agent or a composition as described herein to a subject and particularly a human patient in need of such treatment. Therapeutic methods of the disclosure also include administration of an effective amount of compound identified by this disclosure to the subject, in need of such treatment for an indication as disclosed herein.

A "SynGAP-associated neurodevelopmental disorder" (or "NDD," "neurodevelopmental disorder," "neurodegenerative disease," or "neurodegenerative disorder" as used herein) is a disease in which one or more isoforms of SynGAP is aberrantly expressed. NDDs include, but are not limited to, an intellectual disability (ID), autism spectrum disorders (ASD), epilepsy, schizophrenia, or Pervasive Developmental Disorder-Not Otherwise Specified (PDD-NOS).

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder.

As used herein, the term "effective amount" in the context of the administration of a therapy to a subject refers to the amount of a therapy that achieves a desired prophylactic or therapeutic effect.

The term "therapeutically effective amount" refers to an amount of an agent or other drug effective to "treat" a disease or disorder in a subject or mammal.

A "prophylactically effective amount" refers to an amount effective, at dosages and for periods of time necessary, to achieve the desired prophylactic result. In some aspects, since a prophylactic dose is used in subjects prior to or at an earlier stage of disease, the prophylactically effective amount will be less than the therapeutically effective amount.

As used herein, the terms "subject" and "patient" are used interchangeably. The subject can be an animal. In some aspects, the subject is a mammal such as a non-primate (e.g., cow, pig, horse, cat, dog, rat, etc.) or a primate (e.g., monkey or human). In some aspects, the subject is a human. In certain aspects, such terms refer to a non-human animal (e.g., a non-human animal such as a pig, horse, cow, cat, or dog).

As used herein, the term "sample" refers to any biological sample obtained from a subject, cell line, tissue, or other source of cells (e.g., blood). Non-limiting sources of a sample for use in the present disclosure include solid tissue, biopsy aspirates, ascites, fluidic extracts, blood, plasma, serum, spinal fluid, lymph fluid, the external sections of the skin, respiratory, intestinal, and genitourinary tracts, tears, saliva, milk, tumors, organs, cell cultures and/or cell culture constituents, for example.

As disclosed herein, a "reference sample" can be used to correlate and compare the results obtained using various methods of the disclosure from a test sample. Reference samples can be cells (e.g., cell lines, cell pellets) or tissue. The levels of one or more isoforms of SynGAP in the "reference sample" may be an absolute or relative amount, a range of amount, a minimum and/or maximum amount, a mean amount, and/or a median amount of one or more isoforms of SynGAP. In some embodiments, a reference sample is obtained from a subject that does not exhibit a SynGAP-associated neurodevelopmental disorder. The diagnostic methods of the disclosure involve a comparison between expression levels of one or more isoforms of SynGAP in a test sample and a "reference value." In some aspects, the reference value is the expression level of the one or more isoforms of SynGAP in a reference sample. A reference value may be a predetermined value and may also be determined from reference samples (e.g., control biological samples) tested in parallel with the test samples. A reference value can be a single cut-off value, such as a median or mean or a range of values, such as a confidence interval. In some aspects, the reference sample is a sample from a healthy tissue, in particular a corresponding tissue which is not affected by a neurodegenerative disorder. These types of reference samples are referred to as negative control samples. In other aspects, the reference sample is a sample (e.g., tissue, cells, blood) from a sample that expresses one or more isoforms of SynGAP.

As used herein, the term "host cell" can be any type of cell, e.g., a primary cell, a cell in culture, or a cell from a cell line. In specific aspects, the term "host cell" refers to a cell transfected with a nucleic acid molecule and the progeny or potential progeny of such a cell. Progeny of such a cell are not necessarily identical to the parent cell transfected with the nucleic acid molecule, e.g., due to mutations or environmental influences that may occur in succeeding generations or integration of the nucleic acid molecule into the host cell genome.

As used herein, the terms "about" and "approximately," when used to modify a numeric value or numeric range, indicate that deviations of 5% to 10% above and 5% to 10% below the value or range remain within the intended meaning of the recited value or range It is understood that wherever aspects are described herein with the language "comprising," otherwise analogous aspects described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following aspects: A, B, and C; A, B, or C; A or C; A or B; B or C; A and C; A and B; and B and C; A (alone); B (alone); and C (alone).

C. Methods of Treatment

Provided herein is a novel noncoding SYNGAP antisense RNA, SYNGAP1-AS, that is expressed in humans. It was found that this SYNGAP1-AS inhibits SYNGAP1 translation and limits the level of expression of SYNGAP1. In efforts to raise SYNGAP1 expression in SYNGAP1 haploinsufficiency disorders, agents that inhibit the expression of the SYNGAP-AS and in turn increase expression of the normal SYNGAP1 allele were developed. Exemplary agents that were developed include antisense oligos (ASOs). In some embodiments, ASOs (e.g., any of the variety of ASOs provided herein) are potential therapeutic agents for the treatment of SYNGAP1 haploinsufficiency and MRD5 and are effective against SYNGAP1 haploinsufficiency mutations.

Illustrative subjects for the purposes of this disclosure include those mammals suffering from or susceptible to those conditions generally discussed above, e.g., disorders of the CNS (central nervous system) and PNS (peripheral nervous system) such as an affective disorder, cognitive disorder, or a neurodegenerative disorder. In some embodiments, any of a variety of CNS disorders may be alleviated by selectively enhancing or inhibiting SYNGAP activity in the CNS, e.g., in the brain. As is demonstrated herein, SYNGAP is predominantly expressed in the brain. Illustrative CNS disorders are affective disorders (e.g., depression), disorders of thought (e.g., schizophrenia) and degenerative disorders, as well as disorders manifested by application of anesthesia CNS disorders of severe impact include pre-senile dementia (sometimes referred to as Alzheimer's disease (AD) or early-onset Alzheimer's disease), senile dementia (dementia of the Alzheimer's type), Parkinson's disease (PD), and Huntington's disease (HD, sometimes referenced as Huntington's chorea). Such CNS disorders are well-represented in the human population. See generally; Gusella, J. F. et al. (1983) Nature 306: 234; Borlauer. W. and Jprmuloewoca. P. (eds.) (1976); Adv. in Parkinsonism: Biochemistry, Physiology, Treatment. Fifth International Symposium on Parkinson's Disease (Vienna) Basel: Roche; and references cited therein. Subjects that have suffered acute CNS trauma, e.g., brain or spinal cord ischemia or trauma, stroke, heart attack or neurological deficits that may be associated with surgery also may be treated in accordance with methods provided herein.

In some embodiments, methods provided herein include administering a composition to a subject in need of treatment or suspected of needing treatment in any of several ways. For example, a desired SYNGAP or SYNGAP-related polynucleotide, immune system molecule or a therapeutic compound (e.g., agent) can be administered as a prophylactic to prevent the onset of or reduce the severity of a targeted condition. Alternatively, the therapeutic molecule can be administered during or following the course of a targeted condition. In some embodiments, the subject exhibits a SynGAP-associated neurodevelopmental disorder.

In some aspects, a composition that includes an agent for treating a subject exhibiting a SynGAP-associated neurodevelopmental disorder is suitable for administration to a human. Examples of routes of administration applicable to the pharmaceutical composition and/or the method of the disclosure include, but are not limited to, oral, intravenous (iv), intramuscular (im), subcutaneous (sc), trans-dermal, and rectal. Compositions may also be administered directly to the nervous system including, but not limited to, intracerebral, intraventricular, intracerebroventricular, intrathecal, intracisternal, intraspinal or peri-spinal routes of administration by delivery via intracranial or intravertebral needles or catheters with or without pump devices. The cholinesterase inhibitors or levodopa or dopamine agonists(s) and the anticonvulsant or anti-epileptic agent(s) may be administered according to simultaneous or alternating regimens, at the same or different times during the course of the therapy, concurrently in divided or single forms.

In some aspects, the agent (e.g., agent for treating a subject exhibiting a SynGAP-associated neurodevelopmental disorder) can be administered to a subject, either alone or in combination with one or more therapeutic agents, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Such compositions may be prepared for use in parenteral administration, to particularly in the form of liquid solutions or suspensions; for oral administration, particularly in the form of tablets or capsules; intranasally, particularly in the form of powders, nasal drops, or aerosols; vaginally; topically e.g., in the form of a cream; rectally e.g., as a suppository; etc.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain of the compounds.

Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Other delivery systems will administer the therapeutic agent(s) directly, e.g., by use of stents.

An agent (e.g., an agent for treating a subject exhibiting a SynGAP-associated neurodevelopmental disorder) provided herein can be employed as the sole active pharmaceutical agent or can be used in combination with other active ingredients, e.g., those compounds known in the field to be useful in the treatment of cognitive and neurological disorders.

The concentration of one or more agents (e.g., agents for treating a subject exhibiting a SynGAP-associated neurodevelopmental disorder) in a therapeutic composition will vary depending upon a number of factors, including the dosage of the therapeutic compound to be administered, the chemical characteristics (e.g., hydrophobicity) of the composition employed, and the intended mode and route of administration. In general, one or more than one of the agents may be provided in an aqueous physiological buffer solution containing about 0.1 to 10% w/v of a compound for parenteral administration. As noted above, GAPYSN antibodies and antigen-binding fragments thereof can be modified according to standard methods to deliver useful molecules or can be modified to include detectable labels and tags to facilitate visualization of synapses including SYNGAP.

It will be appreciated that the actual preferred amounts of an agent (e.g., an agent for treating a subject exhibiting a SynGAP-associated neurodevelopmental disorder) used in a given therapy will vary according to e.g., the specific agent being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines. Suitable dose ranges may include from about 1 µg/kg to about 100 mg/kg of body weight per day.

Agents (e.g., agents for treating a subject exhibiting a SynGAP-associated neurodevelopmental disorder) identified by any of the variety of methods provided herein can be suitably administered by conventional routes. For example, when the agent is a synthetic or naturally-occurring chemical compound such as a drug, it will be preferred to administer the compound in a protonated and water-soluble form, e.g., as a pharmaceutically acceptable salt, typically an acid addition salt such as an inorganic acid addition salt, e.g., a hydrochloride, sulfate, or phosphate salt, or as an organic acid addition salt such as an acetate, maleate, fumarate, tartrate, or citrate salt. Pharmaceutically acceptable salts of therapeutic compounds of the disclosure also can include metal salts, particularly alkali metal salts such as a sodium salt or potassium salt; alkaline earth metal salts such as a magnesium or calcium salt; ammonium salts such an ammonium or tetramethyl ammonium salt; or an amino acid addition salts such as a lysine, glycine, or phenylalanine salt.

Current therapeutic practice typically utilizes one or a combination of different drugs to treat the SynGAP-associated neurodevelopmental disorders. In some embodiments, the present disclosure provides methods for identifying agents capable of treating or preventing SynGAP-associated neurodevelopmental disorders. Agents identified by such methods may be used either alone, or in combination with currently used therapies to alleviate the disorders or to reduce symptoms associated with SynGAP-associated neurodevelopmental disorders. In particular, specific drugs have been reported to be of use in the treatment of affective disorders, e.g., depression, manic-depressive disorders, anxiety disorders such as panic attacks and the like. Many of these drugs have been reported to work by modulating synaptic function, e.g., by altering receptor activity. According to some methods of the present disclosure, agents (e.g., any of the variety of agents provided herein) with capacity to modulate neuroreceptors, e.g., by increasing SYNGAP activity, are similarly effective at treating depressive disorders. Such compounds may be identified by practice of any of the variety of screening methods described herein.

Agents identified by any of the variety of methods of the present disclosure can be further tested if desired in standard assays used to measure higher nervous system functions such as habituation, sensitization, learning and memory. Examples of such systems include those using well-known test organisms such as *Aplysia, C. elegans, D. melanogaster*, primates such as monkeys, and rodents such as mice, rabbits and rats. Preferred compounds are those that can increase or decrease at least one of these functions by at least about 10%, 20%, 30%, 40%, 50%, 60%, 70%, 80%, 90% up to about 100% as determined by a suitable testing protocol recognized in the test organism selected.

Agents identified by the any of the variety of methods provided herein can be administered to a subject and preferably a human patient suffering from or suspected of suffering from a SynGAP-associated neurodevelopmental disorder.

In some embodiments, systems for performing testing methods provided herein involve cell culture assays, e.g., cell culture assays employing primary or cultured cells derived from the nervous system. In some embodiments, cultured cells are capable of expressing or express excitatory chemical synapses including SYNGAP such as CNS-derived cells such as those derived from the brain. Illustrative examples of cells are provided below in the Examples. If desired, a cultured cell line can be tested for SYNGAP expression by determining if the cells express or can be made to express SYNGAP. Methods for detecting expression include immunological methods involving a suitable SYNGAP antibody, e.g., a Western blot, RIA, ELISA or other immunoassay known in the art.

In addition to the specific CNS- and PNS-related applications described herein, compositions and methods provided herein can also be used to therapeutically intervene in other systems that are affected by inappropriate SYNGAP activity. Such systems include, without limitation, the endocrine system for treatment of hormonal imbalances, the immune system for intervention in antigen processing, secreted immunomodulators, and viral processing, as well as anti-tumor applications, such as regulation of synapse formation in malignancies of the neuroendocrine system. To reduce or avoid CNS- or PNS-related side-effects, agents identified using any of the variety of methods of this disclosure may be re-screened multiple times, e.g., 2, 3, 4, or 5 times to identify agents that specifically modulate SYNGAP in the neurons.

D. Methods of Identifying Therapeutically-Effective Treatments of Neurodevelopmental Disorders Disclosed herein are methods to identify therapeutically effective treatments of SynGAP-associated neurodevelopmental disorders. In some aspects, methods disclosed herein includes treating a sample with an agent as disclosed herein. In some aspects, methods provided herein include treating a sample with an agent to modulate expression of one or more isoforms of SynGAP1 (e.g., SynGAP1 α1, α2, β, and/or γ). In some aspects, methods provided herein further include administering a second agent to the sample. After administering the second agent, one can then measure at SynGAP1 expression of any downstream marker including but not limited to Ras, Rap1, or Rac1 to determine efficacy of the second agent. In some aspects, methods provided herein include modulating expression of one or more isoforms of SynGAP1.

E. Compositions and Agents

In some aspects, disclosed herein are compositions used in the methods described herein. In some aspects, the compositions include agents that modulate expression of SynGAP1 (i.e., an mRNA variant or protein of any SynGAP1 isoform, e.g., α1, α2, β, and/or γ). In some aspects, the agent modulates expression of SynGAP1 by binding to the isoform SynGAP α1. In some aspects, the agent modulates expression of SynGAP1 by binding to the isoform SynGAP α2. In some aspects, the agent modulates expression of SynGAP1 by binding to the isoform SynGAP β. In some aspects, the agent modulates expression of SynGAP1 by binding to the isoform SynGAP γ. In some aspects, the agent is a nucleic acid, a protein, a small molecule, a biologic, or any combination thereof. In some aspects, the Chemical modifications as disclosed herein can be made to any nucleotide in SEQ ID Nos: 18, 15, or 17.

In some aspects, also disclosed herein are ASOs that target SYNGAP2. See Table 1 below.

TABLE 1

SYNGAP2 suppressors.

| ASO name | ASO Target sequence | ASO sequence (DNA) | ASO sequence (RNA) |
|---|---|---|---|
| AS-ASO-1 | GCTGCGTTTCCCGG TGATTAA (SEQ ID NO: 1) | TTAATCACCGGGAA ACGCAGC (SEQ ID NO: 10) | UUAAUCACCGGGAA ACGCAGC (SEQ ID NO: 19) |
| AS-ASO-2 | GTTTCCCGGTGATT AAGTGTA (SEQ ID NO: 2) | TACACTTAATCACC GGGAAAC (SEQ ID NO: 11) | UACACUUAAUCACC GGGAAAC (SEQ ID NO: 20) |
| AS-ASO-3 | AAGCTGCGTTTCCC GGTGATT (SEQ ID NO: 3) | AATCACCGGGAAAC GCAGCTT (SEQ ID NO: 12) | AAUCACCGGGAAAC GCAGCUU (SEQ ID NO: 21) |
| AS-ASO-4 | ACCTGCCAATGATG CTCTTGA (SEQ ID NO: 4) | TCAAGAGCATCATT GGCAGGT (SEQ ID NO: 13) | UCAAGAGCAUCAUU GGCAGGU (SEQ ID NO: 22) |
| AS-ASO-5 | GGACGGAAGGCTTC TCAAGAG (SEQ ID NO: 5) | CTCTTGAGAAGCCT TCCGTCC (SEQ ID NO: 14) | CUCUUGAGAAGCCU UCCGUCC (SEQ ID NO: 23) |
| AS-ASO-6 | GCAAATGTAATCAA ACTAA (SEQ ID NO: 6) | TTAGTTTGATTACA TTTGC (SEQ ID NO: 15) | UUAGUUUGAUUACA UUUGC (SEQ ID NO: 24) |
| AS-ASO-7 | GCCAGCCATGGTAT CTCATTC (SEQ ID NO: 7) | GAATGAGATACCAT GGCTGGC (SEQ ID NO: 16) | GAAUGAGAUACCAU GGCUGGC (SEQ ID NO: 25) |
| AS-ASO-8 | GGATCCCTGCAAAT GTAATCA (SEQ ID NO: 8) | TGATTACATTTGCA GGGATCC (SEQ ID NO: 17) | UGAUUACAUUUGCA GGGAUCC (SEQ ID NO: 26) |
| AS-ASO-9 | TGTGAGGTCAGAGC GAGACCA (SEQ ID NO: 9) | TGGTCTCGCTCTGA CCTCACA (SEQ ID NO: 18) | ACCAGAGCGAGACU GGAGUGU (SEQ ID NO: 27) | agent is a nucleic acid. In some aspects, the nucleic acid is an antisense oligonucleotide (ASO). In some aspects, the ASO targets SynGAP2. In some aspects, the ASO increases expression of SynGAP1 protein. In some aspects, administering the ASO increases expression of one or more isoforms of SynGAP1 (e.g., SynGAP1 α1, α2, β, and/or γ). In some aspects, the ASO includes one or more chemical modifications. In some aspects, the one or more chemical modifications is a modification by phosphorothioates. In some aspects, the one or more chemical modifications is a 2'-O-methyl oligonucleotide.

In some aspects, the ASO is or includes modified SEQ ID NO:18 (T*G*G* TCT CGC TCT GAC CTC *A*C*A), wherein * indicates that a nucleotide has been modified with a Phosphorothioate (PS). In some aspects, the ASO is or includes modified SEQ ID NO:15 (T*T*A* GTT TGA TTA CAT T *T*G*C). In some aspects, the ASO is or includes modified SEQ ID NO:17 (T*G*A* TTA CAT TTG CAG GGA *T*C*C). In some aspects, SEQ ID Nos: 18, 15, and 17 do not have the chemical modifications:

SEQ ID NO: 18: (TGG TCT CGC TCT GAC CTC ACA),

SEQ ID NO: 15 (TTA GTT TGA TTA CAT T TGC),

SEQ ID NO: 17 (TGA TTA CAT TTG CAG GGA TCC).

In some aspects, an ASO DNA sequence comprising SEQ ID NOs: 10-18 is transcribed into one of SEQ ID NOs: 19-27. As disclosed herein, ASOs selected from SEQ ID NOs: 10-18 target a SYNGAP2 sequence selected from SEQ ID NOs: 1-9. In particular, an ASO comprising SEQ ID NO:10 can be transcribed into an RNA molecule comprising SEQ ID NO:19. An ASO comprising SEQ ID NO:11 can be transcribed into an RNA molecule comprising SEQ ID NO:20. An ASO comprising SEQ ID NO:12 can be transcribed into an RNA molecule comprising SEQ ID NO:21. An ASO comprising SEQ ID NO:13 can be transcribed into an RNA molecule comprising SEQ ID NO:22. An ASO comprising SEQ ID NO:14 can be transcribed into an RNA molecule comprising SEQ ID NO:23. An ASO comprising SEQ ID NO:15 can be transcribed into an RNA molecule comprising SEQ ID NO:24. An ASO comprising SEQ ID NO:16 can be transcribed into an RNA molecule comprising SEQ ID NO:25. An ASO comprising SEQ ID NO:17 can be transcribed into an RNA molecule comprising SEQ ID NO:26. An ASO comprising SEQ ID NO:18 can be transcribed into an RNA molecule comprising SEQ ID NO:27.

An ASO DNA sequence comprising SEQ ID NO:10 can target a SYNGAP2 sequence comprising SEQ ID NO:1. An ASO DNA sequence comprising SEQ ID NO:11 can target a SYNGAP2 sequence comprising SEQ ID NO:2. An ASO DNA sequence comprising SEQ ID NO:12 can target a SYNGAP2 sequence comprising SEQ ID NO:3. An ASO DNA sequence comprising SEQ ID NO:13 can target a SYNGAP2 sequence comprising SEQ ID NO:4. An ASO DNA sequence comprising SEQ ID NO:14 can target a SYNGAP2 sequence comprising SEQ ID NO:5. An ASO DNA sequence comprising SEQ ID NO:15 can target a SYNGAP2 sequence comprising SEQ ID NO:6. An ASO DNA sequence comprising SEQ ID NO:16 can target a SYNGAP2 sequence comprising SEQ ID NO:7. An ASO DNA sequence comprising SEQ ID NO:17 can target a SYNGAP2 sequence comprising SEQ ID NO:8. An ASO DNA sequence comprising SEQ ID NO:18 can target a SYNGAP2 sequence comprising SEQ ID NO:9.

In some aspects, the ASO consists of a sequence selected from one of SEQ ID NO:10-18. In some aspects, the ASO is transcribed as RNS and consists of a sequence selected from SEQ ID NO:19-27. In some aspects, the ASO targets a sequence consisting of a sequence selected from SEQ ID NO:1-9.

Also disclosed herein are ASOs that target SYNGAP1. In particular, the ASOs can be one or more of (i.e., any combination of) any of the ASOs listed in Tables 2-5 below. In some aspects, one or more of the ASOs in Tables 2-5 could be combined with one or more of the ASOs in Table 1 (i.e., ASOs that target SYNGAP2). It is appreciated that any permutation or combination could be used among the ASOs in Tables 1-5.

In some aspects, disclosed herein are ASO DNA sequences that target exons of particular isoforms of SynGap1. As shown in Table 2, ASOs as disclosed herein can target the α2 isoform of SynGap1. Also disclosed herein are RNA sequences of the ASOs that can target the α2 isoform of SynGap1 and α2 isoform target sequences for the ASOs listed in Table 2.

TABLE 2

α2 isoform ASOs.

| ASO name | ASO Target sequence | ASO sequence (DNA) | ASO sequence (RNA) |
| --- | --- | --- | --- |
| Intron 18 + 0 | GTGGAAATTACAATGTCATT (SEQ ID NO: 28) | AATGACATTGTAATTTCCAC (SEQ ID NO: 53) | AAUGACAUUGUAAUUUCCAC (SEQ ID NO: 78) |
| Intron 18 + 5 | AATTACAATGTCATTTATCT (SEQ ID NO: 29) | AGATAAATGACATTGTAATT (SEQ ID NO: 54) | AGAUAAAUGACAUUGUAAUU (SEQ ID NO: 79) |
| Intron 18 + 10 | CAATGTCATTTATCTTCTCC (SEQ ID NO: 30) | GGAGAAGATAAATGACATTG (SEQ ID NO: 55) | GGAGAAGAUAAAUGACAUUG (SEQ ID NO: 80) |
| Intron 18 + 15 | TCATTTATCTTCTCCGTGTC (SEQ ID NO: 31) | GACACGGAGAAGATAAATGA (SEQ ID NO: 56) | GACACGGAGAAGAUAAAUGA (SEQ ID NO: 81) |
| Intron 18 + 20 | TATCTTCTCCGTGTCCCATC (SEQ ID NO: 32) | GATGGGACACGGAGAAGATA (SEQ ID NO: 57) | GAUGGGACACGGAGAAGAUA (SEQ ID NO: 82) |
| Intron 18 + 25 | TCTCCGTGTCCCATCCCCAT (SEQ ID NO: 33) | ATGGGGATGGGACACGGAGA (SEQ ID NO: 58) | AUGGGGAUGGGACACGGAGA (SEQ ID NO: 83) |
| Intron 18 + 30 | GTGTCCCATCCCCATCCATC (SEQ ID NO: 34) | GATGGATGGGGATGGGACAC (SEQ ID NO: 59) | GAUGGAUGGGGAUGGGACAC (SEQ ID NO: 84) |
| Intron 18 + 35 | CCATCCCCATCCATCCCACT (SEQ ID NO: 35) | AGTGGGATGGATGGGGATGG (SEQ ID NO: 60) | AGUGGGAUGGAUGGGGAUGG (SEQ ID NO: 85) |
| Intron 18 + 40 | CCCATCCATCCCACTGTCTT (SEQ ID NO: 36) | AAGACAGTGGGATGGATGGG (SEQ ID NO: 61) | AAGACAGUGGGAUGGAUGGG (SEQ ID NO: 86) |
| Intron 18 + 45 | CCATCCCACTGTCTTTCGTG (SEQ ID NO: 37) | CACGAAAGACAGTGGGATGG (SEQ ID NO: 62) | CACGAAAGACAGUGGGAUGG (SEQ ID NO: 87) |
| Intron 18 + 50 | CCACTGTCTTTCGTGCACTC (SEQ ID NO: 38) | GAGTGCACGAAAGACAGTGG (SEQ ID NO: 63) | GAGUGCACGAAAGACAGUGG (SEQ ID NO: 88) |
| Intron 18 + 55 | GTCTTTCGTGCACTCACTAC (SEQ ID NO: 39) | GTAGTGAGTGCACGAAAGAC (SEQ ID NO: 64) | GUAGUGAGUGCACGAAAGAC (SEQ ID NO: 89) |
| Intron 18 + 60 | TCGTGCACTCACTACACCAG (SEQ ID NO: 40) | CTGGTGTAGTGAGTGCACGA (SEQ ID NO: 65) | CUGGUGUAGUGAGUGCACGA (SEQ ID NO: 90) |

TABLE 2-continued

α2 isoform ASOs.

| ASO name | ASO Target sequence | ASO sequence (DNA) | ASO sequence (RNA) |
| --- | --- | --- | --- |
| Intron 18 + 65 | CACTCACTACACCA GCCACC (SEQ ID NO: 41) | GGTGGCTGGTGTAG TGAGTG (SEQ ID NO: 66) | GGUGGCUGGUGUAG UGAGUG (SEQ ID NO: 91) |
| Intron 18 + 70 | ACTACACCAGCCAC CTAGCC (SEQ ID NO: 42) | GGCTAGGTGGCTGG TGTAGT (SEQ ID NO: 67) | GGCUAGGUGGCUGG UGUAGU (SEQ ID NO: 92) |
| Intron 19 - 73 | Ggctataggggaggccactg (SEQ ID NO: 43) | CAGTGGCCTCCCCT ATAGCC (SEQ ID NO: 68) | CAGUGGCCUCCCCU AUAGCC (SEQ ID NO: 93) |
| Intron 19 - 68 | Tagggaggccactgctagg (SEQ ID NO: 44) | CCTAGCAGTGGCCT CCCCTA (SEQ ID NO: 69) | CCUAGCAGUGGCCU CCCCUA (SEQ ID NO: 94) |
| Intron 19 - 63 | Gaggccactgctaggggact (SEQ ID NO: 45) | AGTCCCCTAGCAGT GGCCTC (SEQ ID NO: 70) | AGUCCCCUAGCAGU GGCCUC (SEQ ID NO: 95) |
| Intron 19 - 58 | Cactgctaggggactggcat (SEQ ID NO: 46) | ATGCCAGTCCCCTA GCAGTG (SEQ ID NO: 71) | AUGCCAGUCCCCUA GCAGUG (SEQ ID NO: 96) |
| Intron 19 - 53 | Ctaggggactggcatccagg (SEQ ID NO: 47) | CCTGGATGCCAGTC CCCTAG (SEQ ID NO: 72) | CCUGGAUGCCAGUC CCCUAG (SEQ ID NO: 97) |
| Intron 19 - 51 | Aggggactggcatccaggcc (SEQ ID NO: 48) | GGCCTGGATGCCAG TCCCCT (SEQ ID NO: 73) | GGCCUGGAUGCCAG UCCCCU (SEQ ID NO: 98) |
| Intron 19 - 43 | Ggcatccaggccccttgaa (SEQ ID NO: 49) | TTCAAGGGGCCTG GATGCC (SEQ ID NO: 74) | UUCAAGGGGGCCUG GAUGCC (SEQ ID NO: 99) |
| Intron 19 - 38 | Ccaggccccttgaagcgtc (SEQ ID NO: 50) | GACGCTTCAAGGGG GCCTGG (SEQ ID NO: 75) | GACGCUUCAAGGGG GCCUGG (SEQ ID NO: 100) |
| Intron 19 - 30 | Ccttgaagcgtctcaataag (SEQ ID NO: 51) | CTTATTGAGACGCT TCAAGG (SEQ ID NO: 76) | CUUAUUGAGACGCU UCAAGG (SEQ ID NO: 101) |
| Intron 19 - 28 | Ttgaagcgtctcaataagtc (SEQ ID NO: 52) | GACTTATTGAGACG CTTCAA (SEQ ID NO: 77) | GACUUAUUGAGACG CUUCAA (SEQ ID NO: 102) |

As shown in Table 3, ASOs as disclosed herein can target the γ isoform of SynGap1. Also disclosed herein are RNA sequences of the ASOs that can target the γ isoform of SynGap1 and γ isoform target sequences for the ASOs listed in Table 3. In some aspects, the ASO comprises a sequence selected from SEQ ID NOs:114-124. In some aspects, the ASO is transcribed into a sequence comprising a sequence selected from SEQ ID NOs:125-135. In some aspects, the ASO targets a sequence comprising a sequence selected from SEQ ID NOs:103-113.

In some aspects, the ASO consists of a sequence selected from SEQ ID NOs:114-124. In some aspects, the ASO is transcribed into a sequence consisting of a sequence selected from SEQ ID NOs:125-135. In some aspects, the ASO targets a sequence consisting of a sequence selected from SEQ ID NOs:103-113.

TABLE 3

Gamma (Exon 18-19) suppressors

| ASO name | ASO Target sequence | ASO sequence (DNA) | ASO sequence (RNA) |
| --- | --- | --- | --- |
| Gamma suppressor-1 | ccactgcagCTCCTCA TCAGGTAATT (SEQ ID NO: 103) | AATTACCTGATGAG GAGCTGCAGTGG (SEQ ID NO: 114) | AAUUACCUGAUGAG GAGCUGCAGUGG (SEQ ID NO: 125) |
| Gamma suppressor-2 | ctgcagCTCCTCATC AGGTAATT (SEQ ID NO: 104) | AATTACCTGATGAG GAGCTGCAG (SEQ ID NO: 115) | AAUUACCUGAUGAG GAGCUGCAG (SEQ ID NO: 126) |

TABLE 3-continued

Gamma (Exon 18-19) suppressors

| ASO name | ASO Target sequence | ASO sequence (DNA) | ASO sequence (RNA) |
|---|---|---|---|
| Gamma suppressor-3 | cagCTCCTCATCA GGTAATT (SEQ ID NO: 105) | AATTACCTGATGAG GAGCTG (SEQ ID NO: 116) | AAUUACCUGAUGAG GAGCUG (SEQ ID NO: 127) |
| Exon 19 + 0 | CTCCTCATCAGG TAATTCTC (SEQ ID NO: 106) | GAGAATTACCTGAT GAGGAG (SEQ ID NO: 117) | GAGAAUUACCUGAU GAGGAG (SEQ ID NO: 128) |
| Exon 19 + 5 | CATCAGGTAATT CTCCTGGT (SEQ ID NO: 107) | ACCAGGAGAATTAC CTGATG (SEQ ID NO: 118) | ACCAGGAGAAUUAC CUGAUG (SEQ ID NO: 129) |
| Exon 19 + 10 | GGTAATTCTCCT GGTTCCGC (SEQ ID NO: 108) | GCGGAACCAGGAGA ATTACC (SEQ ID NO: 119) | GCGGAACCAGGAGA AUUACC (SEQ ID NO: 130) |
| Exon 19 + 15 | TTCTCCTGGTTCC GCTTTGG (SEQ ID NO: 109) | CCAAAGCGGAACCA GGAGAA (SEQ ID NO: 120) | CCAAAGCGGAACCA GGAGAA (SEQ ID NO: 131) |
| Exon 19 + 20 | CTGGTTCCGCTTT GGCCACG (SEQ ID NO: 110) | CGTGGCCAAAGCGG AACCAG (SEQ ID NO: 121) | CGUGGCCAAAGCGG AACCAG (SEQ ID NO: 132) |
| Exon 19 + 25 | TCCGCTTTGGCC ACGGGCGG (SEQ ID NO: 111) | CCGCCCGTGGCCAA AGCGGA (SEQ ID NO: 122) | CCGCCCGUGGCCAAA GCGGA (SEQ ID NO: 133) |
| Exon 19 + 30 | TTTGGCCACGGG CGGAGGAC (SEQ ID NO: 112) | GTCCTCCGCCCGTGG CCAAA (SEQ ID NO: 123) | GUCCUCCGCCCGUGG CCAAA (SEQ ID NO: 134) |
| Exon 19 + 35 | CCACGGGCGGAG GACACAGG (SEQ ID NO: 113) | CCTGTGTCCTCCGCC CGTGG (SEQ ID NO: 124) | CCUGUGUCCUCCGCC CGUGG (SEQ ID NO: 135) |

As shown in Table 4, ASOs as disclosed herein can target the β isoform of SynGap1 at exon 18. Also disclosed herein are RNA sequences of the ASOs that can target the β isoform of SynGap1 and β isoform target sequences for the ASOs listed in Table 4. In some aspects, the ASO comprises a sequence selected from SEQ ID NOs: 163-189. In some aspects, the ASO is transcribed into a sequence comprising a sequence selected from SEQ ID NOs:190-216. In some aspects, the ASO targets a sequence comprising a sequence selected from SEQ ID NOs:136-162.

In some aspects, the ASO consists of a sequence selected from SEQ ID NOs: 163-189. In some aspects, the ASO is transcribed into a sequence consisting of a sequence selected from SEQ ID NOs:190-216. In some aspects, the ASO targets a sequence consisting of a sequence selected from SEQ ID NOs:136-162.

TABLE 4

Beta (Exon 18 extension) Suppressors

| ASO name | ASO Target sequence | ASO sequence (DNA) | ASO sequence (RNA) |
|---|---|---|---|
| Beta suppressor-1 | TAACCCCACTGAAG CCCGTC (SEQ ID NO: 136) | GACGGGCTTCAGTG GGGTTA (SEQ ID NO: 163) | GACGGGCUUCAGUG GGGUUA (SEQ ID NO: 190) |
| Exon 18 + 84 | CGCTCAGGTGGAAA TTACAA (SEQ ID NO: 137) | TTGTAATTTCCACCT GAGCG (SEQ ID NO: 164) | UUGUAAUUUCCACC UGAGCG (SEQ ID NO: 191) |
| Exon 18 + 79 | CTCGACGCTCAGGT GGAAAT (SEQ ID NO: 138) | ATTTCCACCTGAGC GTCGAG (SEQ ID NO: 165) | AUUUCCACCUGAGC GUCGAG (SEQ ID NO: 192) |
| Exon 18 + 74 | GGCTGCTCGACGCT CAGGTG (SEQ ID NO: 139) | CACCTGAGCGTCGA GCAGCC (SEQ ID NO: 166) | CACCUGAGCGUCGA GCAGCC (SEQ ID NO: 193) |
| Exon 18 + 69 | GAAGAGGCTGCTCG ACGCTC (SEQ ID NO: 140) | GAGCGTCGAGCAGC CTCTTC (SEQ ID NO: 167) | GAGCGUCGAGCAGC CUCUUC (SEQ ID NO: 194) |

TABLE 4-continued

Beta (Exon 18 extension) Suppressors

| ASO name | ASO Target sequence | ASO sequence (DNA) | ASO sequence (RNA) |
|---|---|---|---|
| Exon 18 + 64 | CCCAAGAAGAGGCT GCTCGA (SEQ ID NO: 141) | TCGAGCAGCCTCTT CTTGGG (SEQ ID NO: 168) | UCGAGCAGCCUCUU CUUGGG (SEQ ID NO: 195) |
| Exon 18 + 59 | CAGAACCCAAGAAG AGGCTG (SEQ ID NO: 142) | CAGCCTCTTCTTGG GTTCTG (SEQ ID NO: 169) | CAGCCUCUUCUUGG GUUCUG (SEQ ID NO: 196) |
| Exon 18 + 54 | GCTGCCAGAACCCA AGAAGA (SEQ ID NO: 143) | TCTTCTTGGGTTCTG GCAGC (SEQ ID NO: 170) | UCUUCUUGGGUUCU GGCAGC (SEQ ID NO: 197) |
| Exon 18 + 49 | GAGCCGCTGCCAGA ACCCAA (SEQ ID NO: 144) | TTGGGTTCTGGCAG CGGCTC (SEQ ID NO: 171) | UUGGGUUCUGGCAG CGGCUC (SEQ ID NO: 198) |
| Exon 18 + 44 | TGGCTGAGCCGCTG CCAGAA (SEQ ID NO: 145) | TTCTGGCAGCGGCT CAGCCA (SEQ ID NO: 172) | UUCUGGCAGCGGCU CAGCCA (SEQ ID NO: 199) |
| Exon 18 + 39 | CGCCATGGCTGAGC CGCTGC (SEQ ID NO: 146) | GCAGCGGCTCAGCC ATGGCG (SEQ ID NO: 173) | GCAGCGGCUCAGCC AUGGCG (SEQ ID NO: 200) |
| Exon 18 + 34 | CACCCCGCCATGGC TGAGCC (SEQ ID NO: 147) | GGCTCAGCCATGGC GGGGTG (SEQ ID NO: 174) | GGCUCAGCCAUGGC GGGGUG (SEQ ID NO: 201) |
| Exon 18 + 29 | GGGACCACCCCGCC ATGGCT (SEQ ID NO: 148) | AGCCATGGCGGGGT GGTCCC (SEQ ID NO: 175) | AGCCAUGGCGGGGU GGUCCC (SEQ ID NO: 202) |
| Exon 18 + 24 | GCGCCGGGACCACC CCGCCA (SEQ ID NO: 149) | TGGCGGGGTGGTCC CGGCGC (SEQ ID NO: 176) | UGGCGGGGUGGUCC CGGCGC (SEQ ID NO: 203) |
| Exon 18 + 19 | GAGCTGCGCCGGGA CCACCC (SEQ ID NO: 150) | GGGTGGTCCCGGCG CAGCTC (SEQ ID NO: 177) | GGGUGGUCCCGGCG CAGCUC (SEQ ID NO: 204) |
| Exon 18 + 14 | AGGAGGAGCTGCGC CGGGAC (SEQ ID NO: 151) | GTCCCGGCGCAGCT CCTCCT (SEQ ID NO: 178) | GUCCCGGCGCAGCU CCUCCU (SEQ ID NO: 205) |
| Exon 18 + 9 | GGTGGAGGAGGAGC TGCGCC (SEQ ID NO: 152) | GGCGCAGCTCCTCC TCCACC (SEQ ID NO: 179) | GGCGCAGCUCCUCC UCCACC (SEQ ID NO: 206) |
| Exon 18 + 4 | ATGCTGGTGGAGGA GGAGCT (SEQ ID NO: 153) | AGCTCCTCCTCCAC CAGCAT (SEQ ID NO: 180) | AGCUCCUCCUCCAC CAGCAU (SEQ ID NO: 207) |
| Exon 18 − 1 | actgaagCCCGTCCCTT CAG (SEQ ID NO: 154) | CTGAAGGGACGGGC TTCAGT (SEQ ID NO: 181) | CUGAAGGGACGGGC UUCAGU (SEQ ID NO: 208) |
| Exon 18 − 7 | aaccccactgaagCCCGT CC (SEQ ID NO: 155) | GGACGGGCTTCAGT GGGGTT (SEQ ID NO: 182) | GGACGGGCUUCAGU GGGGUU (SEQ ID NO: 209) |
| Exon 18 − 11 | cactaaccccactgaagCCC (SEQ ID NO: 156) | GGGCTTCAGTGGGG TTAGTG (SEQ ID NO: 183) | GGGCUUCAGUGGGG UUAGUG (SEQ ID NO: 210) |
| Exon 18 − 16 | Cccgccactaaccccactga (SEQ ID NO: 157) | TCAGTGGGGTTAGT GGCGGG (SEQ ID NO: 184) | UCAGUGGGGUUAGU GGCGGG (SEQ ID NO: 211) |
| Exon 18 − 23 | Gcctgtgcccgccactaacc (SEQ ID NO: 158) | GGTTAGTGGCGGGC ACAGGC (SEQ ID NO: 185) | GGUUAGUGGCGGGC ACAGGC (SEQ ID NO: 212) |
| Exon 18 − 26 | Tgagcctgtgcccgccacta (SEQ ID NO: 159) | TAGTGGCGGGCACA GGCTCA (SEQ ID NO: 186) | UAGUGGCGGGCACA GGCUCA (SEQ ID NO: 213) |

TABLE 4-continued

Beta (Exon 18 extension) Suppressors

| ASO name | ASO Target sequence | ASO sequence (DNA) | ASO sequence (RNA) |
|---|---|---|---|
| Exon 18 - 31 | Ggctctgagcctgtgcccgc (SEQ ID NO: 160) | GCGGGCACAGGCTC AGAGCC (SEQ ID NO: 187) | GCGGGCACAGGCUC AGAGCC (SEQ ID NO: 214) |
| Exon 18 - 36 | Gggcaggctctgagcctgtg (SEQ ID NO: 161) | CACAGGCTCAGAGC CTGCCC (SEQ ID NO: 188) | CACAGGCUCAGAGC CUGCCC (SEQ ID NO: 215) |
| Exon 18 - 41 | Tccatgggcaggctctgagc (SEQ ID NO: 162) | GCTCAGAGCCTGCC CATGGA (SEQ ID NO: 189) | GCUCAGAGCCUGCC CAUGGA (SEQ ID NO: 216) |

As shown in Table 5, ASOs as disclosed herein can target exon 11 of SynGap1. Also disclosed herein are RNA sequences of the ASOs that can target exon 11 of SynGap1 and exon 11 target sequences for the ASOs listed in Table 5. In some aspects, the ASO comprises a sequence selected from SEQ ID NOs:295-372. In some aspects, the ASO is transcribed into a sequence comprising a sequence selected from SEQ ID NOs:373-450. In some aspects, the ASO targets a sequence comprising a sequence selected from SEQ ID NOs:217-294.

In some aspects, the ASO consists of a sequence selected from SEQ ID NOs:295-372. In some aspects, the ASO is transcribed into a sequence consisting of a sequence selected from SEQ ID NOs:373-450. In some aspects, the ASO targets a sequence consisting of a sequence selected from SEQ ID NOs:217-294.

TABLE 5

ASO targets for Exon 11.

| ASO name | ASO Target sequence | ASO sequence (DNA) | ASO sequence (RNA) |
|---|---|---|---|
| exon 11 extension suppressor-1 | cttcttcaagcagCCTCC CA (SEQ ID NO: 217) | TGGGAGGCTGCTTG AAGAAG (SEQ ID NO: 295) | UGGGAGGCUGCUUG AAGAAG (SEQ ID NO: 373) |
| exon 11 extension suppressor-2 | TCCCTGGAAGCTGA GGGTCT (SEQ ID NO: 218) | AGACCCTCAGCTTC CAGGGA (SEQ ID NO: 296) | AGACCCUCAGCUUC CAGGGA (SEQ ID NO: 374) |
| exon 11 extension suppressor-3 | CCTGGAAGCTGAGG GTCTCT (SEQ ID NO: 219) | AGAGACCCTCAGCT TCCAGG (SEQ ID NO: 297) | AGAGACCCUCAGCU UCCAGG (SEQ ID NO: 375) |
| Exon 11 - 225 | Ctctcccctccatttctct (SEQ ID NO: 220) | AGAGAAATGGAGGG GGAGAG (SEQ ID NO: 298) | AGAGAAAUGGAGG GGGAGAG (SEQ ID NO: 376) |
| Exon 11 - 220 | Cccctccatttctctctccc (SEQ ID NO: 221) | GGGAGAGAGAAATG GAGGGG (SEQ ID NO: 299) | GGGAGAGAGAAAU GGAGGGG (SEQ ID NO: 377) |
| Exon 11 - 215 | Ccatttctctctccctaatc (SEQ ID NO: 222) | GATTAGGGAGAGAG AAATGG (SEQ ID NO: 300) | GAUUAGGGAGAGA GAAAUGG (SEQ ID NO: 378) |
| Exon 11 - 210 | Tctctctccctaatctgtct (SEQ ID NO: 223) | AGACAGATTAGGGA GAGAGA (SEQ ID NO: 301) | AGACAGAUUAGGGA GAGAGA (SEQ ID NO: 379) |
| Exon 11 - 205 | Ctccctaatctgtctgttcc (SEQ ID NO: 224) | GGAACAGACAGATT AGGGAG (SEQ ID NO: 302) | GGAACAGACAGAUU AGGGAG (SEQ ID NO: 380) |
| Exon 11 - 200 | Taatctgtctgttccctctg (SEQ ID NO: 225) | CAGAGGGAACAGAC AGATTA (SEQ ID NO: 303) | CAGAGGGAACAGAC AGAUUA (SEQ ID NO: 381) |
| Exon 11 - 195 | Tgtctgttccctctgccatg (SEQ ID NO: 226) | CATGGCAGAGGGAA CAGACA (SEQ ID NO: 304) | CAUGGCAGAGGGAA CAGACA (SEQ ID NO: 382) |
| Exon 11 - 190 | Gttccctctgccatggcccc (SEQ ID NO: 227) | GGGGCCATGGCAGA GGGAAC (SEQ ID NO: 305) | GGGGCCAUGGCAGA GGGAAC (SEQ ID NO: 383) |

TABLE 5-continued

ASO targets for Exon 11.

| ASO name | ASO Target sequence | ASO sequence (DNA) | ASO sequence (RNA) |
| --- | --- | --- | --- |
| Exon 11 - 185 | Ctctgccatggccccttct (SEQ ID NO: 228) | AGAAGGGGGCCATGGCAGAG (SEQ ID NO: 306) | AGAAGGGGGCCAUGGCAGAG (SEQ ID NO: 384) |
| Exon 11 - 180 | Ccatggccccttcttcaag (SEQ ID NO: 229) | CTTGAAGAAGGGGGCCATGG (SEQ ID NO: 307) | CUUGAAGAAGGGGGCCAUGG (SEQ ID NO: 385) |
| Exon 11 - 175 | gccccttcttcaagcagCC (SEQ ID NO: 230) | GGCTGCTTGAAGAAGGGGGC (SEQ ID NO: 308) | GGCUGCUUGAAGAAGGGGGC (SEQ ID NO: 386) |
| Exon 11 - 165 | tcaagcagCCTCCCATCTTG (SEQ ID NO: 231) | CAAGATGGGAGGCTGCTTGA (SEQ ID NO: 309) | CAAGAUGGGAGGCUGCUUGA (SEQ ID NO: 387) |
| Exon 11 - 160 | cagCCTCCCATCTTGCTCCT (SEQ ID NO: 232) | AGGAGCAAGATGGGAGGCTG (SEQ ID NO: 310) | AGGAGCAAGAUGGGAGGCUG (SEQ ID NO: 388) |
| Exon 11 - 155 | TCCCATCTTGCTCCTGCGGT (SEQ ID NO: 233) | ACCGCAGGAGCAAGATGGGA (SEQ ID NO: 311) | ACCGCAGGAGCAAGAUGGGA (SEQ ID NO: 389) |
| Exon 11 - 150 | TCTTGCTCCTGCGGTCCCTC (SEQ ID NO: 234) | GAGGGACCGCAGGAGCAAGA (SEQ ID NO: 312) | GAGGGACCGCAGGAGCAAGA (SEQ ID NO: 390) |
| Exon 11 - 145 | CTCCTGCGGTCCCTCCTTCC (SEQ ID NO: 235) | GGAAGGAGGGACCGCAGGAG (SEQ ID NO: 313) | GGAAGGAGGGACCGCAGGAG (SEQ ID NO: 391) |
| Exon 11 - 140 | GCGGTCCCTCCTTCCCTGTC (SEQ ID NO: 236) | GACAGGGAAGGAGGGACCGC (SEQ ID NO: 314) | GACAGGGAAGGAGGGACCGC (SEQ ID NO: 392) |
| Exon 11 - 135 | CCCTCCTTCCCTGTCTCTCT (SEQ ID NO: 237) | AGAGAGACAGGGAAGGAGGG (SEQ ID NO: 315) | AGAGAGACAGGGAAGGAGGG (SEQ ID NO: 393) |
| Exon 11 - 130 | CTTCCCTGTCTCTCTCACCC (SEQ ID NO: 238) | GGGTGAGAGAGACAGGGAAG (SEQ ID NO: 316) | GGGUGAGAGAGACAGGGAAG (SEQ ID NO: 394) |
| Exon 11 - 125 | CTGTCTCTCTCACCCCTGTT (SEQ ID NO: 239) | AACAGGGGTGAGAGAGACAG (SEQ ID NO: 317) | AACAGGGGUGAGAGAGACAG (SEQ ID NO: 395) |
| Exon 11 - 120 | TCTCTCACCCCTGTTTCCAC (SEQ ID NO: 240) | GTGGAAACAGGGGTGAGAGA (SEQ ID NO: 318) | GUGGAAACAGGGGUGAGAGA (SEQ ID NO: 396) |
| Exon 11 - 115 | CACCCCTGTTTCCACACCCT (SEQ ID NO: 241) | AGGGTGTGGAAACAGGGGTG (SEQ ID NO: 319) | AGGGUGUGGAAACAGGGGUG (SEQ ID NO: 397) |
| Exon 11 - 110 | CTGTTTCCACACCCTCACCT (SEQ ID NO: 242) | AGGTGAGGGTGTGGAAACAG (SEQ ID NO: 320) | AGGUGAGGGUGUGGAAACAG (SEQ ID NO: 398) |
| Exon 11 - 105 | TCCACACCCTCACCTCCTAC (SEQ ID NO: 243) | GTAGGAGGTGAGGGTGTGGA (SEQ ID NO: 321) | GUAGGAGGUGAGGGUGUGGA (SEQ ID NO: 399) |
| Exon 11 - 100 | ACCCTCACCTCCTACCACCC (SEQ ID NO: 244) | GGGTGGTAGGAGGTGAGGGT (SEQ ID NO: 322) | GGGUGGUAGGAGGUGAGGGU (SEQ ID NO: 400) |
| Exon 11 - 95 | CACCTCCTACCACCCCCCTC (SEQ ID NO: 245) | GAGGGGGGTGGTAGGAGGTG (SEQ ID NO: 323) | GAGGGGGGUGGUAGGAGGUG (SEQ ID NO: 401) |
| Exon 11 - 90 | CCTACCACCCCCCTCAGCAT (SEQ ID NO: 246) | ATGCTGAGGGGGGTGGTAGG (SEQ ID NO: 324) | AUGCUGAGGGGGGUGGUAGG (SEQ ID NO: 402) |

TABLE 5-continued

ASO targets for Exon 11.

| ASO name | ASO Target sequence | ASO sequence (DNA) | ASO sequence (RNA) |
|---|---|---|---|
| Exon 11 - 85 | CACCCCCCTCAGCA TGTTCC (SEQ ID NO: 247) | GGAACATGCTGAGG GGGGTG (SEQ ID NO: 325) | GGAACAUGCUGAGG GGGGUG (SEQ ID NO: 403) |
| Exon 11 - 80 | CCCTCAGCATGTTC CCTGGA (SEQ ID NO: 248) | TCCAGGGAACATGC TGAGGG (SEQ ID NO: 326) | UCCAGGGAACAUGC UGAGGG (SEQ ID NO: 404) |
| Exon 11 - 75 | AGCATGTTCCCTGG AAGCTG (SEQ ID NO: 249) | CAGCTTCCAGGGAA CATGCT (SEQ ID NO: 327) | CAGCUUCCAGGGAA CAUGCU (SEQ ID NO: 405) |
| Exon 11 - 70 | GTTCCCTGGAAGCT GAGGGT (SEQ ID NO: 250) | ACCCTCAGCTTCCA GGGAAC (SEQ ID NO: 328) | ACCCUCAGCUUCCA GGGAAC (SEQ ID NO: 406) |
| Exon 11 - 65 | CTGGAAGCTGAGGG TCTCTG (SEQ ID NO: 251) | CAGAGACCCTCAGC TTCCAG (SEQ ID NO: 329) | CAGAGACCCUCAGC UUCCAG (SEQ ID NO: 407) |
| Exon 11 - 60 | AGCTGAGGGTCTCT GGGGCT (SEQ ID NO: 252) | AGCCCCAGAGACCC TCAGCT (SEQ ID NO: 330) | AGCCCCAGAGACCC UCAGCU (SEQ ID NO: 408) |
| Exon 11 - 55 | AGGGTCTCTGGGGC TCAGTC (SEQ ID NO: 253) | GACTGAGCCCCAGA GACCCT (SEQ ID NO: 331) | GACUGAGCCCCAGA GACCCU (SEQ ID NO: 409) |
| Exon 11 - 50 | CTCTGGGGCTCAGT CCCGGT (SEQ ID NO: 254) | ACCGGGACTGAGCC CCAGAG (SEQ ID NO: 332) | ACCGGGACUGAGCC CCAGAG (SEQ ID NO: 410) |
| Exon 11 - 45 | GGGCTCAGTCCCGG TCTCTC (SEQ ID NO: 255) | GAGAGACCGGGACT GAGCCC (SEQ ID NO: 333) | GAGAGACCGGGACU GAGCCC (SEQ ID NO: 411) |
| Exon 11 - 40 | CAGTCCCGGTCTCT CTCTTT (SEQ ID NO: 256) | AAAGAGAGAGACCG GGACTG (SEQ ID NO: 334) | AAAGAGAGAGACCG GGACUG (SEQ ID NO: 412) |
| Exon 11 - 35 | CCGGTCTCTCTCTTT CTCTC (SEQ ID NO: 257) | GAGAGAAAGAGAG AGACCGG (SEQ ID NO: 335) | GAGAGAAAGAGAG AGACCGG (SEQ ID NO: 413) |
| Exon 11 - 30 | CTCTCTCTTTCTCTC TCTCT (SEQ ID NO: 258) | AGAGAGAGAGAAA GAGAGAG (SEQ ID NO: 336) | AGAGAGAGAGAAA GAGAGAG (SEQ ID NO: 414) |
| Exon 11 - 25 | TCTTTCTCTCTCTCT CTCTC (SEQ ID NO: 259) | GAGAGAGAGAGAG AGAAAGA (SEQ ID NO: 337) | GAGAGAGAGAGAG AGAAAGA (SEQ ID NO: 415) |
| Exon 11 - 20 | CTCTCTCTCTCTCTC TGTCT (SEQ ID NO: 260) | AGACAGAGAGAGAG AGAGAG (SEQ ID NO: 338) | AGACAGAGAGAGAG AGAGAG (SEQ ID NO: 416) |
| Exon 11 - 15 | TCTCTCTCTCTGTCT CCCCG (SEQ ID NO: 261) | CGGGGAGACAGAGA GAGAGA (SEQ ID NO: 339) | CGGGGAGACAGAGA GAGAGA (SEQ ID NO: 417) |
| Exon 11 - 10 | CTCTCTGTCTCCCCG ACCCT (SEQ ID NO: 262) | AGGGTCGGGGAGAC AGAGAG (SEQ ID NO: 340) | AGGGUCGGGGAGAC AGAGAG (SEQ ID NO: 418) |
| Exon 11 - 5 | TGTCTCCCCGACCC TTCCCC (SEQ ID NO: 263) | GGGGAAGGGTCGGG GAGACA (SEQ ID NO: 341) | GGGGAAGGGUCGGG GAGACA (SEQ ID NO: 419) |
| Exon 11 - 0 | CCCCGACCCTTCCC CCCAGC (SEQ ID NO: 264) | GCTGGGGGAAGGG TCGGGG (SEQ ID NO: 342) | GCUGGGGGAAGGG UCGGGG (SEQ ID NO: 420) |
| Exon 11 - 5 | ACCCTTCCCCCCAG CGTGTT (SEQ ID NO: 265) | AACACGCTGGGGGG AAGGGT (SEQ ID NO: 343) | AACACGCUGGGGGG AAGGGU (SEQ ID NO: 421) |

TABLE 5-continued

ASO targets for Exon 11.

| ASO name | ASO Target sequence | ASO sequence (DNA) | ASO sequence (RNA) |
| --- | --- | --- | --- |
| Exon 11 − 10 | TCCCCCCAGCGTGT TCCCGA (SEQ ID NO: 266) | TCGGGAACACGCTG GGGGGA (SEQ ID NO: 344) | UCGGGAACACGCUG GGGGGA (SEQ ID NO: 422) |
| Exon 11 − 15 | CCAGCGTGTTCCCG AGGGAG (SEQ ID NO: 267) | CTCCCTCGGGAACA CGCTGG (SEQ ID NO: 345) | CUCCCUCGGGAACA CGCUGG (SEQ ID NO: 423) |
| Exon 11 + 1 | GTGTTCCCGAGGGA GCTGAA (SEQ ID NO: 268) | TTCAGCTCCCTCGGG AACAC (SEQ ID NO: 346) | UUCAGCUCCCUCGG GAACAC (SEQ ID NO: 424) |
| Exon 11 + 6 | CCCGAGGGAGCTGA AGGAGG (SEQ ID NO: 269) | CCTCCTTCAGCTCCC TCGGG (SEQ ID NO: 347) | CCUCCUUCAGCUCC CUCGGG (SEQ ID NO: 425) |
| Exon 11 + 11 | GGGAGCTGAAGGA GGTGTTT (SEQ ID NO: 270) | AAACACCTCCTTCA GCTCCC (SEQ ID NO: 348) | AAACACCUCCUUCA GCUCCC (SEQ ID NO: 426) |
| Exon 11 + 16 | CTGAAGGAGGTGTT TGCTTC (SEQ ID NO: 271) | GAAGCAAACACCTC CTTCAG (SEQ ID NO: 349) | GAAGCAAACACCUC CUUCAG (SEQ ID NO: 427) |
| Exon 11 + 21 | GGAGGTGTTTGCTT CGTGGC (SEQ ID NO: 272) | GCCACGAAGCAAAC ACCTCC (SEQ ID NO: 350) | GCCACGAAGCAAAC ACCUCC (SEQ ID NO: 428) |
| Exon 11 + 26 | TGTTTGCTTCGTGG CGGCTG (SEQ ID NO: 273) | CAGCCGCCACGAAG CAAACA (SEQ ID NO: 351) | CAGCCGCCACGAAG CAAACA (SEQ ID NO: 429) |
| Exon 11 + 31 | GCTTCGTGGCGGCT GCGCTG (SEQ ID NO: 274) | CAGCGCAGCCGCCA CGAAGC (SEQ ID NO: 352) | CAGCGCAGCCGCCA CGAAGC (SEQ ID NO: 430) |
| Exon 11 + 36 | GTGGCGGCTGCGCT GCGCAG (SEQ ID NO: 275) | CTGCGCAGCGCAGC CGCCAC (SEQ ID NO: 353) | CUGCGCAGCGCAGC CGCCAC (SEQ ID NO: 431) |
| Exon 11 + 41 | GGCTGCGCTGCGCA GAGCGA (SEQ ID NO: 276) | TCGCTCTGCGCAGC GCAGCC (SEQ ID NO: 354) | UCGCUCUGCGCAGC GCAGCC (SEQ ID NO: 432) |
| Exon 11 + 46 | CGCTGCGCAGAGCG AGGCCG (SEQ ID NO: 277) | CGGCCTCGCTCTGC GCAGCG (SEQ ID NO: 355) | CGGCCUCGCUCUGC GCAGCG (SEQ ID NO: 433) |
| Exon 11 + 51 | CGCAGAGCGAGGCC GGGAGG (SEQ ID NO: 278) | CCTCCCGGCCTCGCT CTGCG (SEQ ID NO: 356) | CCUCCCGGCCUCGC UCUGCG (SEQ ID NO: 434) |
| Exon 11 + 56 | AGCGAGGCCGGGA GGACATC (SEQ ID NO: 279) | GATGTCCTCCCGGC CTCGCT (SEQ ID NO: 357) | GAUGUCCUCCCGGC CUCGCU (SEQ ID NO: 435) |
| Exon 11 + 61 | GGCCGGGAGGACAT CGCAGA (SEQ ID NO: 280) | TCTGCGATGTCCTCC CGGCC (SEQ ID NO: 358) | UCUGCGAUGUCCUC CCGGCC (SEQ ID NO: 436) |
| Exon 11 + 66 | GGAGGACATCGCAG ACAGGC (SEQ ID NO: 281) | GCCTGTCTGCGATGT CCTCC (SEQ ID NO: 359) | GCCUGUCUGCGAUG UCCUCC (SEQ ID NO: 437) |
| Exon 11 + 71 | ACATCGCAGACAGG CTTATC (SEQ ID NO: 282) | GATAAGCCTGTCTG CGATGT (SEQ ID NO: 360) | GAUAAGCCUGUCUG CGAUGU (SEQ ID NO: 438) |
| Exon 11 + 76 | GCAGACAGGCTTAT CAGCGC (SEQ ID NO: 283) | GCGCTGATAAGCCT GTCTGC (SEQ ID NO: 361) | GCGCUGAUAAGCCU GUCUGC (SEQ ID NO: 439) |
| Exon 11 + 81 | CAGGCTTATCAGCG CCTCAC (SEQ ID NO: 284) | GTGAGGCGCTGATA AGCCTG (SEQ ID NO: 362) | GUGAGGCGCUGAUA AGCCUG (SEQ ID NO: 440) |

TABLE 5-continued

ASO targets for Exon 11.

| ASO name | ASO Target sequence | ASO sequence (DNA) | ASO sequence (RNA) |
| --- | --- | --- | --- |
| Exon 11 + 86 | TTATCAGCGCCTCA CTCTTC (SEQ ID NO: 285) | GAAGAGTGAGGCGC TGATAA (SEQ ID NO: 363) | GAAGAGUGAGGCGC UGAUAA (SEQ ID NO: 441) |
| Exon 11 + 91 | AGCGCCTCACTCTT CCTGCG (SEQ ID NO: 286) | CGCAGGAAGAGTGA GGCGCT (SEQ ID NO: 364) | CGCAGGAAGAGUGA GGCGCU (SEQ ID NO: 442) |
| Exon 11 + 96 | CTCACTCTTCCTGC GCTTCC (SEQ ID NO: 287) | GGAAGCGCAGGAAG AGTGAG (SEQ ID NO: 365) | GGAAGCGCAGGAAG AGUGAG (SEQ ID NO: 443) |
| Exon 11 + 101 | TCTTCCTGCGCTTCC TCTGC (SEQ ID NO: 288) | GCAGAGGAAGCGCA GGAAGA (SEQ ID NO: 366) | GCAGAGGAAGCGCA GGAAGA (SEQ ID NO: 444) |
| Exon 11 + 106 | CTGCGCTTCCTCTG CCCAGC (SEQ ID NO: 289) | GCTGGGCAGAGGAA GCGCAG (SEQ ID NO: 367) | GCUGGGCAGAGGAA GCGCAG (SEQ ID NO: 445) |
| Exon 11 + 111 | CTTCCTCTGCCCAG CGATTA (SEQ ID NO: 290) | TAATCGCTGGGCAG AGGAAG (SEQ ID NO: 368) | UAAUCGCUGGGCAG AGGAAG (SEQ ID NO: 446) |
| Exon 11 + 116 | TCTGCCCAGCGATT ATGTCG (SEQ ID NO: 291) | CGACATAATCGCTG GGCAGA (SEQ ID NO: 369) | CGACAUAAUCGCUG GGCAGA (SEQ ID NO: 447) |
| Exon 11 + 121 | CCAGCGATTATGTC GCCCAG (SEQ ID NO: 292) | CTGGGCGACATAAT CGCTGG (SEQ ID NO: 370) | CUGGGCGACAUAAU CGCUGG (SEQ ID NO: 448) |
| Exon 11 + 126 | GATTATGTCGCCCA GTCTCT (SEQ ID NO: 293) | AGAGACTGGGCGAC ATAATC (SEQ ID NO: 371) | AGAGACUGGGCGAC AUAAUC (SEQ ID NO: 449) |
| Exon 11 + 131 | TGTCGCCCAGTCTC TTTGGG (SEQ ID NO: 294) | CCCAAAGAGACTGG GCGACA (SEQ ID NO: 372) | CCCAAAGAGACUGG GCGACA (SEQ ID NO: 450) |

As shown in Table 6, positive and negative control ASOs are disclosed herein. Also disclosed herein are RNA sequences of the positive and negative control ASOs and the positive and negative control ASO target sequences. In some aspects, the positive control ASO comprises SEQ ID NO:452. In some aspects, the positive control ASO RNA comprises SEQ ID NO:454. In some aspects, the positive control ASO targets a sequence comprising SEQ ID NO:451.

In some aspects, the negative control ASO comprises SEQ ID NO:453. In some aspects, the positive control ASO RNA comprises SEQ ID NO:455.

In some aspects, the ASO is expressed in a plasmid or vector. In some aspects, the ASO is expressed as a naked oligo. In some aspects, the ASO is expressed as a double-stranded oligonucleotide. In some aspects, the ASO is expressed as a single-stranded oligonucleotide.

In some embodiments, the present disclosure provides recombinant vectors including the polynucleotides or the fragments or derivatives thereof. In some embodiments, the recombinant vector is capable of propagating the isolated polynucleotide in a suitable prokaryotic or eukaryotic host cell. In some embodiments, recombinant vectors are capable of expressing an isolated polynucleotide as RNA, e.g., mRNA, in a suitable cell expression system. The recombinant vector can include nearly any number of useful elements, however in most cases the vector will include control elements operably linked to the inserted nucleic acid (e.g.,

TABLE 6

Control ASO sequences.

| ASO name | ASO Target sequence | ASO sequence (DNA) | ASO sequence (RNA) |
| --- | --- | --- | --- |
| Nusinersen (positive control) | CCAGCATTATGA AAG (SEQ ID NO: 451) | TCACTTTCATAATGCT GG (SEQ ID NO: 452) | UCACUUUCAUAAUGC UGG (SEQ ID NO: 454) |
| negative control ASO | | GCGACTATACGCGCA AUAUG (SEQ ID NO: 453) | GCGACUAUACGCGCA AUAUG (SEQ ID NO: 455) | promoter, leader, and/or enhancer elements) which control elements can be selected to optimize replication and/or transcription of the vector in the cells.

In some embodiments, provided herein are cultured host cells which have been transformed, transfected or infected either transiently or stably by at least one recombinant vector of the disclosure which vector includes an isolated polynucleotide as disclosed herein.

Recombinant vectors of the disclosure can be introduced into suitable cells or groups of such cells including tissue or organs if desired either in vitro or in vivo. In some embodiments, the cells are capable of expressing the recombinant vector at detectable levels. Host cells including the vectors can be cultured in medium capable of supporting propagation and/or expression of the vectors in the cells. The cells can be eukaryotic cells. In some aspects, the cells are mammalian cells such as neurons and neuron-associated cells (e.g., glia) which cells are capable of expressing desired sequences in the recombinant vector. The cells can be primary cells or the cells can be immortalized. In some aspects, the cells are HEK 293 cells. In some instances, the vector is introduced into a suitable prokaryotic host e.g., bacteria, insect, yeast or fungal cells to propagate the vector.

In some embodiments, provided herein is a pharmaceutically acceptable composition including an agent, wherein the agent is capable of increasing the expression and/or activity of SynGAP1. In some aspects, the pharmaceutical composition is in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Such compositions may be prepared for use in parenteral administration, to particularly in the form of liquid solutions or suspensions; for oral administration, particularly in the form of tablets or capsules; intranasally, particularly in the form of powders, nasal drops, or aerosols; vaginally; topically e.g., in the form of a cream; rectally e.g., as a suppository; etc.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain of the compounds.

Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Other delivery systems will administer the therapeutic agent(s) directly, e.g., by use of stents.

A composition of this disclosure can be employed in the present treatment methods as the sole active pharmaceutical agent or can be used in combination with other active ingredients, e.g., those compounds known in the field to be useful in the treatment of cognitive and neurological disorders.

The concentration of one or more treatment compounds in a therapeutic composition will vary depending upon a number of factors, including the dosage of the therapeutic compound to be administered, the chemical characteristics (e.g., hydrophobicity) of the composition employed, and the intended mode and route of administration. In general, one or more than one of the therapeutic compounds is compounds may be provided in an aqueous physiological buffer solution containing about 0.1 to 10% w/v of a compound for parenteral administration. As noted above, GAPYSN antibodies and antigen-binding fragments thereof can be modified according to standard methods to deliver useful molecules or can be modified to include detectable labels and tags to facilitate visualization of synapses including SYNGAP.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject.

EXAMPLES

The disclosure is further described in the following examples, which do not limit the scope of the disclosure described in the claims.

Example 1: SynGAP Isoforms are Differentially Distributed During Brain Development SYNGAP1 is alternatively spliced within exons 18-20 to generate four unique C-terminal isoforms designated as α1, α2, β, and γ (FIGS. 1A, 1B). The α isoforms are produced by alternative splicing of exon 20, resulting in a PDZ ligand (-QTRV)-containing α1 isoform and a PDZ ligand-lacking α2 isoform. The γ isoform is generated by the inclusion of exon 19, which contains a short coding sequence followed by a STOP codon (-LLIR*). The β isoform is generated through alternative splicing of exon 18, which results in an isoform with a partially truncated coiled-coil domain.

To characterize each SynGAP isoform, isoform-specific antibodies using various SynGAP C-terminal peptides as antigens were raised (FIG. 1B, black underlines).

Procedurally, all restriction enzymes were obtained from New England Biolabs. Chemicals were obtained from SIGMA-Aldrich unless otherwise specified. TTX, Bicuculline, and Strychnine were obtained from TOCRIS Bioscience. Goat anti-SynGAP α1 antibody is from Santa Cruz (sc-8572). Rabbit pan-SynGAP 947-1167 antibody is from Thermo scientific (#PA-1-046). DNA sequencing was performed at the Johns Hopkins University School of Medicine Sequencing Facility. Rabbit anti-SynGAP α1 antibody was used as described in previous reports (Kim et al., 1998; Rumbaugh et al., 2006). To raise antibodies that specifically recognize each non-α1 SynGAP isoform, 10-18 amino acids of the C-terminal sequences of each SynGAP isoform was conjugated with an N-terminal Cysteine (CP-PRLQITENGEFRNTADH (JH7265, α2), CGGGGAAPGP-PRHG (JH7266, β), and CRLLDAQLLIR (JH7366, γ)) to Keyhole limpet hemocyanin (PIERCE) using the manufacturer's protocol. Anti-SynGAP γ antisera bleeding batches were extensively screened to identify batches with high antigen sensitivity. Antisera acquired after 1-2 booster injections (α1, α2, and β) or 5-6 booster injections (γ) were affinity purified using peptide coupling sulfo-beads (PIERCE).

Figure 1F:
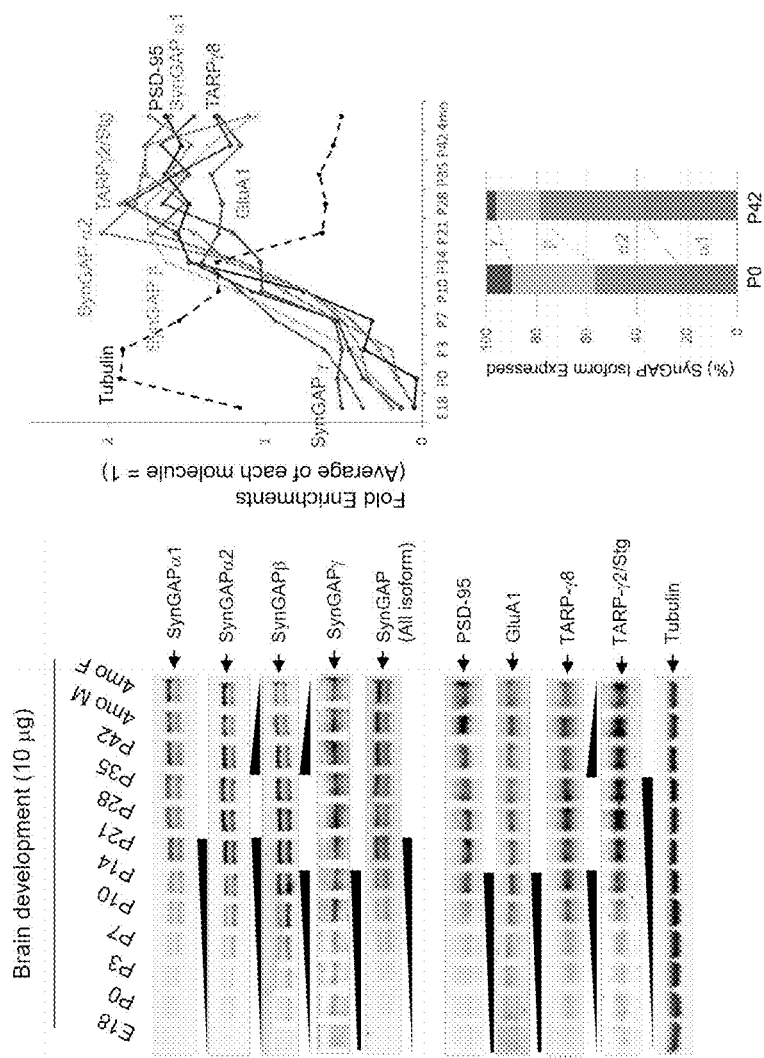
FIG. 1F shows developmental profile of SynGAP isoforms and related synaptic proteins in brain. Absolute composition of each SynGAP isoform during development was calculated using data from FIG. 1C and this developmental profile. Note that SynGAP $\alpha$1 comprises only ~25% of total SynGAP at P0, and is increased in mature brain. SynGAP $\beta$ was enriched earlier in development.

Antibodies specific to each isoforms were expressed in HEK cells (FIG. 1C, Left 4 lanes) and specific bands in mouse brain were detected (FIG. 1C, Right 2 lanes). SYN-GAP1 Het (+/−) mice showed ~50% of band intensity, implicating specificity of these antibodies. All four SynGAP isoforms were observed to be expressed in brain tissue (asterisks: non-specific band, also shown in SYNGAP Het mice brain tissue) together with other brain-specific proteins, such as Stargazin and TARP-γ8 (FIG. 1D). In order to characterize the distribution of SynGAP isoforms across brain regions, 8 different brain regions from adult (P42) mice were isolated. All four SynGAP isoforms were enriched in forebrain regions (mainly in cerebral cortex and hippocampus), along with synaptic proteins such as GluA1, PSD-95, Stargazin, and TARP-γ8 (FIG. 1E). SynGAP β and γ were also expressed in the olfactory bulb. Of note, SynGAP γ was observed in the cerebellum, together with Stargazin-TARP/γ-2, and AMPARs. SynGAP mutations have been linked to NDDs, such as ID and ASD, suggesting a role for SynGAP in brain development. In order to investigate the expression patterns of the various SynGAP isoforms throughout development, brain tissue from mice were collected at several developmental stages (FIG. 1F). SynGAP β and γ are expressed early in development (E18-P14). SynGAP α2 levels are low early in development, but reach their maximum from P21 to P35. SynGAP α1 reaches maximum expression level by P35 and through P42. High-level expression of SynGAP α1 remains constant during adulthood (FIG. 1F). The expression of other synaptic proteins (GluA1, PSD-95, and TARPs) reached maximum between P21 and P42, which is similar to the timeframe for maximal expression of SynGAP α1 and α2.

In order to more rigorously quantify the expression levels of the various isoforms over development, the relative composition (% total SynGAP) of each SynGAP isoform over development was estimated using Western blot data in FIG. 1B. Pan-SynGAP 947-1167 (PA1-046) antibody presumably equally detects each SynGAP isoform at P42 due to conservation of the antibody epitope across isoforms. As such, isoform-specific antibody signal in HEK cells and in mouse brains was compared to that of pan-SynGAP antibody, which represents total SynGAP. The isoform composition at P0 from P42 composition was calculated using the information of developmental isoform dynamics obtained in FIG. 1F. SynGAP β is the most abundant isoform (34.6±0.6%) at P0, but decreased to 15.7±0.8% at P42. SynGAP α1 is a minor isoform (24.3±0.3%) at P0, and becomes an increasingly prominent isoform over development. At P42, SynGAP α1 is the second most highly expressed isoform (35.0±0.9%) only behind SynGAP α2 (44.9±1.5%). SynGAP γ is a very minorly expressed isoform all throughout development (9.1±0.5% at P0, and 4.3±0.3% at P42) (FIG. 1F). These results suggest that the developmental regulation of SynGAP expression is complex and isoform-specific, underscoring the need to characterize the properties of all SynGAP structural isoforms for a more precise understanding of SYNGAP1-related pathogenesis.

Example 2: Unique Liquid-Liquid Phase Separation (LLPS) Properties of SynGAP Isoforms Correlates with its Post-Synaptic Density Vs. Cytosolic Localization in the Mouse Brain Previously, it was shown that SynGAP α1 undergoes LLPS with PSD-95 at physiological concentrations (in μM order) in vitro, resulting in concentration of SynGAP in dense condensates, reminiscent of the postsynaptic density (Zeng et al., 2016). To investigate the biochemical and phase separation properties of other SynGAP isoforms, a sedimentation assay first was performed (FIG. 2A).

HEK 293T cells were transfected with SynGAP and/or PSD-95 for 16 h. Cells were lysed in 0.5 ml of assay buffer (50 mM Tris pH 8.0, 100 mM NaCl, 1 mM EDTA, 1 mM EGTA, 1% Triton X-100, 0.1% SDS, 0.5% Sodium deoxycholate, with complete Protease inhibitor EDTA-free mix (SIGMA)). Lysates were centrifuged at 15000×g for 10 min at 4° C. The supernatant containing the soluble [S] fraction was collected. Pellets were resuspended and sonicated in 0.5 ml of Assay buffer to obtain complete homogenate of pellet [P] fraction.

Fractionation of post-synaptic density (PSD) was performed as previously described (Kohmura et al., 1998). In brief, mouse brains were collected and homogenized by 10-15 strokes of a Dounce A homogenizer in Buffer A (0.32M Sucrose, 10 mM Hepes (pH7.4) with complete protease inhibitor mix (SIGMA)). The homogenate was centrifuged at 1,000×g for 10 min at 4° C. The supernatant (Post Nuclear Supernatant; PNS) was collected and centrifuged at 13,800×g for 20 min at 4° C. The pellet (P2 fraction) was re-homogenized in 3 volumes of Buffer A. The rehomogenized P2 fraction was layered onto a discontinuous gradient of 0.85, 1.0, 1.2 M sucrose (all containing 10 mM Hepes (pH7.4) plus complete protease inhibitor mix), and were centrifuged at 82,500×g for 2 h at 4° C. (Beckman SW28 swing rotor). The band between 1.0 and 1.2 M sucrose was collected as the synaptosome fraction and diluted with 80 mM Tris-HCl (pH 8.0). An equal volume of 1% Triton X-100 was added and rotated for 15 min at 4° C. followed by centrifuging 32,000×g for 20 min. The supernatant was collected as Triton-soluble synaptosome (Syn/Tx) fraction and the pellet was re-homogenized in Buffer A by 10 passes through a 21 G syringe. Equal amounts of protein (10 μg for immunoblotting) were used for further assay.

Phase separated fraction [P] were centrifuged and recovered as a pellet in assay buffer, while soluble fraction were recovered in supernatant [S] fraction. The ratio of how much each protein went to condensed phase fractions ([P]/([S]+[P])) was calculated and displayed in graph as an indicator of LLPS propensity. Both myc-PSD-95 and GFP-SynGAP WT remain in the soluble fraction when expressed singly (FIGS. 2B, 2C). When co-expressed, the levels of both myc-PSD-95 and GFP-SynGAP α1 WT are dramatically increased in phase separated [P] fraction. When an LLPS mutant of GFP-SynGAP α1 LDKD (L1202D/K1252D) was used, co-sedimentation of SynGAP α1 LDKD with PSD-95 was significantly decreased compared to that of GFP-SynGAP α1 WT with PSD-95 (FIGS. 2B, 2C). These data are consistent with the results of in vitro cell-free sedimentation assay experiments reported previously, although here full-length protein in living cells was used. In previous experiments, partial length protein was used in vitro.

Next, the PSD-95-dependent LLPS propensity of each SynGAP isoform was examined (FIGS. 2D, 2E). When expressed singly, each of the four isoforms was found to be present predominantly in the soluble fraction. Co-expression with PSD-95 dramatically increased the phase separated fraction of both GFP-SynGAP α1 and myc-PSD-95, while GFP-SynGAP β and myc-PSD-95 did not efficiently co-sediment. GFP-SynGAP α2 and γ also exhibited a decrease in pellet fraction, but to a lower magnitude than that of α1 (FIGS. 2D, 2E). These results highlight the necessity of both the coiled-coil domain and PDZ ligand for strongest LLPS: The β isoform lacks a PDZ ligand and contains a partial coiled-coil domain (exhibiting the weakest LLPS), while α2 and γ each harbor a complete coiled-coil domain, but lack a PDZ ligand (exhibiting marginal LLPS).

Next, SynGAP isoform-dependent biomolecular condensate formation in living cells was assessed using confocal microscopy (FIGS. 2F, 2G). For imaging of LLPS dynamics in live cells, HEK cells were grown on Poly-L-Lysinecoated glass coverslips. Cells were transfected with GFP-SynGAP and/or PSD-95-mCherry for 16 h before being placed in a custom-made live imaging chamber for observation under confocal microscopy. Cells were perfused with extracellular solution (ECS: 143 mM NaCl, 5 mM KCl, 10 mM Hepes pH 7.42, 10 mM Glucose, 2 mM $CaCl_2$, 1 mM $MgCl_2$). For DAPI staining, cells were fixed with Parafix (4% paraformaldehyde, 4% Sucrose in PBS) for 15 min at room temperature, followed by incubating with 300 nM DAPI in PBS for 5 min at room temperature. Cells were briefly washed with PBS and mounted on a slide. Cells were observed on an LSM880 (Zeiss) microscopy with a 40× objective lens (NA 1.3).

Previously, it was reported that GFP-SynGAP α1 and RFP-PSD-95 undergo phase transition in living cells and form liquid-like cytoplasmic droplets when expressed in living cells (Zeng et al., 2016). When expressed singly in HEK 293T cells, GFP-SynGAP α1 and PSD95-mCherry (PSD95-mCh) exhibited relatively diffuse cytoplasmic expression. Co-expression of PSD95-mCh and GFP-SynGAP α1 WT dramatically generated distinct cytoplasmic puncta (diameters greater than 1 μm), while phase separation mutant GFP-SynGAP α1 LDKD did not induce puncta formation when co-expressed with PSD-95-mCh (FIG. 2F). It was next determined the percentage of cytoplasmic puncta-positive cells following co-expression of PSD-95-mCh along with each SynGAP isoform. SynGAP α1 expression robustly induced distinct puncta with PSD95 in cells, but non-α1 isoforms failed to do so. The failure of non-α1 isoforms to induce the formation of measurable cytoplasmic puncta suggests that a complete coiled-coil domain and PDZ-ligand are required for creating distinct condensed phase in this assay. These results suggest that SynGAP isoforms have unique biochemical/LLPS properties determined by its unique C terminal sequences—such like α1 with strongest LLPS, while β isoform with weakest LLPS propensity but is more accessible to cytoplasmic biomolecules as β has no PDZ ligand with partial coiled-coil domain.

Example 3: SynGAP Isoforms Differentially Regulate GTPase Activity to Ras, Rap1, and Rac1

Next, the differences in GAP activity between SynGAP isoforms were investigated. Following co-transfection of cells with a single SynGAP isoform along with small G proteins, levels of GTP bound small G proteins were assayed. Decreases in each small GTPases (Ras, Rap1, Rac1) by coexpressing SynGAP isoforms compared to no SynGAP cotransfection were examined.

Small GTPase activity was measured using a small GTPase-GTP pull down assay. HEK cells were co-transfected with a small G protein and a single SynGAP isoform construct for 48-72 hours. Active Ras levels were then assayed using Ras activation assay kit (EMD Millipore). In brief, cells were lysed in Mg2+ lysis/wash buffer (25 mM HEPES pH 7.5, 150 mM NaCl, 1% Igepal CA-630, 10 mM $MgCl_2$, 1 mM EDTA, 10% glycerol) and active GTP-bound small G proteins were pulled down using beads covalently bound to effector domains. After washing beads, active GTP-bound small G proteins were recovered through the addition of 2×SDS sample buffer followed by SDSPAGE and immunoblotting for the various small G proteins tested.

Figure 3D:
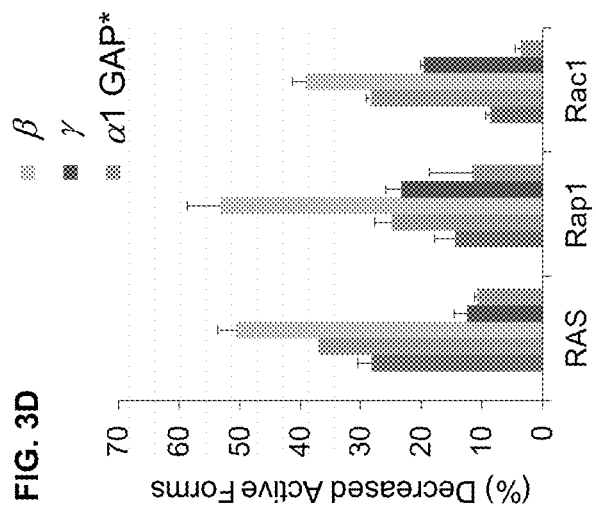
FIG. 3D shows decreased active amounts or Ras, Rap1, and Rac1 among various isoforms.
Figure 3A:
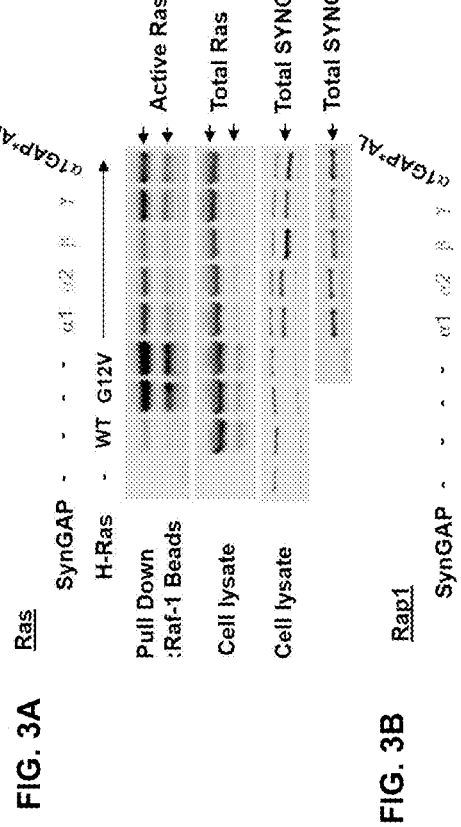
FIG. 3A shows exemplary SynGAP isoforms differentially regulate the activity of various small G proteins. Assay of the effect of various SynGAP isoforms on the activity of small G proteins, including Ras. Active GTP-bound forms of each small G protein were precipitated using beads covalently coupled with their effector domains. Percent reduction of GTP-bound forms of each small G protein by the co-expression of various SynGAP isoforms is shown, normalized to total SynGAP expression level (standardized by soluble SynGAP amount, N=4, *P<0.001, P<0.01, One-way ANOVA followed by Tukey test). Note that SynGAP $\beta$ generally exhibits the highest GAP activity levels among all isoforms tested, while SynGAP $\alpha$1 has a moderate preference towards Ras.
Figure 3B:
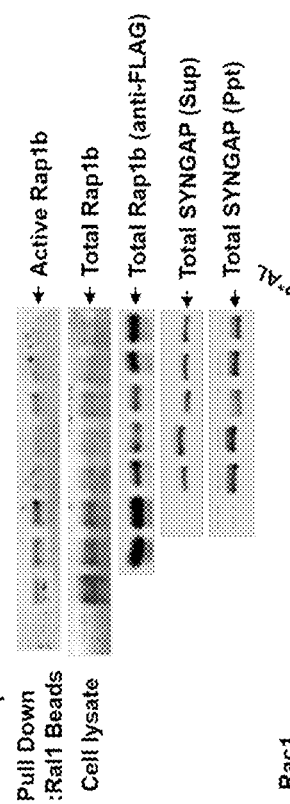
FIG. 3B shows exemplary SynGAP isoforms differentially regulate the activity of various small G proteins. Assay of the effect of various SynGAP isoforms on the activity of small G proteins, including Rap1.
Figure 3C:
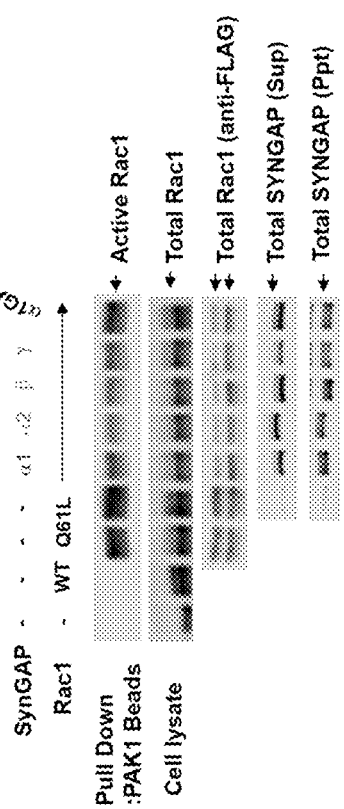
FIG. 3C shows exemplary SynGAP isoforms differentially regulate the activity of various small G proteins. Assay of the effect of various SynGAP isoforms on the activity of small G proteins, including Rac1.

As shown in FIGS. 3A-3C, co-expression of SynGAP differentially reduced GTP (active) forms of each small G protein. FIG. 3D shows how much GTP forms were reduced with SynGAP transfections (Lanes 5-8) compared to small G protein alone (Lane 4) that is standardized by expression levels of soluble SynGAP. SynGAP β generally has highest GAP activity into all small G proteins among other isoforms. SynGAP α1 and α2 has mild preference towards Ras rather than Rap. SynGAP β and γ has mild preference towards Rap1. It is known that various small G proteins are differentially modified by lipids to target subdomains of biological membrane (Khosravi-Far et al., 1992; Magee and Marshall, 1999; Moores et al., 1991). Considering that SynGAP isoforms also are differentially form biological condensates to differentially localized in cells, it is conceivable that these unique localization of SynGAP isoforms and each small G proteins create the preferences of GAP activity of SynGAP isoforms to each small G protein. Since small G proteins were not phase separated, most soluble SynGAP isoform may have highest chances to react with small G proteins and thus have highest GAP activities. It is also possible that different C-terminal structure to enhance or decrease the access of various small G proteins to GAP domain and thus differentially regulating their GAP activity.

Example 4: SynGAP α1 was Dynamically Dispersed During Long-Term Potentiation (LTP) while Other Isoforms were Less Effectively Dispersed Previously, it was shown that SynGAP α1 undergoes rapid NMDAR-CaMKII-dependent dispersion from the synapse, which is required for AMPAR insertion and spine enlargement during LTP (Araki et al., 2015). In order to investigate the dispersion dynamics of the other SynGAP isoforms during LTP, a knockdown-replacement strategy, substituting endogenous SynGAP for each SynGAP isoform, was employed. Neurons were co-transfected with pSUPER-mCherry: shRNA SynGAP #5 to knock down endogenous SynGAP, and shRNA #5-resistant forms of each of the four GFP-SynGAP isoforms. These neurons then were subjected to chemically-induced LTP (200 μM Glycine, 0 Mg) during live confocal imaging.

Figure 2H:
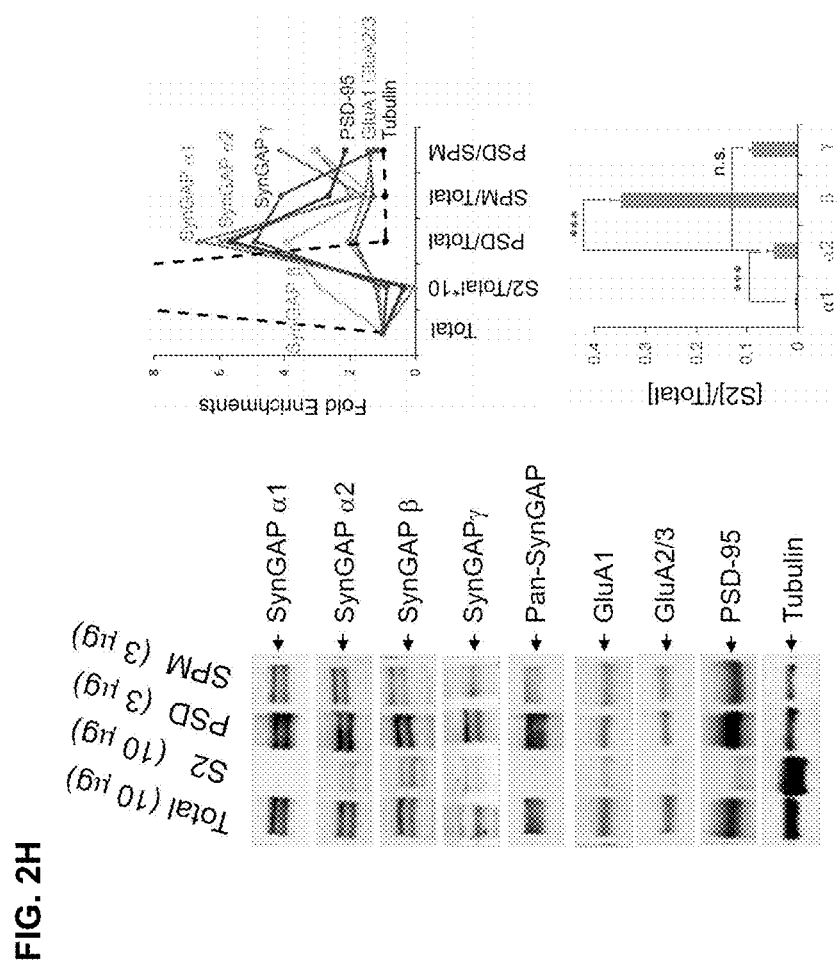
FIG. 2H shows PSD fractionation of adult mouse brain. Total homogenate, S2, Postsynaptic density (PSD), and synaptosomal membrane (SPM) were examined. Graphs indicate fold enrichment compared to Total fraction. Reminiscent of FIG. 2(A)-(G) biochemical properties, SynGAP $\alpha$1 was highly packed in detergent-insoluble PSD fractions, while SynGAP $\beta$ was less PSD-enriched PSD, and more enriched in S2. The S2 fraction content of all SynGAP isoforms tested are quantified displayed (Bottom right). Note that SynGAP $\alpha$1 is virtually absent from S2 in WT mouse brain (N=4 brains, *P<0.001, P<0.01, One-way ANOVA followed by Tukey test).

Procedurally, hippocampal neurons from embryonic day 18 (E18) rats were seeded on 25-mm poly-L-lysine-coated coverslips. The cells were plated in Neurobasal media (Gibco) containing 50 U/ml penicillin, 50 mg/ml streptomycin and 2 mM GlutaMax supplemented with 2% B27 (Gibco) and 5% horse serum (Hyclone). At DIVE, cells were thereafter maintained in glia-conditioned NM1 (Neurobasal media with 2 mM GlutaMax, 1% FBS, 2% B27, 1×FDU (5 mM Uridine (SIGMA F0503), 5 mM 5-Fluro-2'-deoxyuridine (SIGMA U3003). Cells were transfected at DIV17-19 with Lipofectamine 2000 (Invitrogen) in accordance with the manufacturer's manual. After 2 days, coverslips were placed on a custom-made perfusion chamber with basal ECS (143 mM NaCl, 5 mM KCl, 10 mM Hepes pH 7.42, 10 mM Glucose, 2 mM CaCl2, 1 mM MgCl2, 0.5 µM TTX, 1 µM Strychnine, 20 µM Bicuculline) and timelapse images were captured with either LSM510 (Carl Zeiss; FIGS. 1, 4, and 6) or Spinning disk confocal system controlled by axiovision software (Carl Zeiss; FIGS. 2, 3, and 5). Following 5-10 min of basal recording, cells were perfused with 10 ml of glycine/0 Mg ECS (143 mM NaCl, 5 mM KCl, 10 mM Hepes pH 7.42, 10 mM Glucose, 2 mM CaCl2, 0 mM MgCl2, 0.5 µM TTX, 1 µM Strychnine, 20 µM Bicuculline, 200 µM Glycine) for 10 min, followed by 10 ml of basal ECS. For chemical LTD, instead of Glycine solution, 10 ml of NMDA/0 Mg ECS (143 mM NaCl, 5 mM KCl, 10 mM Hepes pH 7.42, 10 mM Glucose, 2 mM CaCl2, 0 mM MgCl2, 1 µM TTX, 20 µM NMDA) was perfused for 5 min. To stabilize focus during long-term imaging, definite focus (Zeiss) was used. For quantification, pyramidal neurons based on morphology that consisted of a clear primary dendrite were selected, and all spines on the 30-40 µm stretch of the secondary dendrite beginning just after the branch from the primary dendrite were quantified. For identifying spine regions, the mCherry channel was used to select the spine region that is well separated from dendritic shaft. These regions of interest (ROIs) in the mCherry channel were transferred to the Green channel to quantify total SynGAP content in spines. An example was displayed in FIGS. 2G-2H. Total spine volume was calculated as follows; (Average Red signal at ROI-Average Red signal at Background region)*(Area of ROI). Total SynGAP content was calculated as follows; (Average Green signal at ROI-Average Green signal at Background region)*(Area of ROI). By doing this, the total signals at each spine can be precisely quantified even if the circled region contained some background area. For [%] spine enlargement before/after LTP, a relative ratio of these total spine volume (total red signal) of each spine before/after LTP ([%] spine enlargement=(Total Red Signal after chemLTP/Total Red signal at basal state-1)*100) was taken. For [%] SynGAP dispersion, the degree of total SynGAP content loss after chemLTP at each spine compared to the total SynGAP content at basal state was calculated ([%] dispersion=(1-Total Green Signal after chemLTP/Total Green signal at basal state)*100).

SynGAP α1 was highly synaptically enriched at baseline, and underwent rapid dispersion upon long-term potentiation (LTP) stimulation. As shown in FIG. 4A, dendritic spines in this condition were subsequently enlarged that represent structural plasticity of spines during LTP (Yellow arrows). GFP-SynGAP β at baseline was less synaptically enriched and more cytosolic, and did not efficiently undergo LTP-dependent dispersion. It was previously found that knockdown of SynGAP caused aberrant spine enlargement, which could be rescued by SynGAP α1 expression (Araki et al 2015). β isoform did not correct aberrant spine enlargements upon SynGAP knockdown. α2 and γ isoforms were marginal between α1 (strongest dispersion, strongest structural plasticity rescue) and β (no dispersion, no structural plasticity rescue). These results suggest that both the SynGAP coiled-coil domain and PDZ ligand are required for robust synaptic enrichment and dynamic dispersion upon LTP.

Figure 5A:
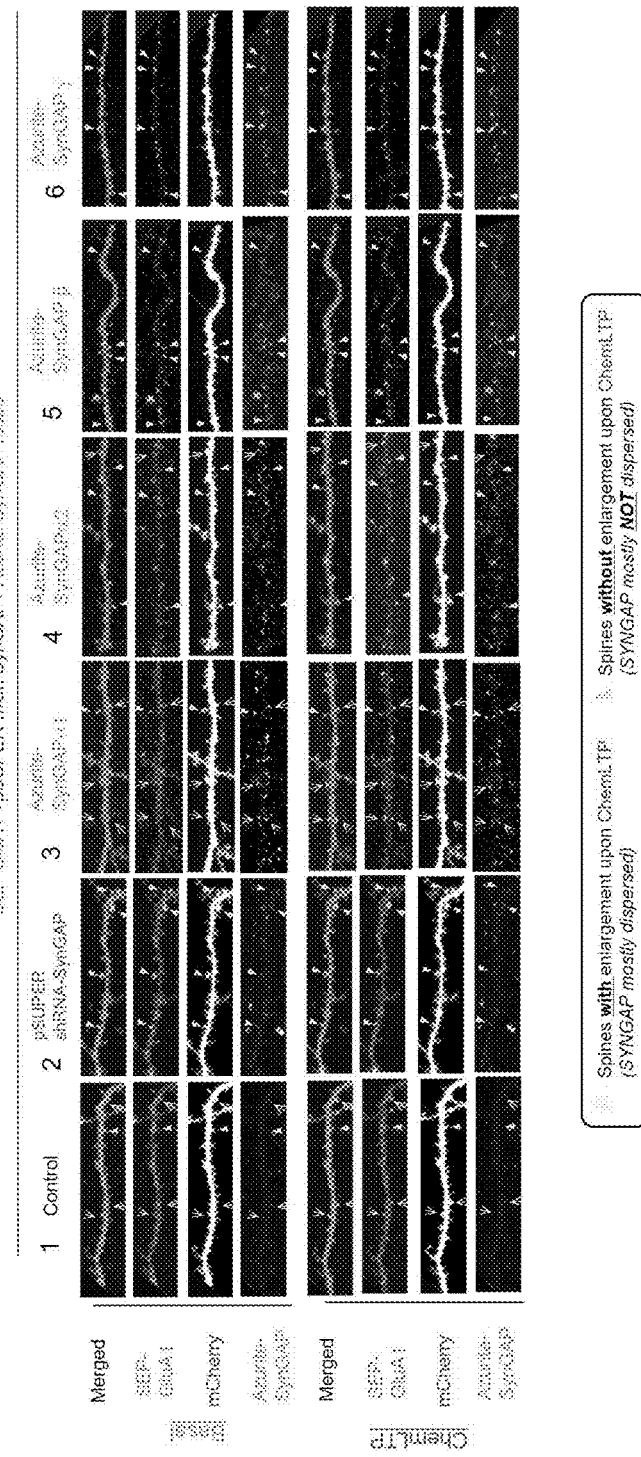
FIG. 5A shows exemplary SynGAP α1 rescues LTP deficits in SynGAP knockdown neurons. SynGAP α1 rescues plasticity-related deficits in cultured SynGAP knockdown neurons by live imaging of cells subjected to chemLTP. Neurons were transfected with SEP-GluA1 to monitor surface AMPAR accumulation at synapses, Azurite-tagged SynGAP isoforms to monitor changes in SynGAP localization, and mCherry to monitor morphological changes during chemLTP. Endogenous SynGAP was knocked down and rescued with Azurite-tagged SynGAP. (1) Control: Endogenous SynGAP was intact. Synaptic spines were enlarged and GluA1 was expressed synaptically (Yellow arrows). (2) SynGAP knockdown: Synaptic spines were enlarged and GluA1 was basally elevated compared to control, indicating occlusion of synaptic plasticity. (3) Azurite-SynGAP α1 rescue: SynGAP α1 was basally synaptically enriched, and rapidly dispersed upon chemLTP. Synaptic AMPAR accumulation and synaptic spine enlargement was rescued. (4) Azurite-SynGAP α2 rescue: SynGAP α2 was synaptically enriched, but less efficiently dispersed upon chemLTP. No significant rescue of knockdown-dependent AMPAR accumulation or synaptic spine enlargement was observed. (5, 6) Azurite β and γ rescue: SynGAP β and γ were less synaptically enriched, reminiscent of their biochemical properties.
Figure 5B:
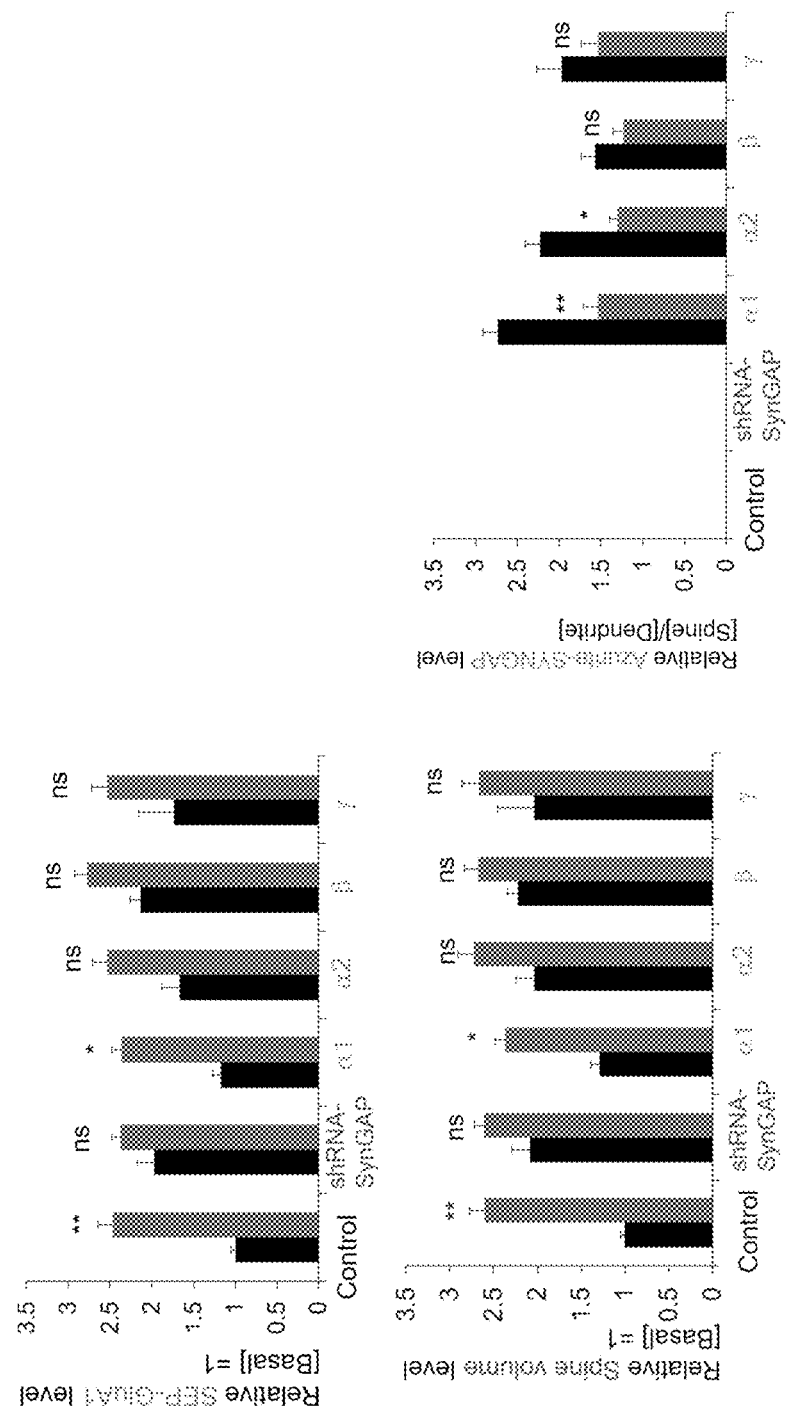
FIG. 5B provides graphs showing SynGAP α1 rescues LTP deficits in SynGAP knockdown neurons. No significant dispersion of SynGAP β or γ was observed upon chemLTP. Graphs quantifying SEP-GluA1 intensity (synaptic enrichment), mCherry signal volume (spine size), and Azurite-SynGAP content during LTP are shown (N=7 neurons in each condition, *P<0.001, P<0.01, One-way ANOVA followed by Tukey test).

Example 5: SynGAP α1 Specifically Rescues the Deficits in AMPAR Insertion During LTP in SynGAP KD Neurons SYNGAP1 heterozygous mice show severe deficits in LTP of hippocampal SC-CA1 synapses (Komiyama, Kim 2003). However, it is unclear whether this effect is due to the loss of a single isoform, or to a global reduction in the levels of all SynGAP isoforms. To test this, molecular replacement strategy similar to that described previously was employed. In brief, endogenous SynGAP by shRNA-SynGAP #5 was knocked down (Araki et al., 2015; Zeng et al., 2016) and was replaced with shRNA-resistant Azurite-tagged SynGAP isoforms. Super ecliptic fluorine (SEP) tagged-GluA1 and mCherry were co-transfected to monitor surface AMPAR and synaptic-spine dynamics during LTP (FIGS. 5A-5C). SEP is a pH-sensitive green fluorescent protein that preferably reports cell surface AMPARs (Lin et al., 2009). Under control conditions, AMPARs were inserted and synaptic spines were enlarged after stimulation (Yellow arrows, FIG. 5A, window 1 and FIG. 5B). Knockdown of endogenous SynGAP caused aberrant spine enlargement and synaptic AMPAR accumulation at basal state, and no further spine enlargement or AMPAR insertion was observed following stimulation (Blue arrowheads, FIG. 5A, window 2 and FIG. 5B). SynGAP α1 expression rescued this pan-SynGAP knockdown phenotype; in the presence of SynGAP α1, synaptic spines underwent LTP dependent enhancement of size and surface AMPAR content (Yellow arrows, FIG. 5A, window 3, and FIG. 5B). SynGAP β and γ, did not rescue knockdown-induced basal spine enlargement, and LTP remained occluded (Blue arrowheads, FIGS. 5A, 6 and 5B). SynGAP α2 underwent modest dispersion following stimulation, but there was no significant rescue (Blue arrowheads, FIG. 5A, window 4, and FIG. 5B). It was previously found that phase separation mutant of SynGAP α1 (LDKD) only partially rescued the LTP and significantly lowered LTP threshold (Zeng et al., 2016). These results suggest that both the coiled-coil domain and PDZ ligand are required for LTP rescue in SynGAP KD neurons, and only SynGAP α1 harbors the necessary and sufficient domains for this.

Example 6: SynGAP β Regulates Dendritic Arbor Development, and Disruption of SynGAP α1 LLPS Switches its Rescue Directionality from Synaptic Plasticity (α1 Type) to Dendritic Arbor (β Type) Phenotype Various small G proteins, including Ras, Rap1, Rac1, and RhoA differentially regulate dendritic arbor development either by increasing dendritic complexity or by pruning dendritic branches (Fu et al., 2007; Saito et al., 2009; Sepulveda et al., 2010). The role of each SynGAP isoform in dendritic development was investigated.

Procedurally, hippocampal neurons plated on coverslips as described above were co-transfected at DIV 3-4 with pSUPER-SynGAP shRNA and shRNA-resistant GFP-SynGAP α1, α2, β, or γ rescue constructs. pCAG-DsRed2 was also co-transfected as a cell-fill for morphological analysis. Neurons were fixed at DIV 8-9 by incubating them with Parafix (4% paraformaldehyde, 4% Sucrose in PBS) for 15 min at room temperature, followed by incubation with 300 nM DAPI in PBS for 5 min at room temperature. Cells were briefly washed with PBS and mounted. Cells were observed using an LSM880 (Zeiss) microscope with a 40× objective lens (NA 1.3) with GaAsP detectors. To obtain Sholl profiles of dendritic arbors (Sholl, 1953), images of neurons were analyzed in the DsRed channel using Image J software. Circles were drawn with radii of 10, 20, 30, 40, 50, 100, and 150 µm from the center of the cell body, and dendritic crossing events for each concentric circle were counted. If a branch point fell on a line, it was counted as two crossings.

Figure 6B:
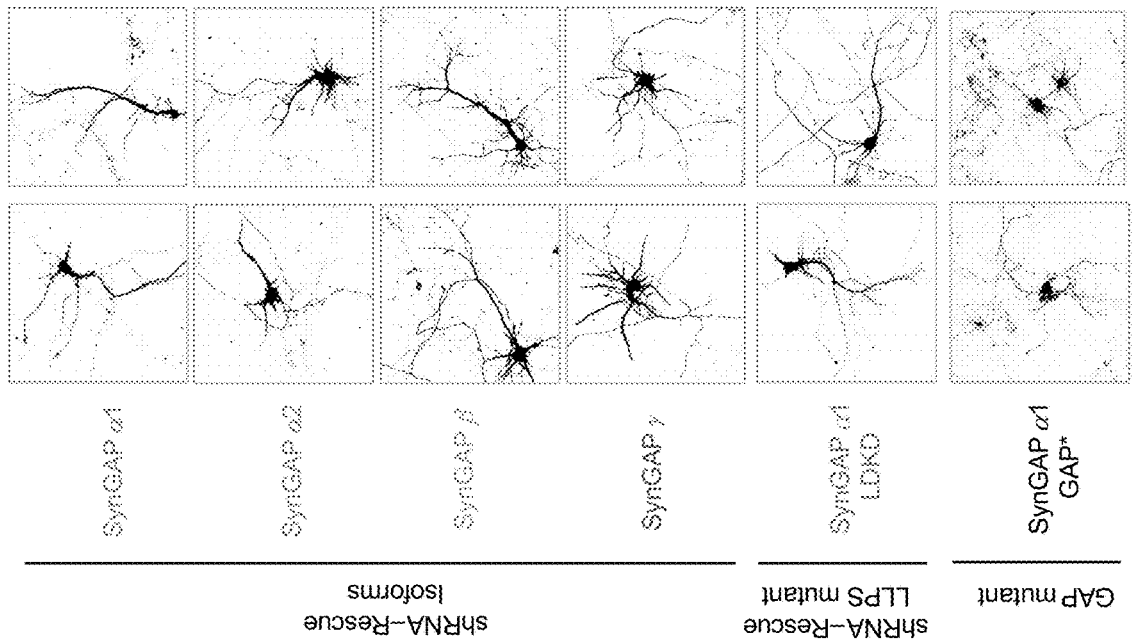
FIG. 6B shows representative images of neuronal morphology under each condition in FIG. 6A.
Figure 6A:
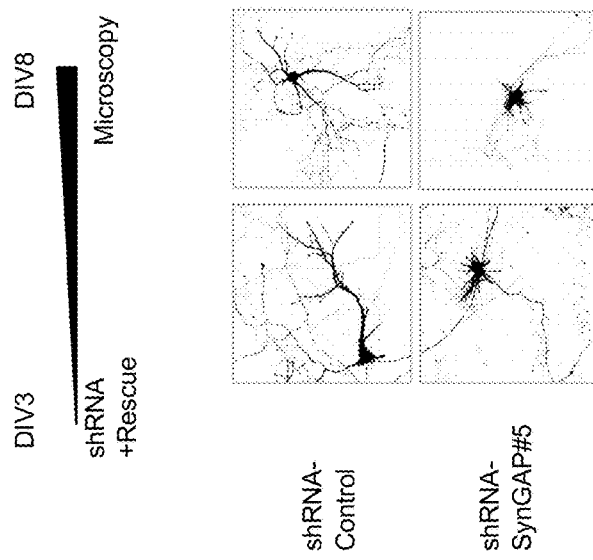
FIG. 6A shows time course of dendritic development assay. SynGAP was knocked down early in development (DIV 3) and was rescued by shRNA-resistant forms of each SynGAP isoform. Neuronal morphology was evaluated by observing co-transfected DsRed at DIV 8.
Figure 6C:
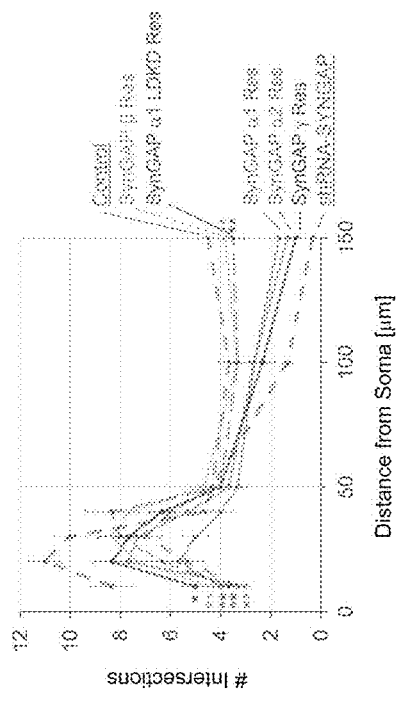
FIG. 6C shows Sholl analysis of dendritic branches presented as the mean number of intersections plotted as a function of distance from the center of the cell body (center=0). 15-20 neurons were analyzed per condition. Data from three independent experiments are shown as mean±SEM. Single asterisks indicate statistically significant rescues (N=8 neurons in each condition, *p<0.05, p<0.01, *p<0.001, One way ANOVA followed by Tukey test) compared to SynGAP knockdown. Note that only SynGAP β and SynGAP α1 L-D&K-D (phase separation mutant) rescued the dendritic arbor phenotype at 150 μm from the cell body.
Figure 6C:
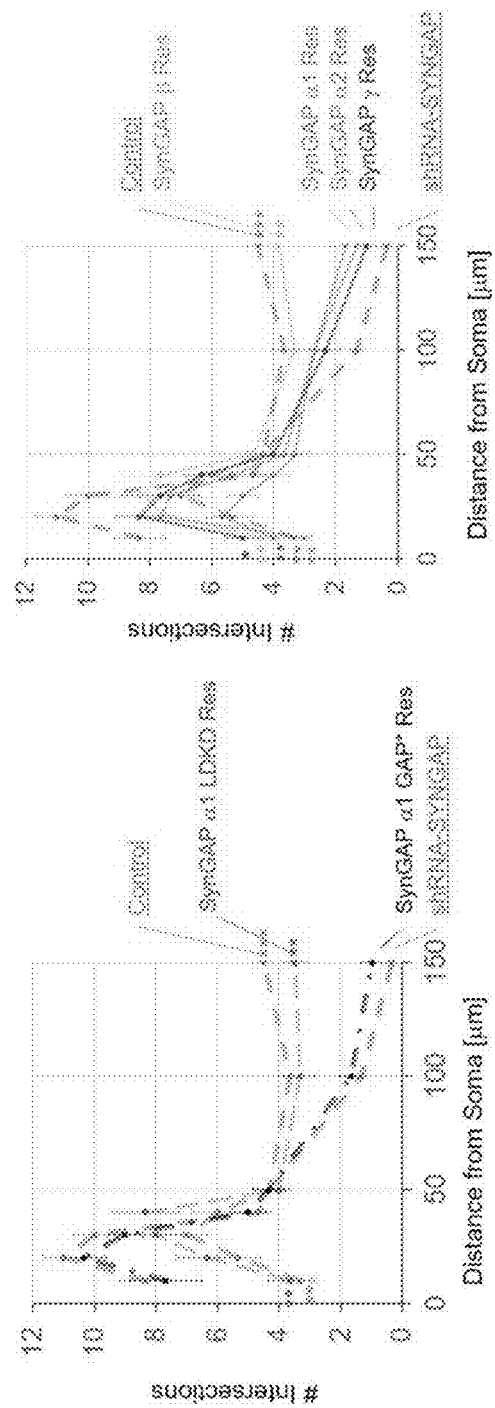
Figure 7:
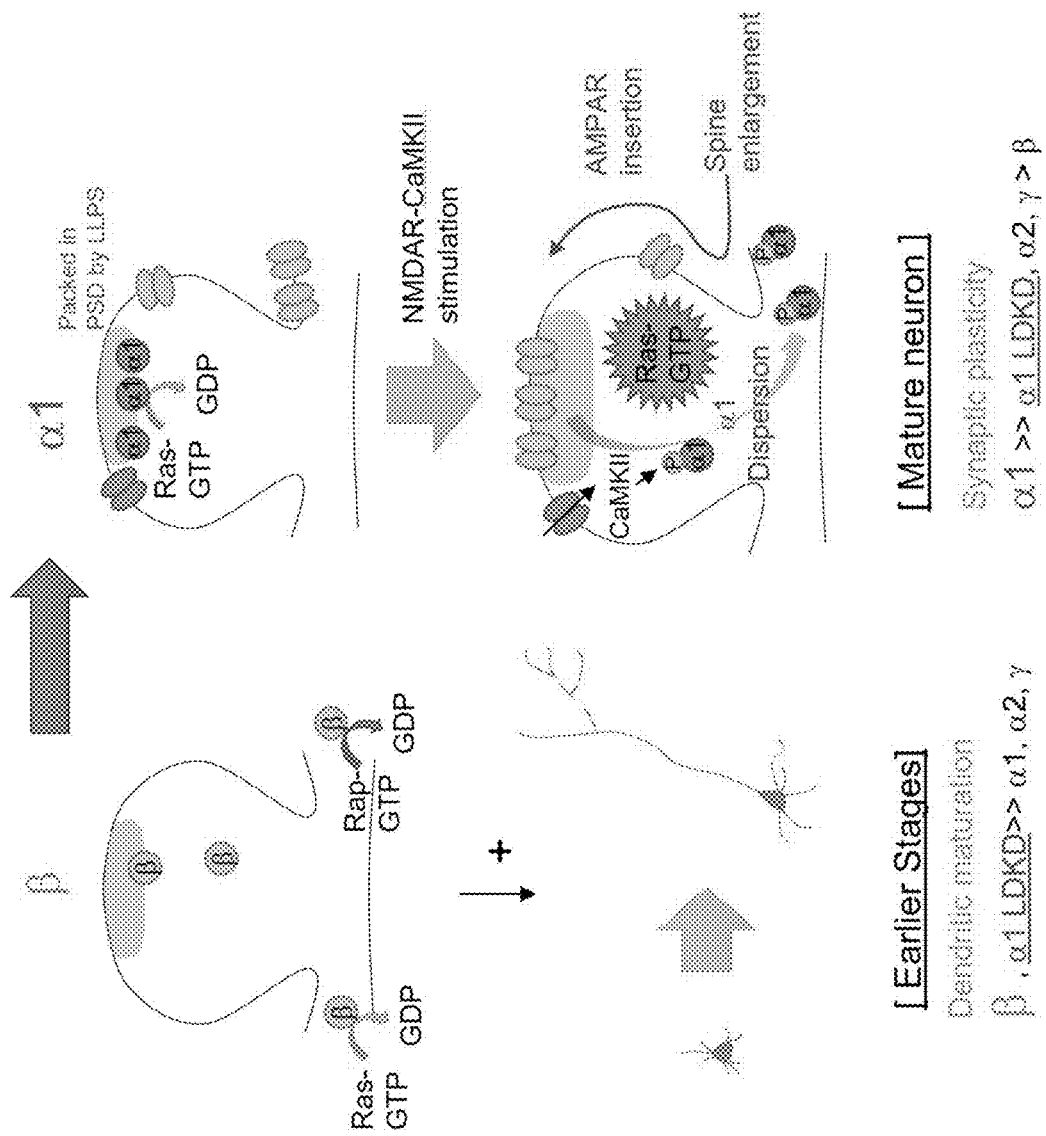
FIG. 7 shows exemplary schematic diagrams illustrating isoform-specific roles for SynGAP in neuronal maturation and/or synaptic plasticity. SynGAP β expresses early in development, has the lowest LLPS propensity resulting in cytosolic localization, possesses the highest GAP activity in cells, and facilitates proper dendritic development. Conversely, SynGAP α1 expresses later in development, undergoes strongest LLPS in spines resulting in dense expression in the PSD at the basal state, and is rapidly dispersed upon synaptic NMDAR-CaMKII activation. SynGAP α1 is the isoform most competent to rescue deficits in synaptic plasticity in SynGAP haploinsufficient models. Manipulation of biochemical properties of SynGAP isoforms shifted their rescue functionality (α1 to β type), highlighting a novel role for synaptic LLPS of SynGAP in determining the function of SynGAP in neurons.

Endogenous SynGAP in premature (DIV3) cultured hippocampal neurons was knocked down and dendritic arborization at DIV 8 was assayed (FIG. 6A). In control neurons, several basal dendrites can be observed proximal to the soma, usually in addition to one primary dendrite with pronounced distal branching (>100 µm) (FIG. 6B, window 1, FIG. D Control). Under conditions of SynGAP knockdown, dendritic complexity in the soma-proximal region was aberrantly enhanced, reminiscent of immature neuroblastoma cell lines with many proximal neurites. On the other hand, this counteracts with development of one distinct primary dendrite that is only branched at distal area (FIG. 6B, window 2, D shRNA-SynGAP). Coordinated activation of multiple small G proteins, such as Ras and Rac1, is known to be required for proper development of primary dendrites (Nakayama et al., 2000). When the various SynGAP isoforms was expressed in an attempt to rescue knockdown-dependent morphological changes, all SynGAP isoforms was reduced the number of dendritic branches sprouting from cell bodies (intersections at 10 µm) (FIGS. 6C-6D). Interestingly, only SynGAP β effectively rescued the knockdown-dependent decrease in distal dendritic complexity (150 µm), and regenerate one primary dendrite that is well branched at the distal side (FIGS. 6A-6C). Interestingly, expression of SynGAP α1 LDKD was sufficient for rescue of the primary dendrite phenotype, similar to the effect of expression of SynGAP β (FIGS. 6A-6C). This result suggests that disruption of SynGAP α1 LLPS drives a shift in rescue to one that is more b-centric, rescuing dendritic arbor deficits but not synaptic plasticity phenotypes. Previously, it was shown that SynGAP α1 LDKD, with weaker LLPS propensity, retained the ability to rescue knockdown-dependent aberrant synaptic strengthening, but that this rescue results in altered and abnormally lowered LTP threshold (Zeng Cell 2016). Taken together, these results suggest that unique biochemical properties of the various SynGAP isoforms define their independent roles in regulating neuronal maturation and/or synaptic plasticity.

Figure 8A:
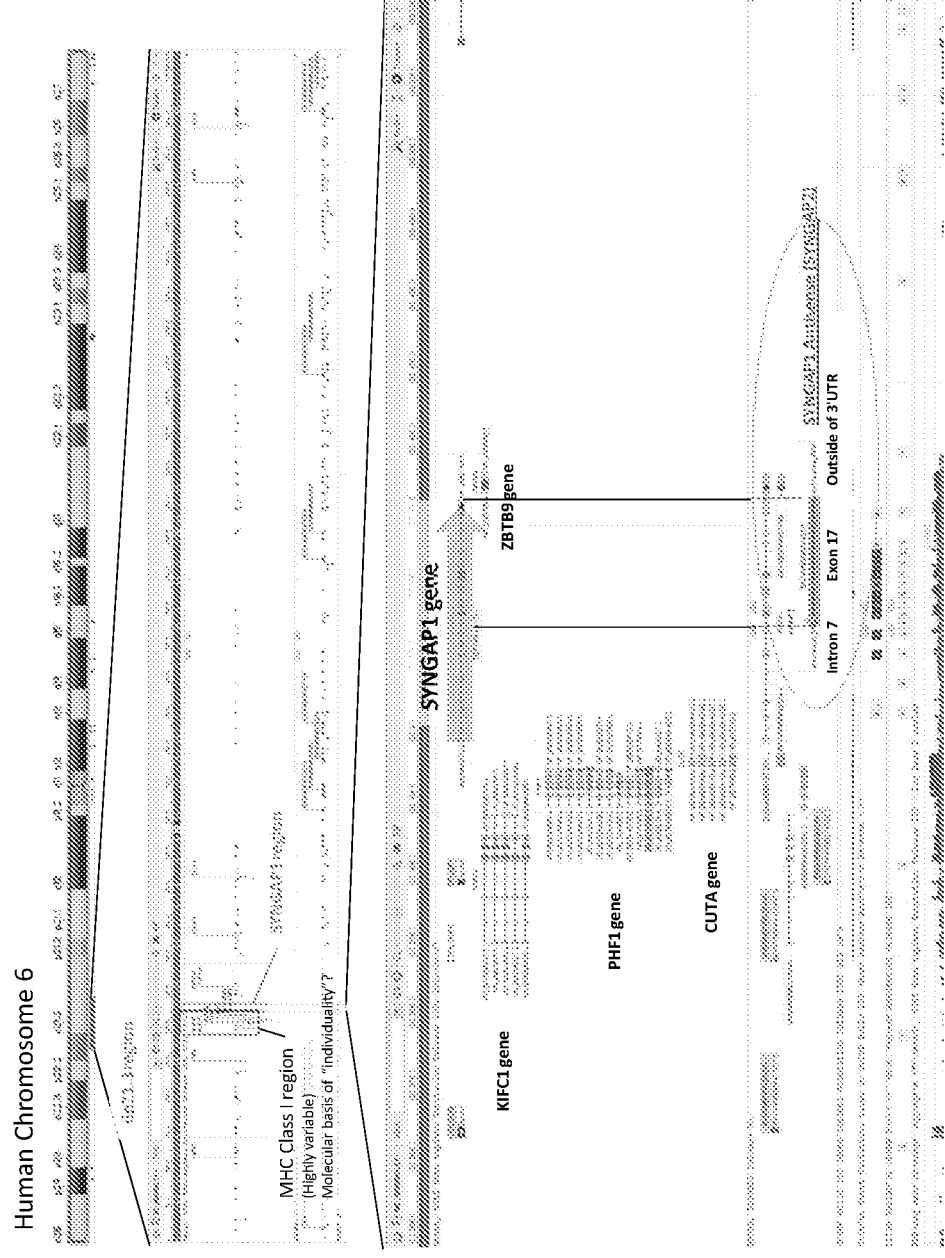
FIG. 8A shows the human chromosomal location of SynGAP2.
Figure 8B:
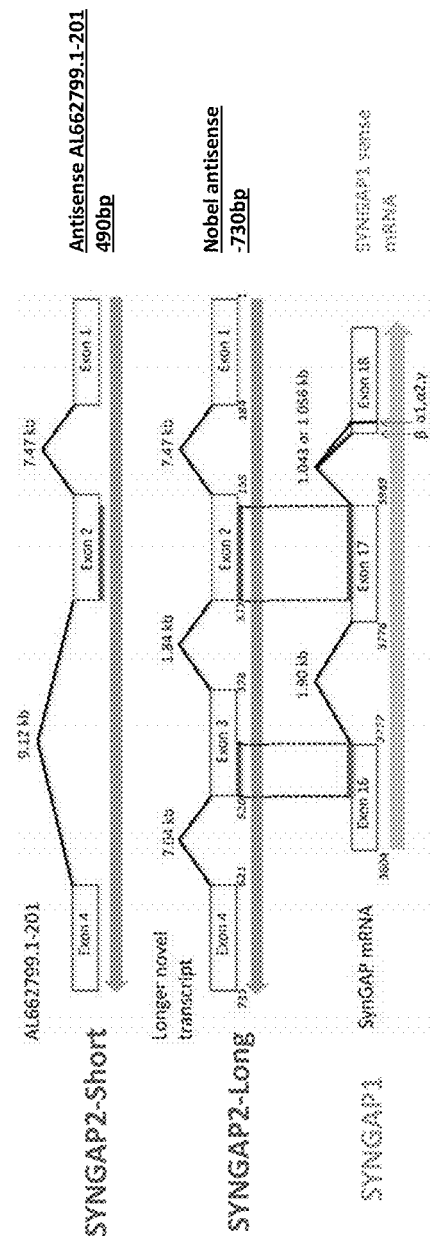
FIG. 8B shows that SynGAP2 has 2 splice variants. SYNGAP2-Short overlaps SYNGAP1 exon 17. SYNGAP2-Long overlaps with SYNGAP1 exon 16 and exon 17.

Example 7: A Natural Antisense Transcript of SynGAP is Expressed Only in Human, Potentially Regulating Sense SYNGAP1 Transcription It was recently identified that the genomic region at SynGAP expresses another transcript on the antisense strand. This gene is termed SynGAP2. SynGAP2 is a gene on human chromosome 6 that comprises at least two different isoforms (i.e., splice variants): one with 3 exons ("SYN-GAP2-Short") and another with 4 exons ("SYNGAP2-Long"). See FIGS. 8A-8B.

Figure 9:
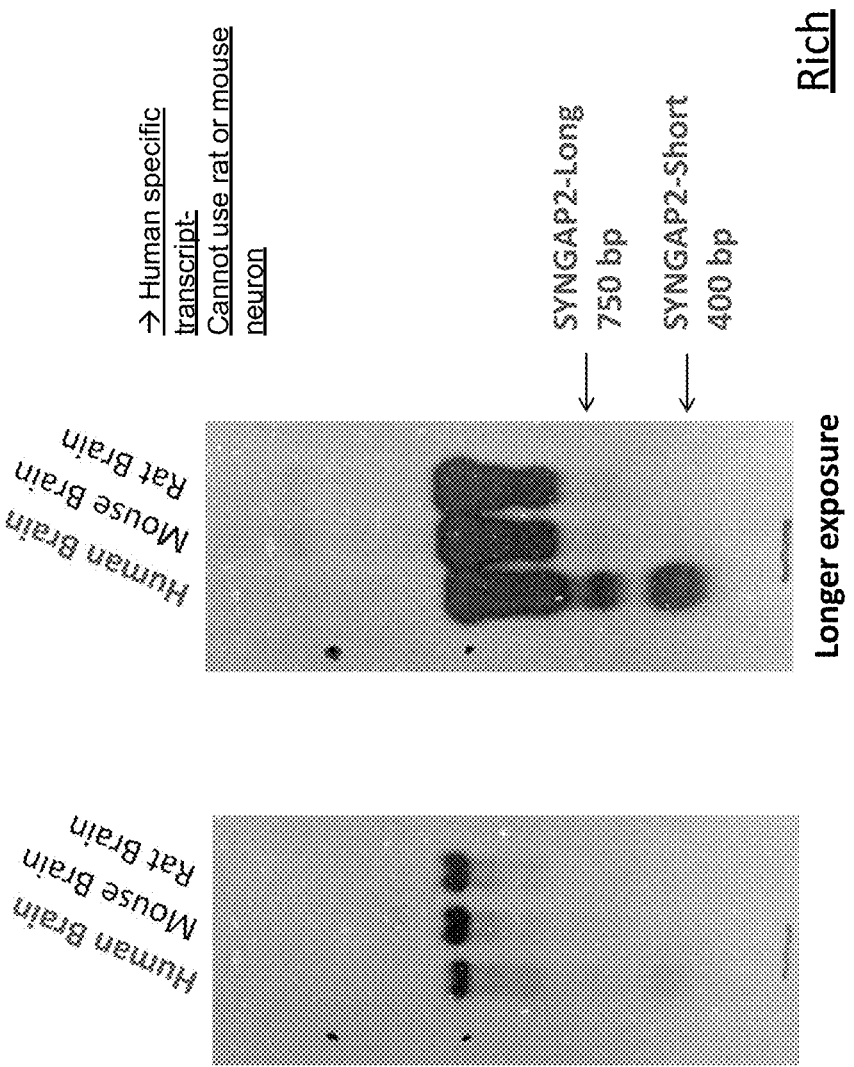
FIG. 9 shows Northern blotting of SYNGAP2 in human, mouse, and rat brain.

To confirm expression of different the antisense transcripts (i.e., variants), a Northern blot was run, looking for expression of both isoforms of SynGAP2. As shown in FIG. 9, expression of both SYNGAP2-Short and SYNGAP2-Long was detected in a human brain sample, but no expression of either isoform was detected in mouse brain or rat brain. These data suggest that expression of both SYN-GAP2-Short and SYNGAP2-Long are specific to human brain and not mouse or rat brain.

Figure 10:
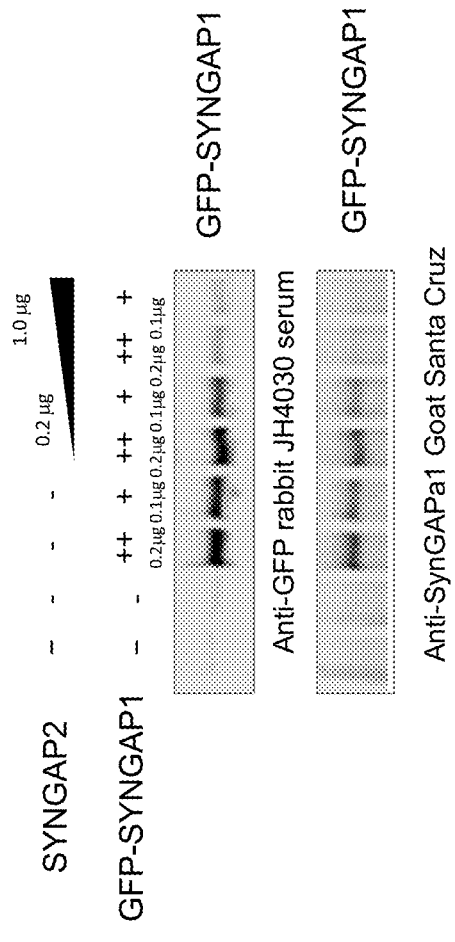
FIG. 10 shows protein expression of SynGAP1 in HEK 293 cells transfected with plasmids expressing SYNGAP2 and SYNGAP1.

Example 8: SynGAP2 Overexpression Negatively Regulates SynGAP1 Expression Level when Co-Expressed in HEK Cells It next was examined whether there was a correlation between SynGAP2 and SynGAP2. To determine the correlation, HEK-293 cells co-transfected with SynGAP1 and SynGAP2 using LipofectAMINE 2000-mediated transfection. Lysates were isolated and expression of SynGAP1 and SynGAP2 were detected via Western blot. As shown in FIG. 10, overexpression of SynGAP2 led to decreased protein expression of SynGAP1. These data suggest that co-expression of SYNGAP2 negatively regulates SYNGAP1 protein.

Figure 11:
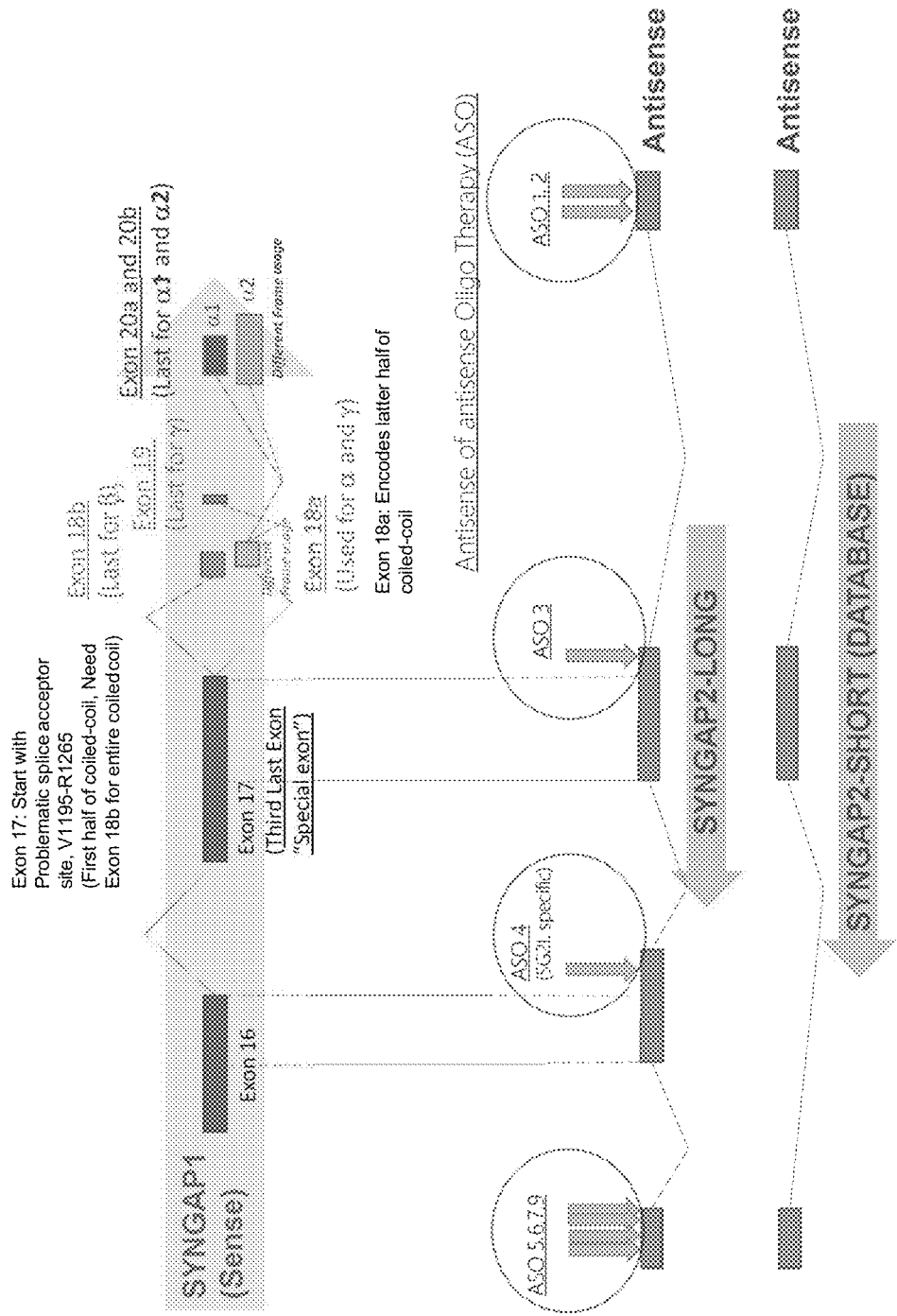
FIG. 11 shows a schematic of antisense oligo (ASO) targeting in SynGAP1 and SynGAP2.

Example 9: Antisense Oligonucleotides Targeting SYNGAP2 Effectively Knockdown SYNGAP2 in HEK Cells and Recovered SYNGAP1 Expression, and Antisense Oligonucleotides Targeting SYNGAP2 Overcome SYNGAP1 Haploinsufficiency, Recovering SYNGAP1 Protein Amount in Cells Given the correlation between SynGAP1 and SynGAP2 in HEK 293 cells in Example 8, it was next considered whether down-regulation of SYNGAP2 affects SYNGAP1 expression. As shown in FIG. 11, antisense oligo therapy (ASO) or shRNAs specifically targets SYNGAP2 but not SYNGAP1 that potentially rescues the SYNGAP1 expression levels in patients. Therefore, one can specifically target SYNGAP2, but not an isoform of SynGAP1.

Figure 12A:
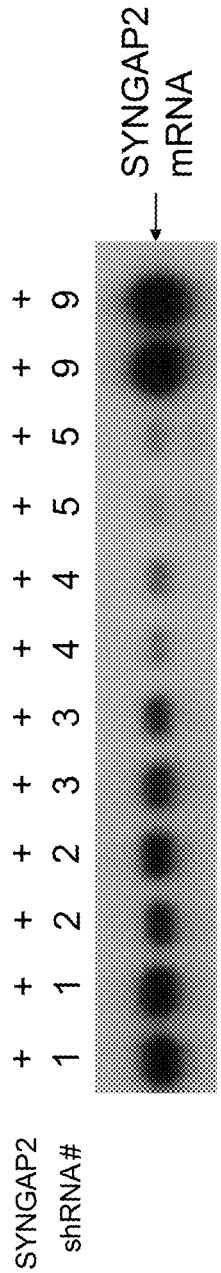
FIGS. 12A-12B show RNA levels of SynGAP2 examined by Northern blot in HEK cells transfected by indicated ASO plasmids.
Figure 12B:
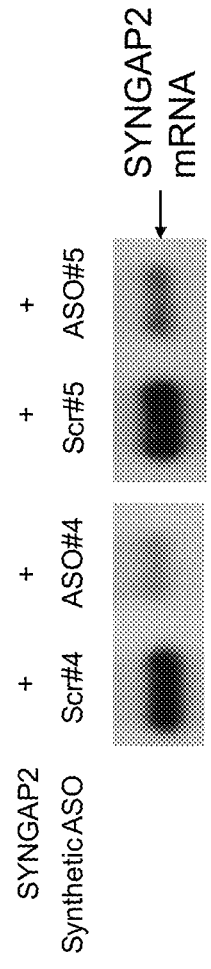
Figure 12C:
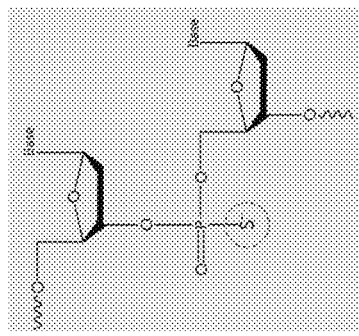
FIG. 12C shows ASO sequences that we used in plasmids treated in cells as shown in FIGS. 12A-12B.

Antisense oligo against SYNGAP2 were designed in plasmid vectors to control their expression levels. For reference, the designed plasmids were termed "pSUPER-shRNA SYNGAP2-ASO-#xx," wherein "xx" refers to an arbitrary oligo number. After transfection into HEK 293 cells, two ASOs, termed ASO-#4, and ASO-#5 effectively downregulate SYNGAP2 expression. See FIG. 12A, which shows a RNA expression of SynGAP2 via Northern blot. Further, as shown in FIG. 12B, co-transfection of antisense oligo ASO-#4, and ASO-#5 into HEK cells together with the SYNGAP2 plasmid described above effectively downregulate SYNGAP2 RNA levels. The sequences of ASO-#4, and ASO-#5 are shown in FIG. 12C. ASOs were chemically modified by phosphorothioates (PS/PO chimera).

Given that ASO-#4 and ASO-#5 were shown to knock down expression of SYNGAP2, it was next hypothesized that these two ASOs would affect expression of SynGAP1. To test this hypothesis, HEK 293 cells were transfected with plasmids comprising ASO-#4, ASO-#5, or ASO scrambled sequences. As shown in FIGS. 12A-12B, ASO-#4 and ASO-#5 increased SYNGAP1 expression suppressed by SYNGAP2 (n=2).

Figure 13A:
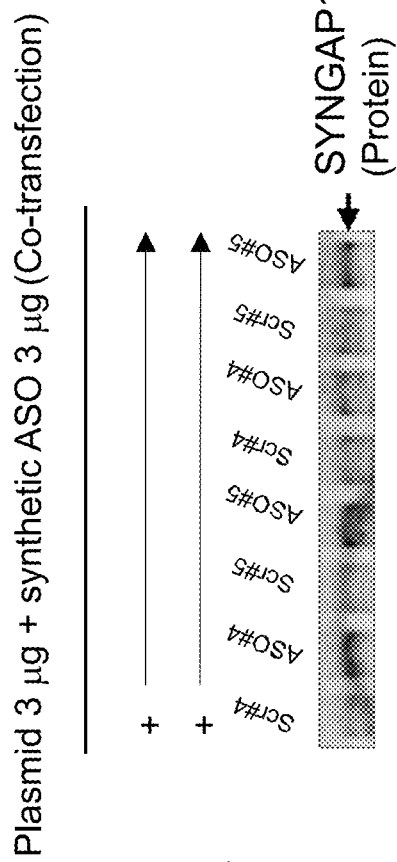
FIG. 13A-13B show a Western blot of lysates isolated from HEK cells were transfected by indicated plasmids.
Figure 13B:
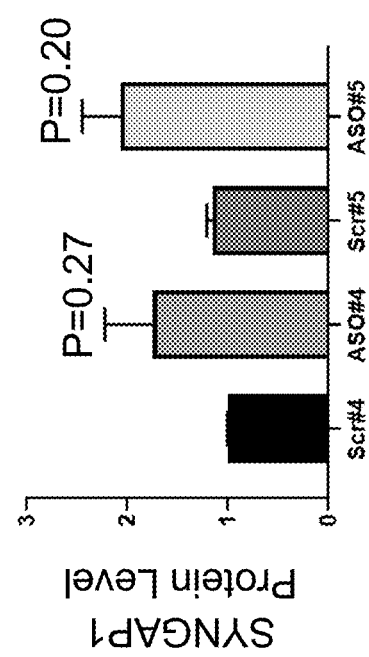
Figure 13C:
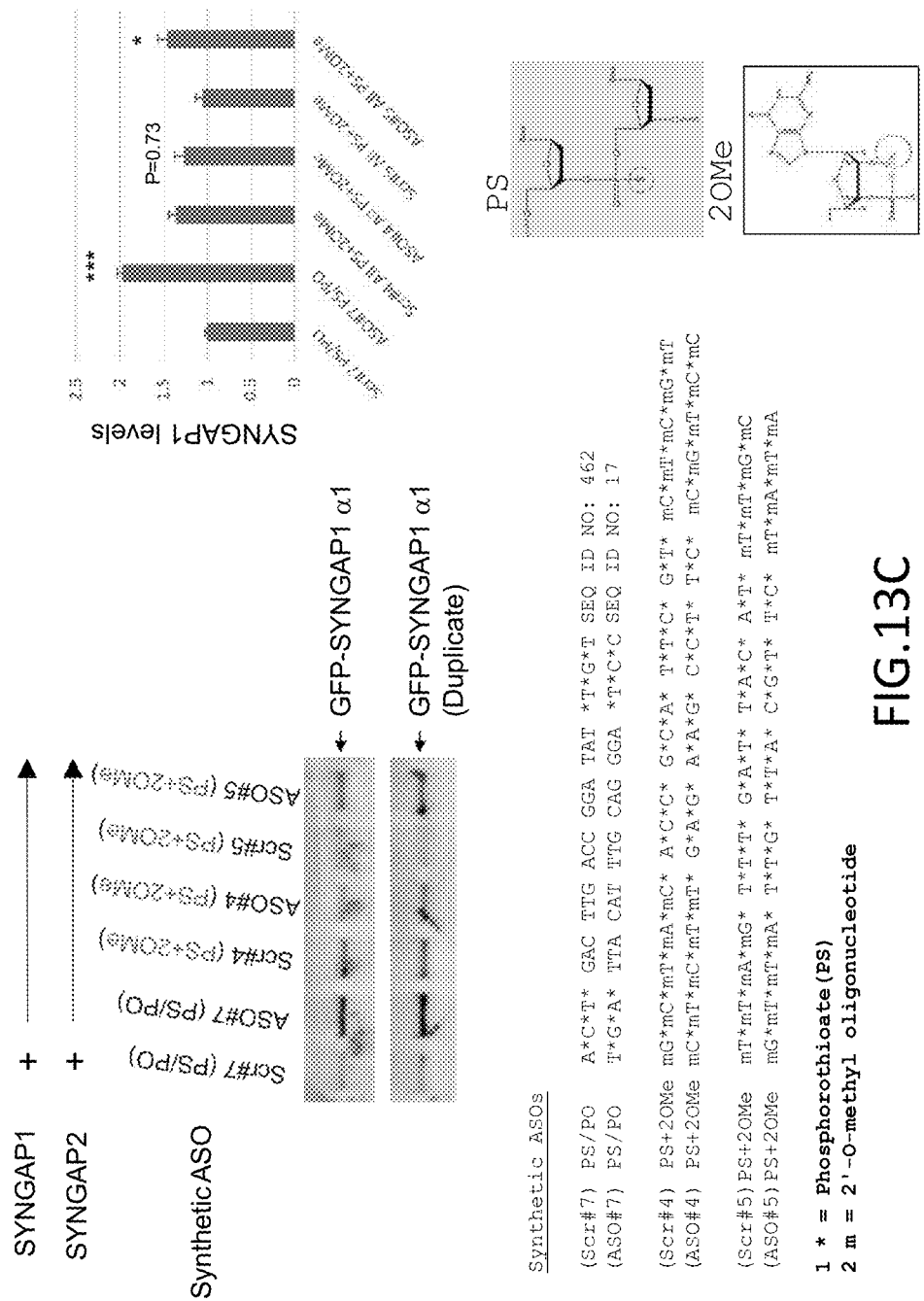
FIG. 13C shows chemical modification made to ASOs.

Finally, ASOs were chemically modified (See FIG. 13C) and plasmids comprising three modified ASOs (ASO-#4, ASO-#5, and ASO-#7) were transfected into HEK 293 cells. Lysates were isolated and a Western blot was run. As shown in FIGS. 13A-13B, transfection of each plasmid increased expression of SYNGAP1 protein expression Example 10. Exon Extensions in Exon 11 and Exon 18 (β Isoform) Lead to Truncated (Non-α1) Isoform Expression of SynGAP1

Figure 14:
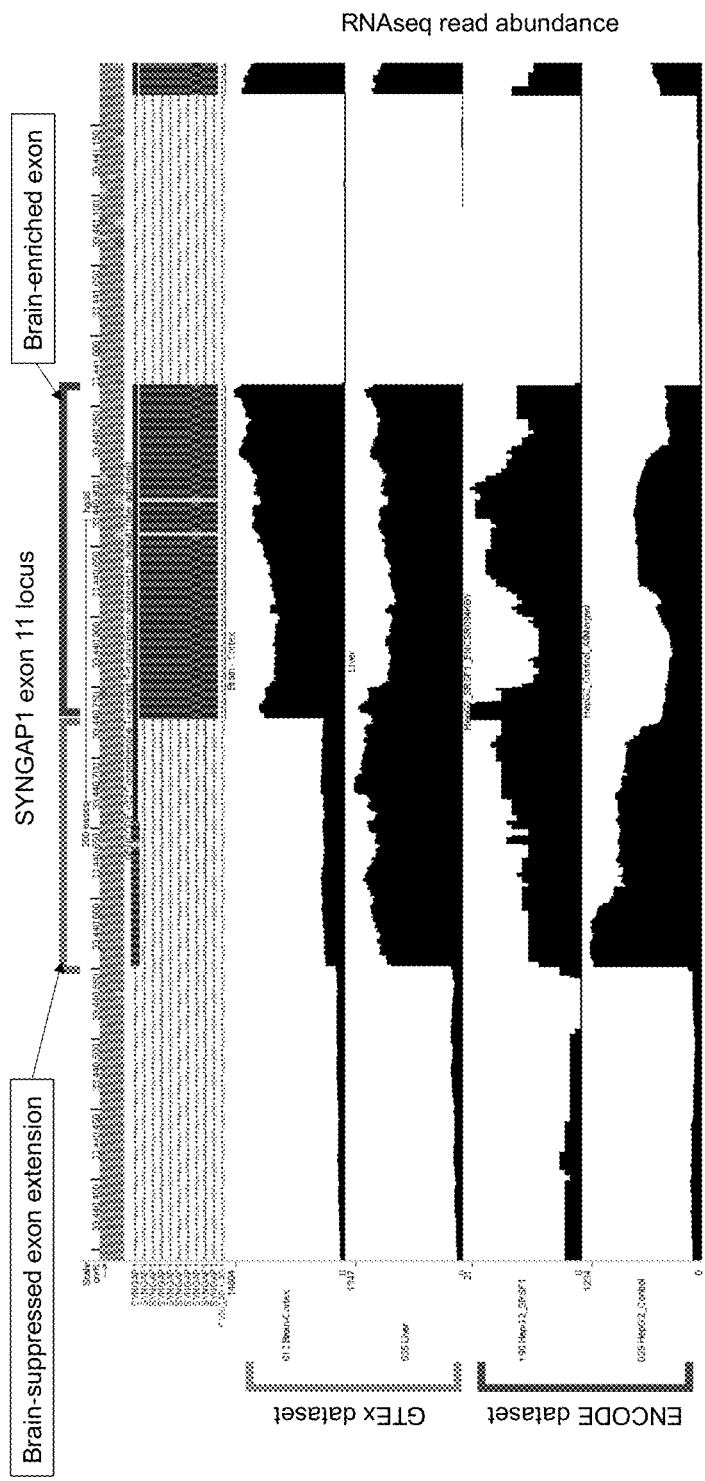
FIG. 14 shows exon 11 extension of SYNGAP1 is dominant outside the brain and depends on SRSF1.

As shown previously, alternative splicing and inclusion of an exon extension at the exon 17-18 junction leads to a truncated form of SynGAP1 (β isoform). Here, an exon extension at the exon 10-11 junction also leads to premature truncation of the SynGAP1 protein, and potentially nonsense mediated decay (NMD). This exon 11 extension is dominant outside the brain (See FIG. 14, top 2 panels) but is suppressed in the brain, which leads to the low expression of full-length SynGAP1 outside the brain. This exon 11 extension is increasingly suppressed over the course of development, leading to higher expression in adult brain. Suppressing this exon 11 extension through ASOs or other means can increase functional full-length SynGAP1 protein expression from the intact allele of patients. Additionally, it was found that SRSF1, a splicing factor, contributes to the inclusion of the exon 11 extension (See bottom 2 panels of FIG. 14), thereby providing a molecular target to suppress the exon extension.

A list of ASOs targeting the exon 11 extension suppression, exon 18 extension (β isoform) suppression, α2-isoform suppression, and γ isoform suppression is listed in Tables 2-5. These ASOs are aimed at a) increasing overall SYNGAP1 expression and/or b) increasing expression of the α1 isoform, as means to relieve SYNGAP1 patient symptoms. These ASOs may be used in the DNA or RNA form, and may be modified by one or more chemical modifications including: phosphorothioates, phosphoroamidates, 2'-O-methyl oligonucleotides, 2'-O-methoxy-ethyl oligonucleotides, locked nucleic acids, and phosphoroamidate morpholinos.

Statistics in Examples

In the above examples, all data are expressed as means±S.E.M. of values. One-way ANOVAs were used, followed by Tukey post hoc for multiple comparisons unless otherwise specified. If the interaction between two-factors was observed in Two-way ANOVA, individual Tukey post-hoc tests were performed to compare the measures as a function of one factor in each fixed levels of another factor unless otherwise specified. Statistical analyses and preparations of graphs were performed using SPSS 9.0, Excel 2010, or GraphPad Prism 4.0/5.0 software ($*p<0.05$; $p<0.01$; $*p<0.001$).

OTHER ASPECTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

REFERENCES

Aceti, M., Creson, T. K., Vaissiere, T., Rojas, C., Huang, W. C., Wang, Y. X., Petralia, R. S., Page, D. T., Miller, C. A., and Rumbaugh, G. (2015). SynGAP1 haploinsufficiency damages a postnatal critical period of pyramidal cell structural maturation linked to cortical circuit assembly. Biol Psychiatry 77, 805-815.

Araki, Y., Zeng, M., Zhang, M., and Huganir, R. L. (2015). Rapid dispersion of SynGAP from synaptic spines triggers AMPA receptor insertion and spine enlargement during LTP. Neuron 85, 173-189.

Berryer, M. H., Hamdan, F. F., Klitten, L. L., Moller, R. S., Carmant, L., Schwartzentruber, J., Patry, L., Dobrzeniecka, S., Rochefort, D., Neugnot-Cerioli, M., et al. (2013). Mutations in SYNGAP1 cause intellectual disability, autism, and a specific form of epilepsy by inducing haploinsufficiency. Hum Mutat 34, 385-394.

Carlisle, H. J., Manzerra, P., Marcora, E., and Kennedy, M. B. (2008). SynGAP regulates steady-state and activity-dependent phosphorylation of cofilin. J Neurosci 28, 13673-13683.

Carvill, G. L., Heavin, S. B., Yendle, S. C., McMahon, J. M., O'Roak, B. J., Cook, J., Khan, A., Dorschner, M. O., Weaver, M., Calvert, S., et al. (2013). Targeted resequencing in epileptic encephalopathies identifies de novo mutations in CHD2 and SYNGAP1. Nat Genet 45, 825-830.

Chen, H. J., Rojas-Soto, M., Oguni, A., and Kennedy, M. B. (1998). A synaptic Ras-GTPase activating protein (p135 SynGAP) inhibited by CaM kinase II. Neuron 20, 895-904.

Chen, Y., Wang, P. Y., and Ghosh, A. (2005). Regulation of cortical dendrite development by Rap1 signaling. Mol Cell Neurosci 28, 215-228.

Clement, J. P., Aceti, M., Creson, T. K., Ozkan, E. D., Shi, Y., Reish, N. J., Almonte, A. G., Miller, B. H., Wiltgen, B. J., Miller, C. A., et al. (2012). Pathogenic SYNGAP1 Mutations Impair Cognitive Development by Disrupting Maturation of Dendritic Spine Synapses. Cell 151, 709-723.

Cook, E. H., Jr. (2011). De novo autosomal dominant mutation in SYNGAP1. Autism Res 4, 155-156.

Fu, Z., Lee, S. H., Simonetta, A., Hansen, J., Sheng, M., and Pak, D. T. (2007). Differential roles of Rap1 and Rap2 small GTPases in neurite retraction and synapse elimination in hippocampal spiny neurons. J Neurochem 100, 118-131.

Grant, S. G., and O'Dell, T. J. (2001). Multiprotein complex signaling and the plasticity problem. Curr Opin Neurobiol 11, 363-368.

Guo, X., Hamilton, P. J., Reish, N. J., Sweatt, J. D., Miller, C. A., and Rumbaugh, G. (2009). Reduced expression of the NMDA receptor-interacting protein SynGAP causes behavioral abnormalities that model symptoms of Schizophrenia. Neuropsychopharmacology 34, 1659-1672.

Hamdan, F. F., Daoud, H., Piton, A., Gauthier, J., Dobrzeniecka, S., Krebs, M. O., Joober, R., Lacaille, J. C., Nadeau, A., Milunsky, J. M., et al. (2011). De novo SYNGAP1 mutations in nonsyndromic intellectual disability and autism. Biol Psychiatry 69, 898-901.

Hamdan, F. F., Gauthier, J., Spiegelman, D., Noreau, A., Yang, Y., Pellerin, S., Dobrzeniecka, S., Cote, M., Perreau-Linck, E., Carmant, L., et al. (2009). Mutations in SYNGAP1 in autosomal nonsyndromic mental retardation. N Engl J Med 360, 599-605.

Hyman, A. A., Weber, C. A., and Julicher, F. (2014). Liquid-liquid phase separation in biology. Annu Rev Cell Dev Biol 30, 39-58.

Khosravi-Far, R., Clark, G. J., Abe, K., Cox, A. D., McLain, T., Lutz, R. J., Sinensky, M., and Der, C. J. (1992). Ras (CXXX) and Rab (CC/CXC) prenylation signal sequences are unique and functionally distinct. J Biol Chem 267, 24363-24368.

Kim, J. H., Lee, H. K., Takamiya, K., and Huganir, R. L. (2003). The role of synaptic GTPase-activating protein in neuronal development and synaptic plasticity. J Neurosci 23, 1119-1124.

Kim, J. H., Liao, D., Lau, L. F., and Huganir, R. L. (1998). SynGAP: a synaptic RasGAP that associates with the PSD-95/SAP90 protein family. Neuron 20, 683-691.

Kohmura, N., Senzaki, K., Hamada, S., Kai, N., Yasuda, R., Watanabe, M., Ishii, H., Yasuda, M., Mishina, M., and Yagi, T. (1998). Diversity revealed by a novel family of cadherins expressed in neurons at a synaptic complex. Neuron 20, 1137-1151.

Komiyama, N. H., Watabe, A. M., Carlisle, H. J., Porter, K., Charlesworth, P., Monti, J., Strathdee, D. J., O'Carroll, C. M., Martin, S. J., Morris, R. G., et al. (2002). SynGAP regulates ERK/MAPK signaling, synaptic plasticity, and learning in the complex with postsynaptic density 95 and NMDA receptor. J Neurosci 22, 9721-9732.

Kumar, V., Zhang, M. X., Swank, M. W., Kunz, J., and Wu, G. Y. (2005). Regulation of dendritic morphogenesis by Ras-PI3K-Akt-mTOR and Ras-MAPK signaling pathways. J Neurosci 25, 11288-11299.

Li, W., Okano, A., Tian, Q. B., Nakayama, K., Furihata, T., Nawa, H., and Suzuki, T. (2001). Characterization of a novel synGAP isoform, synGAP-beta. J Biol Chem 276, 21417-21424.

Lin, D. T., Makino, Y., Sharma, K., Hayashi, T., Neve, R., Takamiya, K., and Huganir, R. L. (2009). Regulation of AMPA receptor extrasynaptic insertion by 4.1N, phosphorylation and palmitoylation. Nat Neurosci 12, 879-887.

Magee, T., and Marshall, C. (1999). New insights into the interaction of Ras with the plasma membrane. Cell 98, 9-12.

McMahon, A. C., Barnett, M. W., O'Leary, T. S., Stoney, P. N., Collins, M. O., Papadia, S., Choudhary, J. S., Komiyama, N. H., Grant, S. G., Hardingham, G. E., et al. (2012). SynGAP isoforms exert opposing effects on synaptic strength. Nat Commun 3, 900.

Michaelson, S. D., Ozkan, E. D., Aceti, M., Maity, S., Llamosas, N., Weldon, M., Mizrachi, E., Vaissiere, T., Gaffield, M. A., Christie, J. M., et al. (2018). SYNGAP1 heterozygosity disrupts sensory processing by reducing touch-related activity within somatosensory cortex circuits. Nat Neurosci 21, 1-13.

Moores, S. L., Schaber, M. D., Mosser, S. D., Rands, E., O'Hara, M. B., Garsky, V. M., Marshall, M. S., Pompliano, D. L., and Gibbs, J. B. (1991). Sequence dependence of protein isoprenylation. J Biol Chem 266, 14603-14610.

Nakayama, A. Y., Harms, M. B., and Luo, L. (2000). Small GTPases Rac and Rho in the maintenance of dendritic spines and branches in hippocampal pyramidal neurons. J Neurosci 20, 5329-5338.

Parker, M. J., Fryer, A. E., Shears, D. J., Lachlan, K. L., McKee, S. A., Magee, A. C., Mohammed, S., Vasudevan, P. C., Park, S. M., Benoit, V., et al. (2015). De novo, heterozygous, loss-of-function mutations in SYNGAP1 cause a syndromic form of intellectual disability. Am J Med Genet A 167A, 2231-2237.

Rauch, A., Wieczorek, D., Graf, E., Wieland, T., Endele, S., Schwarzmayr, T., Albrecht, B., Bartholdi, D., Beygo, J., Di Donato, N., et al. (2012). Range of genetic mutations associated with severe non-syndromic sporadic intellectual disability: an exome sequencing study. Lancet 380, 1674-1682.

Reche, P. A., and Reinherz, E. L. (2003). Sequence variability analysis of human class I and class II MHC molecules: functional and structural correlates of amino acid polymorphisms. J Mol Biol 331, 623-641.

Rumbaugh, G., Adams, J. P., Kim, J. H., and Huganir, R. L. (2006). SynGAP regulates synaptic strength and mitogen-activated protein kinases in cultured neurons. Proc Natl Acad Sci USA 103, 4344-4351.

Saito, Y., Oinuma, I., Fujimoto, S., and Negishi, M. (2009). Plexin-B1 is a GTPase activating protein for M-Ras, remodelling dendrite morphology. EMBO Rep 10, 614-621.

Schafer, S. T., Paquola, A. C. M., Stern, S., Gosselin, D., Ku, M., Pena, M., Kuret, T. J. M., Liyanage, M., Mansour, A. A., Jaeger, B. N., et al. (2019). Pathological priming causes developmental gene network heterochronicity in autistic subject-derived neurons. Nat Neurosci 22, 243-255.

Sepulveda, F. J., Bustos, F. J., Inostroza, E., Zuniga, F. A., Neve, R. L., Montecino, M., and van Zundert, B. (2010). Differential roles of NMDA Receptor Subtypes NR2A and NR2B in dendritic branch development and requirement of RasGRF1. J Neurophysiol 103, 1758-1770.

Shin, Y., and Brangwynne, C. P. (2017). Liquid phase condensation in cell physiology and disease. Science 357.

Simanshu, D. K., Nissley, D. V., and McCormick, F. (2017). RAS Proteins and Their Regulators in Human Disease. Cell 170, 17-33.

Sommer, S. (2005). The importance of immune gene variability (MHC) in evolutionary ecology and conservation. Front Zool 2, 16.

Tan, C. A., Topper, S., Del Gaudio, D., Nelakuditi, V., Shchelochkov, O., Nowaczyk, M. J., Zeesman, S., Brady, L., Russell, L., Meeks, N., et al. (2015). Characterization of patients referred for non-specific intellectual disability testing: the importance of autosomal genes for diagnosis. Clin Genet. UK-DDD-study (2015). Large-scale discovery of novel genetic causes of developmental disorders. Nature 519, 223-228.

Vissers, L. E., de Ligt, J., Gilissen, C., Janssen, I., Steehouwer, M., de Vries, P., van Lier, B., Arts, P., Wieskamp, N., del Rosario, M., et al. (2010). A de novo paradigm for mental retardation. Nat Genet 42, 1109-1112.

Wright, L. P., and Philips, M. R. (2006). Thematic review series: lipid posttranslational modifications. CAAX modification and membrane targeting of Ras. J Lipid Res 47, 883-891.

Writzl, K., and Knegt, A. C. (2013). 6p21.3 microdeletion involving the SYNGAP1 gene in a patient with intellectual disability, seizures, and severe speech impairment. Am J Med Genet A 161, 1682-1685.

Zeng, M., Shang, Y., Araki, Y., Guo, T., Huganir, R. L., and Zhang, M. (2016). Phase Transition in Postsynaptic Densities Underlies Formation of Synaptic Complexes and Synaptic Plasticity. Cell 166, 1163-1175 e1112.

Zhu, J. J., Qin, Y., Zhao, M., Van Aelst, L., and Malinow, R. (2002). Ras and Rap control AMPA receptor trafficking during synaptic plasticity. Cell 110, 443-455.

What is claimed is:

1. A method of treating a SynGAP-associated neurodevelopmental disorder in a subject in need thereof, the method comprising administering an effective amount of an antisense oligonucleotide (ASO), wherein administering the ASO modulates expression of one or more isoforms of synaptic GTPase-activating protein (SynGAP1), and wherein the ASO targets SynGAP2 and comprises a sequence complementary to a SynGAP2 sequence.

2. The method of claim 1, wherein the one or more isoforms of SynGAP comprise SynGAP1 α1, SynGAP1 α2, SynGAP1 β, SynGAP1 γ, or any combination thereof.

3. The method of claim 1, wherein the SynGAP-associated neurodevelopmental disorder comprises an intellectual disability (ID), autism spectrum disorders (ASD), epilepsy, or schizophrenia.

4. The method of claim 1, further comprising:
(a) obtaining a sample from the subject; and
(b) assaying the expression of the one or more isoforms of SynGAP1 in the sample,
wherein the sample is a cell line, tissue, or blood,
wherein the sample is neurological tissue or neurological fluid, or
wherein the sample is hippocampal cells.

5. The method of claim 4, wherein the sample in the subject has aberrant expression of Ras, Rap1, Rac1, or any combination thereof.

6. The method of claim 1, wherein administering the ASO increases expression of SynGAP1 protein.

7. The method of claim 1, wherein administering the ASO increases expression of one or more isoforms of SynGAP1.

8. The method of claim 1, wherein the ASO comprises SEQ ID NO:18, SEQ ID NO:15, or SEQ ID NO:17.

9. The method of claim 1, wherein the ASO consists of SEQ ID NO:18, SEQ ID NO:15, or SEQ ID NO:17.

* * * * *